US008142762B2

(12) United States Patent
Bagnol

(10) Patent No.: US 8,142,762 B2
(45) Date of Patent: Mar. 27, 2012

(54) METHODS OF USING GPR101 RECEPTORS TO IDENTIFY MODULATORS OF HYPOTHALAMIC PROOPIOMELANOCORTIN (POMC)-DERIVED BIOLOGICALLY ACTIVE PEPTIDE SECRETION

(75) Inventor: Didier Bagnol, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/298,740

(22) PCT Filed: May 30, 2007

(86) PCT No.: PCT/US2007/012758
§ 371 (c)(1),
(2), (4) Date: Oct. 16, 2009

(87) PCT Pub. No.: WO2007/142979
PCT Pub. Date: Dec. 13, 2007

(65) Prior Publication Data
US 2010/0056442 A1 Mar. 4, 2010

Related U.S. Application Data

(60) Provisional application No. 60/809,634, filed on May 31, 2006.

(51) Int. Cl.
*A61K 49/00* (2006.01)
*A61K 38/00* (2006.01)
*C12Q 1/68* (2006.01)
*G01N 33/53* (2006.01)
*G01N 33/567* (2006.01)

(52) U.S. Cl. ........ 424/9.2; 435/6.16; 435/6.17; 435/7.2; 514/1.1

(58) Field of Classification Search .................... None
See application file for complete search history.

(56) References Cited

FOREIGN PATENT DOCUMENTS

| EP | 1 243 648 A1 | 9/2002 |
|---|---|---|
| WO | WO 0136471 | 5/2001 |
| WO | WO 2009/142724 | 11/2009 |

OTHER PUBLICATIONS

Barsh et al., "Genetic approaches to studying energy balance: perception and integration," *Nat. Rev. Genet.*, 3:589-600 (2002).
Biebermann et al., "A role for beta-melanocyte-stimulating hormone in human body-weight regulation," *Cell Metab.*, 3:141-146 (2006).
Boutillier et al., "Transcriptional activation of the proopiomelanocortin gene by cyclic AMP-responsive element binding protein," *Pituitary*, 1:33-43 (1998).
Cone, "Anatomy and regulation of the central melanocortin system," *Nat. Neurosci.*, 8:571-578 (2005).
GenBank® Accession No. BC058443, "*Rattus norvegicus* proopiomelanocortin, mRNA (cDNA clone MGC: 72676, Image: 6919050), complete cds" (2006), [retrieved on May 18, 2006]. Retrieved from the Internet: http://www.ncbi.nlm.nih.gov/entrez/viewer.fcgi?db=nucleotide&val=34849848, 3 pages.
GenBank® Accession No. BC061215, "*Mus musculus* proopiomelanocortin-alpha, mRNA (cDNA clone MGC: 74362, Image: 30253829), complete cds" (2005), [retrieved on May 18, 2006]. Retrieved from the Internet: http://www.ncbi.nlm.nih.gov/entrez/viewer.fcgi?db=nucleotide&val=34174155, 3 pages.
GenBank® Accession No. BC065832, "*Homo sapiens* proopiomelanocortin (adrenocorticotropin/ beta-lipotropin/ alpha-melanocyte stimulating hormone/ beta-melanocyte stimulating hormone / beta-endorphin), mRNA (cDNA clone MGC: 75488, Image: 30392189), complete cds" (2005), [retrieved on May 18, 2006]. Retrieved from the Internet: http://www.ncbi.nlm.nih.gov/entrez/viewer.fcgi?db=nucleotide&val=41351383, 3 pages.
GenBank® Accession No. CAI22624, "G protein-coupled receptor 161 [*Homo sapiens*]" (2005), [retrieved on May 19, 2006]. Retrieved from the Internet: http://www.ncbi.nlm.nih.gov/entrez/query.fcgi?cmd=Retrieve&db=Protein&list_uids=56203275, 2 pages.
GenBank® Accession No. M15880, "Rat neuropeptide Y mRNA, complete cds" (1993), [retrieved on Feb. 10, 2011]. Retrieved from the Internet: http://www.ncbi.nlm.nih.gov/nuccore/205756, 1 page.
GenBank® Accession No. NM_000905, "*Homo sapiens* neuropeptide Y (NPY), mRNA" (2003), [retrieved on Feb. 10, 2011]. Retrieved from the Internet: http://www.ncbi.nlm.nih.gov/nuccore/4505448, 3 pages.
GenBank® Accession No. NM_012614, "Rattus norvegicus neuropeptide Y (Npy), mRNA" (2011), [retrieved on Feb. 11, 2011]. Retrieved from the Internet: http://www.ncbi.nlm.nih.gov/nuccore/NM_012614, 3 pages.
GenBank® Accession No. NM_023456, "Mus musculus neuropeptide Y (Npy), mRNA" (2002), [retrieved on Feb. 10, 2011]. Retrieved from the Internet: http://www.ncbi.nlm.nih.gov/nuccore/12963682, 2 pages.
GenBank® Accession No. X13_549287, "Predicted: similar to G protein-coupled receptor 101 [Canis familiaris]" (2005), [retrieved on May 18, 2006]. Retrieved from the Internet: http://www.ncbi.nlm.nih.gov/entrez/viewer.fcgi?db=protein&val=74009022, 2 pages.
GenBank® Accession No. X13_582650, "Predicted: similar to G protein-coupled receptor 101 [Bos taurus]" (2005), [retrieved on May 18, 2006]. Retrieved from the Internet: http://www.ncbi.nlm.nih.gov/entrez/viewer.fcgi?db=protein&val=76658708, 2 pages.

(Continued)

*Primary Examiner* — Robert Landsman
(74) *Attorney, Agent, or Firm* — Fish & Richardson P.C.

(57) ABSTRACT

The present invention relates to methods of using GPR101 G protein-coupled receptor (GPCR) to screen candidate compounds as modulators of hypothalamic proopiomelanocortin (POMC)-derived biologically active peptide secretion. Modulators of GPR101 receptor modulate hypothalamic POMC-derived biologically active peptide secretion and are useful in the treatment of POMC-derived biologically active peptide-related disorders. POMC-derived biologically active peptides include, but are not limited to, α-melanocyte stimulating hormone (α-MSH), β-melanocyte stimulating hormone (β-MSH) and γ-melanocyte stimulating hormone (γ-MSH). Agonists and partial agonists of GPR101 receptor stimulate hypothalamic α-MSH, β-MSH and γ-MSH secretion and are useful, for example, in the treatment and prevention of obesity and conditions related thereto (including but not limited to Type 2 diabetes, insulin resistance, and metabolic syndrome), inflammation-associated disorders, and pyrexia. Inverse agonists and antagonists of GPR101 receptor inhibit α-MSH, β-MSH and γ-MSH secretion and are useful, for example, in the treatment and prevention of disorders such as cachexia.

57 Claims, 13 Drawing Sheets

OTHER PUBLICATIONS

Grundy et al., "Definition of metabolic syndrome: Report of the National Heart, Lung, and Blood Institute/American Heart Association conference on scientific issues related to definition," *Circulation*, 109:433-438 (2004).
Heneka et al., "Expression and function of inducible nitric oxide synthase in neurons," *J. Neuroimmunol.*, 114:8-18 (2001).
Kopelman, "Obesity as a medical problem," *Nature*, 404:635-643 (2000).
Lee et al., "Discovery and mapping of ten novel G protein-coupled receptor genes," *Gene.*, 275:83-91 (2001).
Leibel, "The molecular genetics of the melanocortin pathway and energy homeostasis," *Cell Metab.*, 3:79-81 (2006).
Murphy et al., "Antipyretic potency of centrally administered alpha-melanocyte stimulating hormone," *Science*, 221:192-193 (1983).
National Institutes of Health, NIH Publication No. Jan. 3670, 40 pages (May 2001).
Perry et al., "Prospective study of risk factors for development of non-insulin dependent diabetes in middle aged British men," *BMJ*, 310:560-564 (1995).
Pritchard et al., "Pro-opiomelanocortin processing in the hypothalamus: impact on melanocortin signalling and obesity," *J. Endocrinol.*, 172:411-421 (2002).
Schwartz, "Central nervous system regulation of food intake," *Obesity*, 14:1S-8S (2006).
Usui et al., "Cyclic AMP-responsive region of the human proopiomelanocortin (POMC) gene," *Mol. Cell. Endocrinol.*, 62:141-146 (1989).
Wardlaw, "Hypothalamic proopiomelanocortin processing and the regulation of energy balance," *European Journal of Pharmacology*, 1-7 (2011).
Yang et al., "Ascorbic acid augments the adenylyl cyclase-cAMP system mediated Pomc mRNA expression and β-endorphin secretion from hypothalamic neurons in culture," *Brain Res.*, 706:243-248 (1996).
Yoon et al., "α-Melanocyte-stimulating hormone inhibits lipopolysaccharide-induced tumor necrosis factor-α production in leukocytes by modulating protein kinase A, p38 kinase, and nuclear factor κB signaling pathways," *J. Biol. Chem.*, 278:32914-32920 (2003).
Aronne, LJ, et al. New targets for obesity pharmacotherapy. Clinical Pharmacology and Therapeutics. 2007, vol. 81, No. 5, pp. 748-752.
Bates, B., et al. Characterization of Gpr101 expression and G-protein coupling selectivity. Brain Research. 2006, vol. 1087, pp. 1-14.
Deboer, M., et al. Therapy insight: use of melanocortin antagonists in the treatment of cachexia in chronic disease. Endocrinology and Metabolism. Nature Clinical Practice Endocrinology and Metabolism. 2006, vol. 2, No. 8, pp. 459-466.
Farooqi, et al. New advances in the genetics of early onset obesity. International Journal of Obesity. 2005, vol. 29, pp. 1149-1152.
Getting, S. Targeting melanocortin receptors as potential novel therapeutics. Pharmacology and Therapeutics. 2006, vol. 111, pp. 1-15.
Hillebrand, J., et al. To eat or not to eat; regulation by the melanocortin system. Physiology and Behavior. 2006, vol. 89, pp. 97-102.
Lee, Y., et al. A POMC variant implicates beta-melanocyte-stimulating hormone in the control of human energy balance. Cell Metabolism. 2006, vol. 3, pp. 135-140.
Li, G., et al. Hypothalamic pro-opiomelanocortin gene delivery ameliorates obesity and glucose intolerance in aged rats. Diabetologia. 2005, vol. 48, pp. 2376-2385.
Millington, G. Proopiomelanocortin (POMC): the cutaneous roles of its melanocortin products and receptors. Clinical and Experimental Dermatology. 2006, vol. 31, pp. 407-412.
Nilaweera, K., et al. G protein-coupled receptor 101 mRNA expression in the mouse brain: altered expression in the posterior hypothalamus and amygdala by energetic challenges.

METHODS OF USING GPR101 RECEPTORS TO IDENTIFY MODULATORS OF HYPOTHALAMIC PROOPIOMELANOCORTIN (POMC)-DERIVED BIOLOGICALLY ACTIVE PEPTIDE SECRETION

FIELD OF THE INVENTION

The present invention relates to methods of using GPR101 G protein-coupled receptor (GPCR) to screen candidate compounds as modulators of hypothalamic proopiomelanocortin (POMC)-derived biologically active peptide secretion. Modulators of GPR101 receptor modulate hypothalamic POMC-derived biologically active peptide secretion and are useful in the treatment of POMC-derived biologically active peptide-related disorders. POMC-derived biologically active peptides include, but are not limited to, α-melanocyte stimulating hormone (α-MSH), β-melanocyte stimulating hormone (β-MSH) and γ-melanocyte stimulating hormone (γ-MSH). Agonists and partial agonists of GPR101 receptor stimulate hypothalamic α-MSH, β-MSH and γ-MSH secretion and are useful, for example, in the treatment and prevention of obesity and conditions related thereto (including but not limited to Type 2 diabetes, insulin resistance, and metabolic syndrome), inflammation-associated disorders, and pyrexia. Inverse agonists and antagonists of GPR101 receptor inhibit α-MSH, β-MSH and γ-MSH secretion and are useful, for example, in the treatment and prevention of disorders such as cachexia.

BACKGROUND OF THE INVENTION

The following discussion is intended to facilitate the understanding of the invention, but is not intended nor admitted to be prior art to the invention.

A. Obesity

Obesity, which is defined as increased mass of adipose tissue, confers a higher risk of cardiovascular and metabolic disorders such as Type 2 diabetes, hyperlipidemia, and coronary heart disease and an associated morbidity and mortality. Metabolic syndrome, a multiplex risk factor for cardiovascular disease, is defined on the basis of five criteria relating to obesity, hypertriglyceridemia, low HDL cholesterol, high blood pressure and high fasting glucose (Grundy et al, Circulation (2004) 109:433-438).

Obesity is now a major healthcare issue in the Western World and increasingly in some third world countries. The increase in numbers of obese people is due largely to the increasing preference for high fat content foods but also, and this can be a more important factor, the decrease in activity in most people's lives. In the last 10 years there has been a 30% increase in the incidence of obesity in the USA and that about 30% of the population of the USA is now considered obese.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25.0-29.9 $kg/m^2$, and obesity as a BMI of 30 $kg/m^2$ or greater (see Table A below).

TABLE A

CLASSIFICATION OF WEIGHT BY BODY MASS INDEX (BMI)

| BMI | CLASSIFICATION |
|---|---|
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gallbladder disease, cancer and diseases of reproduction. Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for Type 2 diabetes and coronary heart disease and the potential value of an integrated approach to the prevention of these conditions based on the prevention of obesity (Perry, et al, BMJ (1995) 310:560-564).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However many patients find this difficult and need additional help from drug therapy to maintain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have recently been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

There is an unmet medical need for agents that safely decrease body weight. The present invention is directed to this, as well as other, important end.

B. Proopiomelanocortin (POMC) in Hypothalamus

The hypothalamic arcuate nucleus contains two discrete neuronal subsets, one that powerfully increases (orexigenic), and one that reduces (anorexigenic), food intake. The subset of neurons that increases food intake coexpresses two orexigenic molecules, neuropeptide-Y (NPY) and agouti-related peptide (AgRP). The subset of neurons that decreases food intake expresses proopiomelanocortin (POMC).

POMC is a prohormone from which are proteolytically derived in the hypothalamus a number of biologically active peptides, including but not limited to adrenocorticotropic hormone (ACTH), β-endorphin, α-MSH, β-MSH, and γ-melanocyte stimulating hormone (γ-MSH). Rodents lack the N-terminal proteolytic cleavage site for β-MSH, unlike most species, and are therefore β-MSH deficient. α-MSH and β-MSH bind to (and are agonists at) the melanocortin-4 receptor (MC4R) with a comparably high affinity, and γ-MSH binds exclusively to (and is an agonist at) the melanocortin-3 receptor (MC3R). α-MSH and β-MSH have been shown to be anorexigenic. Elevation of intracellular cAMP stimulates POMC expression and secretion of POMC-derived biologically active peptide. (Exemplary POMC mRNA and amino acid sequence can be found at GenBank® Accession No. BC065832 for human, GenBank® Accession No. BC061215 for mouse and GenBank® Accession No. BC058443 for rat.) (Exemplary NPY mRNA and amino acid sequence can be found at GenBank® Accession No. NM_000905 for human, GenBank® Accession No. NM_023456 for mouse and GenBank® Accession No. NM_012614 for rat.)

Humans and mice genetically lacking all POMC-derived peptides are severely obese. Humans and mice lacking the MC4R are markedly obese and hyperphagic. Codominant mutations of MC4R accounts for up to 5% of early-onset, severe obesity in humans and, as such, are the most common monogenic cause of severe obesity in humans. Recently, a missense mutation of β-MSH in humans has been shown to lead to early-onset, severe obesity and hyperphagia, features of MC4R deficiency.

ACTH and α-MSH have been shown to be antipyretic (to reduce fever, or pyrexia).

α-MSH, which is expressed not only in neurons but also in pituitary cells, keratinocytes and macrophages, and γ-MSH and other agonists at MC1R and at MC3R have been shown to be anti-inflammatory.

See, e.g., Pritchard et al, J Endocrinol (2002) 172:411-421; Barsh et al, Nature Reviews (2002) 3:589-600; Cone, Nature Neuroscience (2005) 8:571-578; Schwartz, Obesity (2006) 14:1S-8S; Yang et al, Brain Research (1996) 706:243-248; Boutillier et al, Pituitary (1998) 1:3343; Lee et al, Cell Metabolism (2006) 3:135-140; Biebermann et al, Cell Metabolism (2006) 3:141-146; Leibel, Cell Metabolism (2006) 3:79-81; Heneka et al, Peptides (2006) 114:8-18; Yoon et al, J Biol Chem (2003) 278:32914-32920; Murphy et al, Science (1983) 221:192-193; and Usui et al, Mol Cell Endocrinol (1989) 62:141-146.

C. GPR101

GPR101 is an orphan G protein-coupled receptor (GPCR) reported to be expressed in hypothalamus (Lee et al, Gene (2001) 275:183-91) and reported to elevate intracellular cAMP consistent with being coupled to Gs (WO 01/36471 A2). Expression of GPR101 in brain has been detected predominantly in discrete nuclei, including hypothalamus (Bates et al, Brain Res (2006)). The coding region for GPR101 is contained within a single exon.

D. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

Claritin ® (allergies)
Paxil ® (depression)
Cozaar ® (hypertension)
Propulsid ® (reflux disease)
Pepcid ® (reflux)
Effexor ® (depression)
Allegra ® (allergies)
Diprivan ® (anesthesia)
Hytrin ® (hypertension)
Plavix ® (MI/stroke)
Xalatan ® (glaucoma)
Harnal ® (prostatic hyperplasia)
Prozac ® (depression)
Zoloft ® (depression)
Imitrex ® (migraine)
Risperdal ® (schizophrenia)
Gaster ® (ulcers)
Depakote ® (epilepsy)
Lupron ® (prostate cancer)
BuSpar ® (anxiety)
Wellbutrin ® (depression)
Toprol-XL ® (hypertension)
Singulair ® (asthma)
Vasotec ® (hypertension)
Zyprexa ®(psychotic disorder)
Zantac ® (reflux)
Serevent ® (asthma)
Atrovent ® (bronchospasm)
Cardura ®(prostatic hypertrophy)
Zoladex ® (prostate cancer)
Ventolin ® (bronchospasm)
Zyrtec ® (rhinitis)
Tenormin ® (angina)
Diovan ® (hypertension)

(Med Ad News 1999 Data).

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, Life Sciences (1988) 43:1095-1101. Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Gs-coupled GPCRs elevate intracellular cAMP levels. GPCRs coupled to Gi, Go, or Gz lower intracellular cAMP levels. Gq-coupled GPCRs elevate intracellular $IP_3$ and $Ca^{2+}$ levels.

There are also promiscuous G proteins, which appear to couple several classes of GPCRs to the phospholipase C pathway, such as G15 or G16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24]. A GPCR coupled to the phospholipase C pathway elevates intracellular $IP_3$ and $Ca^{2+}$ levels.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

Nucleotide sequence encoding human GPR101 polypeptide is given in SEQ ID NO: 1; the amino acid sequence of said encoded human GPR101 polypeptide is given in SEQ ID NO: 2. Nucleotide sequence encoding mouse GPR101 polypeptide is given in SEQ ID NO: 3; the amino acid sequence of said encoded mouse GPR101 polypeptide is given in SEQ ID NO: 4. Nucleotide sequence encoding rat GPR101 polypeptide is given in SEQ ID NO: 5; the amino acid sequence of said encoded rat GPR101 polypeptide is given in SEQ ID NO: 8.

Applicants unexpectedly have discovered that GPR101 receptor in hypothalamic arcuate nucleus is expressed by the anorexigenic POMC neuronal subset and that, at least with respect to the orexigenic NPY/AgRP neuronal subset, the expression is selective. Modulators of GPR101 receptor modulate hypothalamic POMC-derived biologically active peptide secretion and are useful in the treatment of POMC-derived biologically active peptide-related disorders. POMC-derived biologically active peptides include, but are not limited to, α-melanocyte stimulating hormone (α-MSH), β-melanocyte stimulating hormone (β-MSH) and γ-melanocyte stimulating hormone (γ-MSH).

The present invention relates to methods of using GPR101 receptor to screen candidate compounds as modulators of POMC-derived biologically active peptide secretion and to the use of said modulators in the treatment of POMC-derived biologically active peptide-related disorders. Agonists and partial agonists of GPR101 stimulate hypothalamic α-MSH and β-MSH and γ-MSH secretion and are useful in the treatment and prevention of obesity and conditions related thereto, including but not limited to Type 2 diabetes, insulin resistance and metabolic syndrome. Agonists and partial agonists of GPR101 are useful in promoting satiety. Agonists and partial agonists of GPR101 are useful in the treatment and prevention of hyperphagia. Agonists and partial agonists of GPR101 are useful in the treatment and prevention of pyrexia. Agonists and partial agonists of GPR101 are useful in the treatment and prevention of inflammation-associated disorders. Agonists and partial agonists of GPR101 are useful in decreasing body mass, in decreasing adiposity, in decreasing percentage body fat, and in decreasing food intake. Inverse agonists and antagonists of GPR101 inhibit hypothalamic α-MSH and β-MSH and γ-MSH secretion and are useful in the treatment and prevention of disorders such as cachexia. Inverse agonists and antagonists of GPR101 are useful in increasing body mass, in increasing adiposity, in increasing percentage body fat, and in increasing food intake.

In a first aspect, the invention features a method of identifying a candidate compound as a modulator of hypothalamic proopiomelanocortin (POMC)-derived biologically active peptide secretion, comprising the steps of:
  (a) contacting the candidate compound with a GPCR comprising an amino acid sequence selected from the group consisting of:
    (i) the amino acid sequence of SEQ ID NO: 2;
    (ii) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
    (iii) the amino acid sequence of SEQ ID NO: 4;
    (iv) the amino acid sequence of SEQ ID NO:6;
    (v) the amino acid sequence of a G protein-coupled receptor encoded by a polynucleotide hybridizing under stringent conditions to the complement of SEQ ID NO: 1, SEQ ID NO: 3 or SEQ ID NO: 5;
    (vi) the amino acid sequence of a G protein-coupled receptor having an amino acid sequence having at least about 70% identity to SEQ ID NO: 2, SEQ ID NO: 4 or SEQ ID NO: 6;

(vii) the amino acid sequence of a G protein-coupled receptor having a variant of the amino acid sequence of SEQ ID NO: 2, SEQ ID NO: 4 or SEQ ID NO: 6; and (viii) a biologically active fragment of any one of (i) to (vii);

wherein the receptor couples to a G protein; and (b) determining the ability of the compound to inhibit or stimulate functionality of the GPCR;

wherein the ability of the compound to inhibit or stimulate functionality of the GPCR is indicative of the compound being a modulator of hypothalamic proopiomelanocortin (POMC)-derived biologically active peptide secretion.

In certain embodiments, the GPCR comprises the amino acid sequence of SEQ ID NO: 2 or the amino acid sequence of a G protein-coupled receptor having at least about 70% identity to SEQ ID NO: 2.

In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

The invention additionally features a method of identifying a candidate compound as a modulator of hypothalamic proopiomelanocortin (POMC)-derived biologically active peptide secretion, comprising steps (a) and (b) of this first aspect, and further comprising:

(c) optionally synthesizing a compound which inhibits or stimulates functionality of the receptor in step (b);

(d) contacting a compound which inhibits or stimulates functionality of the receptor in step (b) in vitro with a cell that expresses a G protein-coupled receptor of the invention and is capable of secreting a POMC-derived biologically active peptide or with a vertebrate hypothalamic cell or with vertebrate hypothalamic tissue; and (e) determining whether the compound modulates secretion of a POMC-derived biologically active peptide from the cell that expresses a G protein-coupled receptor of the invention and is capable of secreting a POMC-derived biologically active peptide or from the vertebrate hypothalamic cell or from the vertebrate hypothalamic tissue;

wherein the ability of the candidate compound to modulate secretion of a POMC-derived biologically active peptide from the cell that expresses a G protein-coupled receptor of the invention and is capable of secreting a POMC-derived biologically active peptide or from the vertebrate hypothalamic cell or from the vertebrate hypothalamic tissue is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a) and (b) of this first aspect, and further comprising:

(c) optionally synthesizing a compound which inhibits or stimulates functionality of the receptor in step (b);

(d) administering a compound which inhibits or stimulates functionality of the receptor in step (b) to a vertebrate; and (e) determining whether the compound modulates secretion of a POMC-derived biologically active peptide in the vertebrate;

wherein the ability of the candidate compound to modulate secretion of a POMC-derived biologically active peptide in the vertebrate is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a) and (b) of this first aspect, and further comprising:

(c) optionally synthesizing a compound which inhibits or stimulates functionality of the receptor in step (b);

(d) contacting a compound which inhibits or stimulates functionality of the receptor in step (b) in vitro with a cell that expresses a G protein-coupled receptor of the invention and is capable of expressing POMC polypeptide or mRNA or with a vertebrate hypothalamic cell or with vertebrate hypothalamic tissue; and (e) determining whether the compound modulates expression of POMC polypeptide or mRNA in the cell that expresses a G protein-coupled receptor of the invention and is capable of expressing POMC polypeptide or mRNA or in the vertebrate hypothalamic cell or in the vertebrate hypothalamic tissue;

wherein the ability of the candidate compound to modulate expression of POMC polypeptide or mRNA in the cell that expresses a G protein-coupled receptor of the invention and is capable of expressing POMC polypeptide or mRNA or in the vertebrate hypothalamic cell or in the vertebrate hypothalamic tissue is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a) and (b) of this first aspect, and further comprising:

(c) optionally synthesizing a compound which inhibits or stimulates functionality of the receptor in step (b);

(d) administering a compound which inhibits or stimulates functionality of the receptor in step (b) to a vertebrate; and (e) determining whether the compound modulates expression of POMC polypeptide or mRNA in the vertebrate;

wherein the ability of the candidate compound to modulate expression of POMC polypeptide or mRNA in the vertebrate is indicative of the compound being a modulator of POMC-derived biologically active peptide secretion.

In certain embodiments, the POMC-derived biologically active peptide of step (e) is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, the G protein-coupled receptor of the invention is a G protein-coupled receptor having the amino acid sequence of SEQ ID NO: 2 or an endogenous or non-endogenous G protein-coupled receptor having an amino acid sequence having at least about 70% identity to SEQ ID NO: 2.

In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is a hypothalamic cell, a pituitary cell, a skin cell or a leukocyte. In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is an immortalized cell. In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is not an immortalized cell.

In certain embodiments, said determining whether the compound modulates secretion of a POMC-derived biologically active peptide is carried out by a process comprising hypothalamic slice assay. In certain embodiments, said hypothalamic slice assay is rat hypothalamic slice assay. In certain embodiments, said hypothalamic slice comprises a POMC neuron. In certain embodiments, said hypothalamic slice comprises a POMC neuron comprising GPR101.

In certain embodiments, the vertebrate hypothalamic tissue is mammalian hypothalamic tissue. In certain embodiments, the mammalian hypothalamic tissue is non-human mammalian hypothalamic tissue, such as but not limited to rat or mouse hypothalamic tissue. In certain embodiments, the vertebrate hypothalamic tissue is human hypothalamic tissue.

In certain embodiments, said determining whether the compound modulates expression of POMC mRNA in the vertebrate is carried out by a process comprising in situ hybridization histochemical analysis. In certain embodiments, said determining whether the compound modulates expression of POMC mRNA in the vertebrate is carried out by a process comprising in situ hybridization histochemical analysis of hypothalamic tissue. In certain embodiments, said determining whether the compound modulates expression of POMC mRNA in the vertebrate is carried out by a process comprising in situ hybridization histochemical analysis of hypothalamic tissue comprising hypothalamic arcuate nucleus tissue. In certain embodiments, said determining whether the compound modulates expression of POMC mRNA in the vertebrate is carried out by a process comprising in situ hybridization histochemical analysis carried out on serial sections prepared from hypothalamic tissue.

In certain embodiments, the method comprises identifying an agonist of the GPCR. In certain embodiments, the method comprises identifying a partial agonist of the GPCR. In certain embodiments, the candidate compounds are screened as pharmaceutical agents for obesity or a condition related thereto. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke. It is expressly contemplated that each individual condition related to obesity is a separate embodiment within the scope of the present invention.

In certain embodiments, the method comprises identifying an agonist of the GPCR. In certain embodiments, the method comprises identifying a partial agonist of the GPCR. In certain embodiments, the candidate compounds are screened as pharmaceutical agents for promoting satiety.

In certain embodiments, the method comprises identifying an agonist of the GPCR. In certain embodiments, the method comprises identifying a partial agonist of the GPCR. In certain embodiments, the candidate compounds are screened as pharmaceutical agents for hyperphagia.

In certain embodiments, the method comprises identifying an agonist of the GPCR. In certain embodiments, the method comprises identifying a partial agonist of the GPCR. In certain embodiments, the candidate compounds are screened as pharmaceutical agents for pyrexia.

In certain embodiments, the method comprises identifying an agonist of the GPCR. In certain embodiments, the method comprises identifying a partial agonist of the GPCR. In certain embodiments, the candidate compounds are screened as pharmaceutical agents for an inflammation-associated disorder. In certain embodiments, the inflammation-associated disorder is selected from the group consisting of inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder. It is expressly contemplated that each individual inflammation-associated disorder is a separate embodiment within the scope of the present invention. In some embodiments, the brain inflammation-related disorder is selected from the group consisting of brain injury or trauma, multiple sclerosis, amyotrophic lateral sclerosis, Parkinson's disease, prion-associated disease, cerebral ischemia, AIDS dementia and Alzheimer's disease. It is expressly contemplated that each individual brain inflammation-related disorder is a separate embodiment within the scope of the present invention.

In certain embodiments, the method comprises identifying an agonist of the GPCR. In certain embodiments, the method comprises identifying a partial agonist of the GPCR. In certain embodiments, the candidate compounds are screened as agents that decrease an energy homeostasis-related parameter selected from the group consisting of body mass, adiposity, percentage body fat and food intake. In certain embodiments, the candidate compounds are screened as agents that decrease body mass. In certain embodiments, the candidate compounds are screened as agents that decrease adiposity. In certain embodiments, the candidate compounds are screened as agents that decrease percentage body fat. In certain embodiments, the candidate compounds are screened as agents that decrease food intake.

In certain embodiments, the method comprises identifying an agonist of the GPCR. In certain embodiments, the method comprises identifying a partial agonist of the GPCR. In certain embodiments, the candidate compounds are screened as pharmaceuticals agents for a POMC-derived biologically active peptide-related disorder ameliorated by increasing a level of secretion of the POMC-derived biologically active peptide. In certain embodiments, the level of secretion is a level of hypothalamic secretion.

In certain embodiments, the method comprises identifying an inverse agonist of the GPCR. In certain embodiments, the method comprises identifying an antagonist of the GPCR. In certain embodiments, the candidate compounds are screened as pharmaceutical agents for a cachexia. In some embodiments, the cachexia is selected from the group consisting of AIDS-related weight loss, cancer-related weight loss and anorexia-related weight loss. It is expressly contemplated that AIDS-related weight loss, cancer-related weight loss and anorexia-related weight loss are separate embodiments within the scope of the present invention.

In certain embodiments, the method comprises identifying an inverse agonist of the GPCR. In certain embodiments, the method comprises identifying an antagonist of the GPCR. In certain embodiments, the candidate compounds are screened as agents that increase an energy homeostasis-related parameter selected from the group consisting of body mass, adiposity, percentage body fat and food intake. In certain embodiments, the candidate compounds are screened as agents that increase body mass. In certain embodiments, the candidate compounds are screened as agents that increase adiposity. In certain embodiments, the candidate compounds are screened as agents that increase percentage body fat. In certain embodiments, the candidate compounds are screened as agents that increase food intake.

In certain embodiments, the method comprises identifying an inverse agonist of the GPCR. In certain embodiments, the method comprises identifying an antagonist of the GPCR. In certain embodiments, the candidate compounds are screened as pharmaceuticals agents for a POMC-derived biologically active peptide-related disorder ameliorated by decreasing a level of secretion of the POMC-derived biologically active peptide. In certain embodiments, the level of secretion is a level of hypothalamic secretion.

In certain embodiments, a candidate compound that stimulates functionality of the GPCR is a compound that stimulates hypothalamic POMC-derived biologically active peptide secretion. Agonists and partial agonists of the GPCR stimulate hypothalamic POMC-derived biologically active peptide secretion and are useful as pharmaceutical agents for obesity or a condition related thereto. Agonists and partial agonists of the GPCR stimulate hypothalamic POMC-derived biologically active peptide secretion and are useful as pharmaceutical agents for promoting satiety. Agonists and partial agonists of the GPCR stimulate hypothalamic POMC-derived biologically active peptide secretion and are useful as pharmaceutical agents for hyperphagia. Agonists and partial agonists of the GPCR stimulate hypothalamic POMC-derived biologically active peptide secretion and are useful as pharmaceutical agents for pyrexia. Agonists and partial agonists of the GPCR stimulate hypothalamic POMC-derived biologically active peptide secretion and are useful as pharmaceutical agents for an inflammation-associated disorder. Agonists and partial agonists of the GPCR stimulate hypothalamic POMC-derived biologically active peptide secretion and are useful as pharmaceutical agents for decreasing body mass. Agonists and partial agonists of the GPCR stimulate hypothalamic POMC-derived biologically active peptide secretion and are useful as pharmaceutical agents for decreasing adiposity. Agonists and partial agonists of the GPCR stimulate hypothalamic POMC-derived biologically active peptide secretion and are useful as pharmaceutical agents for decreasing percentage body fat. Agonists and partial agonists of the GPCR stimulate hypothalamic POMC-derived biologically active peptide secretion and are useful as pharmaceutical agents for decreasing food intake.

In certain embodiments, a candidate compound that inhibits functionality of the GPCR is a compound that inhibits hypothalamic POMC-derived biologically active peptide secretion. Inverse agonists and antagonists of the GPCR inhibit hypothalamic POMC-derived biologically active peptide secretion and are useful as pharmaceutical agents for a cachexia. Inverse agonists and antagonists of the GPCR inhibit hypothalamic POMC-derived biologically active peptide secretion and are useful as pharmaceutical agents for increasing body mass. Inverse agonists and antagonists of the GPCR inhibit hypothalamic POMC-derived biologically active peptide secretion and are useful as pharmaceutical agents for increasing adiposity. Inverse agonists and antagonists of the GPCR inhibit hypothalamic POMC-derived biologically active peptide secretion and are useful as pharmaceutical agents for increasing percentage body fat. Inverse agonists and antagonists of the GPCR inhibit hypothalamic POMC-derived biologically active peptide secretion and are useful as pharmaceutical agents for increasing food intake.

In certain embodiments, said method comprises determining whether the candidate compound is an agonist of the receptor. In certain embodiments, said method comprises determining whether the candidate compound is a partial agonist of the receptor. In certain embodiments, said method comprises determining whether the candidate compound is an inverse agonist of the receptor. In certain embodiments, said method comprises determining whether the candidate compound is an antagonist of the receptor.

In certain embodiments, said receptor is recombinant.

In certain embodiments, said contacting comprises contacting the candidate compound with a host cell or with membrane of a host cell comprising recombinant said receptor. In some embodiments, said host cell comprises an expression vector comprising a polynucleotide encoding the receptor. In certain embodiments, the host cell is a eukaryotic cell. In some embodiments, the eukaryotic cell is a yeast cell. In some embodiments, the eukaryotic cell is a melanophore cell. In some embodiments, the eukaryotic cell is a mammalian host cell. In some embodiments, the mammalian cell is an HEK-293 cell, a COS-7 cell or a CHO cell.

In some embodiments, said determining is carried out with membrane comprising the GPCR. In certain embodiments, said membrane comprising the GPCR is isolated.

In certain embodiments, the GPCR exhibits a detectable level of constitutive activity. In some embodiments, the constitutive activity is for increasing a level of intracellular cAMP. In some embodiments, the constitutive activity is for increasing a level of intracellular cAMP consistent with the GPCR being coupled to Gs. In some embodiments, the constitutive activity is for causing melanophore cells to undergo pigment dispersion.

In some embodiments, said contacting is carried out in the absence of a known ligand of the GPCR. By way of illustration and not limitation, in some embodiments, said contacting is carried out in the absence of a known agonist to the receptor. In some embodiments, said identifying is directly identifying.

In some embodiments, said contacting is carried out in the presence of a known ligand of the GPCR. In some embodiments, said contacting is carried out in the presence of a known modulator of the GPCR. In some embodiments, said contacting is carried out in the presence of a known agonist of the GPCR. In some embodiments, the known agonist of the GPCR is a known agonist of endogenous human GPR101. In some embodiments relating to said contacting in the presence of a known agonist of the GPCR, the candidate compound is contacted with the GPCR prior to the known agonist being contacted with the GPCR. In some embodiments relating to said contacting comprising contacting in the presence of a known agonist of the GPCR, the candidate compound is contacted with the GPCR for a period of up to several minutes prior to the known agonist being contacted with the GPCR. In some embodiments relating to said contacting comprising contacting in the presence of a known agonist of the GPCR, the candidate compound is contacted with the GPCR for a period of up to about 5 min, of up to about 10 min or of up to about 30 min prior to the known agonist being contacted with the GPCR.

In certain embodiments, the PCR is genomic PCR. In certain embodiments, the human DNA is human genomic DNA.

In some embodiments, PCR is RT-PCR. In some embodiments, the human DNA is human cDNA derived from a tissue or cell that expresses GPR101. In some embodiments, the human cDNA is derived from brain or hypothalamus. In some embodiments, the human cDNA is derived from a POMC neuronal cell.

In certain embodiments, the G protein-coupled receptor encoded by a polynucleotide that is amplifiable by polymerase chain reaction (PCR) on a human DNA sample using specific primers SEQ ID NO: 7 and SEQ ID NO: 8 is an endogenous GPR101 G protein-coupled receptor.

In some embodiments, the GPCR is endogenous. In some embodiments, the endogenous GPCR is a vertebrate GPCR. In some embodiments, the endogenous GPCR is a mammalian GPCR. In some embodiments, the endogenous GPCR is a human GPCR. In certain embodiments, the endogenous vertebrate, mammalian or human GPCR is GPR101. In some embodiments, the GPCR is non-endogenous.

In some embodiments, the G protein-coupled receptor encoded by a polynucleotide hybridizing under stringent conditions to the complement of SEQ ID NO: 1, SEQ ID NO: 3 or SEQ ID NO: 5 is an endogenous GPCR. In some embodiments, the endogenous GPCR is a vertebrate GPCR. In some embodiments, the endogenous GPCR is a mammalian GPCR. In some embodiments, the endogenous GPCR is a human GPCR. In certain embodiments, the endogenous vertebrate, mammalian or human GPCR is GPR101. In some embodiments, the G protein-coupled receptor encoded by a polynucleotide hybridizing under stringent conditions to the complement of SEQ ID NO: 1, SEQ ID NO: 3 or SEQ ID NO: 5 is a non-endogenous GPCR.

In certain embodiments, said determining is by a process comprising the measurement of a level of a second messenger. In some embodiments, said determining is by a process comprising the measurement of a level of a second messenger selected from the group consisting of cyclic AMP (cAMP), cyclic GMP (cGMP), inositol 1,4,5-triphosphate ($IP_3$), diacylglycerol (DAG), MAP kinase activity, MAPK/ERK kinase kinase-1 (MEKK1) activity, and $Ca^{2+}$. In some embodiments, said second messenger is cAMP. In certain embodiments, the second messenger is cAMP.

In certain embodiments, said determining is by a process comprising the use of a Melanophore assay. In certain embodiments, said determining is by a process comprising the measurement of a level of melanophore pigment dispersion.

In some embodiments, said determining is by a process comprising the measurement of a level of GTPγS binding to membrane comprising the GPCR.

In some embodiments, said determining is by a process comprising the use of a cAMP-responsive reporter assay.

In some embodiments, the candidate compound is not a compound known to be a ligand of a vertebrate GPR101 receptor. In some embodiments, the candidate compound is not a compound known to be an agonist, a partial agonist, an inverse agonist or an antagonist at a vertebrate GPR101 receptor. In some embodiments, the vertebrate is a mammal. In some embodiments, the vertebrate is a human.

In certain embodiments, the candidate compound is a small molecule. In some embodiments, the candidate compound is a small molecule with the proviso that the small molecule is not a polypeptide, an antibody or an antigen-binding fragment thereof, or a lipid. In some embodiments, the candidate compound is a small molecule with the proviso that the small molecule is not a polypeptide. In some embodiments, the candidate compound is a small molecule with the proviso that the small molecule is not an antibody or an antigen-binding fragment thereof. In some embodiments, the candidate compound is a small molecule with the proviso that the small molecule is not a lipid.

In some embodiments, the method further comprises the step of comparing the modulation of the receptor caused by the candidate compound to a second modulation of the receptor caused by contacting the receptor with a known modulator of the receptor.

In some embodiments, said method further comprises the step of formulating the modulator into a pharmaceutical composition. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises synthesis of the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises: optionally, determining the structure of the modulator; and providing the modulator or the name or structure of the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises: optionally, determining the structure of the modulator; optionally, providing the modulator or the name or structure of the modulator; and producing or synthesizing the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In a second aspect, the invention features a modulator identifiable according to a method of the first aspect.

In some embodiments, the modulator is identified according to a method of the first aspect.

In certain embodiments, the modulator is an agonist, a partial agonist, an inverse agonist, or an antagonist of the GPCR. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR. In some embodiments, the GPCR is a vertebrate GPR101 receptor. In some embodiments, the GPCR is a mammalian GPR101 receptor. In some embodiments, the GPCR is a human GPR101 receptor.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an agonist or a partial agonist with an $EC_{50}$ of less than about 10 µM, of less than about 1 µM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 µM. In some embodiments, the modulator is an agonist or a partial agonist with an $EC_{50}$ of less than a value selected from the interval of about 10 nM to 1 µM. In some embodiments, the modulator is an agonist or a partial agonist with an $EC_{50}$ of less than a value selected from the interval of about 10 nM to 100 nM. In some embodiments, the modulator is an agonist or a partial agonist with an $EC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 µM, of less than about 1 µM, of less than about 100 nM, or of less than about 10 nM in said assay. In some embodiments, the modulator is an agonist or a partial agonist with an $EC_{50}$ in said assay of less than a value selected from the interval of about 10 nM to 10 µM. In some embodiments, the modulator is an agonist or a partial agonist with an $EC_{50}$ in said assay of less than a value selected from the interval of about 10 nM to 1 µM. In some embodiments, the modulator is an agonist or a partial agonist with an $EC_{50}$ in said assay of less than a value selected from the interval of about 10 nM to 100 nM.

In some embodiments, the modulator is an inverse agonist or an antagonist with an $IC_{50}$ of less than about 10 µM, of less than about 1 µM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 µM. In some embodiments, the modulator is an inverse agonist or an antagonist with an $IC_{50}$ of less than a value selected from the interval of about 10 nM to 1 µM. In some embodiments, the modulator is an inverse antagonist or an antagonist with an $IC_{50}$ of less than a value selected from the interval of about 10 nM to 100 nM. In some embodiments, the modulator is an inverse agonist or an antagonist with an $IC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 µM, of less than about 1 µM, of less than about 100 nM, or of less than about 10 nM in said assay. In some embodiments, the modulator is an inverse agonist or an antagonist with an $IC_{50}$ in said assay of less than a value selected from the interval of about 10 nM to 10 µM. In some embodiments, the modulator is an inverse agonist or an antagonist with an $IC_{50}$ in said assay of less than a value selected from the interval of about 10 nM to 1 µM. In some embodiments, the modulator is an inverse agonist or an antagonist with an $IC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a third aspect, the invention features a pharmaceutical composition comprising a modulator of a vertebrate GPR101 receptor and a pharmaceutically acceptable carrier. In some embodiments, the vertebrate is a mammal. In some embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator of the vertebrate GPR101 receptor is an agonist, a partial agonist, an inverse agonist, or an antagonist of the vertebrate GPR101 receptor. In certain embodiments, the modulator of the vertebrate GPR101 receptor is an agonist of the vertebrate GPR101 receptor. In certain embodiments, the modulator of the vertebrate GPR101 receptor is a partial agonist of the vertebrate GPR101 receptor. In certain embodiments, the modulator of the vertebrate GPR101 receptor is an inverse agonist of the vertebrate GPR101 receptor. In certain embodiments, the modulator of the vertebrate GPR101 receptor is an antagonist of the vertebrate GPR101 receptor.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an agonist or a partial agonist with an $EC_{50}$ of less than about 10 µM, of less than about 1 µM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 µM. In some embodiments, the modulator is an agonist or a partial agonist with an $EC_{50}$ of less than a value selected from the interval of about 10 nM to 1 µM. In some embodiments, the modulator is an agonist or a partial agonist with an $EC_{50}$ of less than a value selected from the interval of about 10 nM to 100 nM. In some embodiments, the modulator is an agonist or a partial agonist with an $EC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 µM, of less than about 1 µM, of less than about 100 nM, or of less than about 10 nM in said assay. In some embodiments, the modulator is an agonist or a partial agonist with an $EC_{50}$ in said assay of less than a value selected from the interval of about 10 nM to 10 µM. In some embodiments, the modulator is an agonist or a partial agonist with an $EC_{50}$ in said assay of less than a value selected from the interval of about 10 nM to 1 µM. In some embodiments, the modulator is an agonist or a partial agonist with an $EC_{50}$ in said assay of less than a value selected from the interval of about 10 nM to 100 nM.

In some embodiments, the modulator is an inverse agonist or an antagonist with an $IC_{50}$ of less than about 10 µM, of less than about 1 µM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 µM. In some embodiments, the modulator is an inverse agonist or an antagonist with an $IC_{50}$ of less than a value selected from the interval of about 10 nM to 1 µM. In some embodiments, the modulator is an inverse agonist or an antagonist with an $IC_{50}$ of less than a value selected from the interval of about 10 nM to 100 nM. In some embodiments, the modulator is an inverse agonist or an antagonist with an $IC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 µM, of less than about 1 µM, of less than about 100 nM, or of less than about 10 nM in said assay. In some embodiments, the modulator is an inverse agonist or an antagonist with an $IC_{50}$ in said assay of less than a value selected from the interval of about 10 nM to 10 µM. In some embodiments, the modulator is an inverse agonist or an antagonist with an $IC_{50}$ in said assay of less than a value selected from the interval of about 10 nM to 1 µM. In some embodiments, the modulator is an inverse agonist or an antagonist with an $IC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a fourth aspect, the invention features a method of preparing a pharmaceutical composition comprising admixing a modulator of a vertebrate GPR101 receptor and a pharmaceutically acceptable carrier. In some embodiments, the vertebrate is a mammal. In some embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator of the vertebrate GPR101 receptor is an agonist, a partial agonist, an inverse agonist, or an antagonist of the vertebrate GPR101 receptor. In certain embodiments, the modulator of the vertebrate GPR101 receptor is an agonist of the vertebrate GPR101 receptor. In certain embodiments, the modulator of the vertebrate GPR101 receptor is a partial agonist of the vertebrate GPR101 receptor. In certain embodiments, the modulator of the vertebrate GPR101 receptor is an inverse agonist of the vertebrate GPR101 receptor. In certain embodiments, the modulator of the vertebrate GPR101 receptor is an antagonist of the vertebrate GPR101 receptor.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an agonist or a partial agonist with an $EC_{50}$ of less than about 10 µM, of less than about 1 µM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 µM. In some embodiments, the modulator is an agonist or a partial agonist with an $EC_{50}$ of less than a value selected from the interval of about 10 nM to 1 µM. In some embodiments, the modulator is an agonist or a partial agonist with an $EC_{50}$ of less than a value selected from the interval of about 10 nM to 100 nM. In some embodiments, the modulator is an agonist or a partial agonist with an $EC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 µM, of less than about 1 µM, of less than about 100 nM, or of less than about 10 nM in said assay. In some embodiments, the modulator is an agonist or a partial agonist with an $EC_{50}$ in said assay of less than a value selected from the interval of about 10 nM to 10 µM. In some embodiments, the modulator is an agonist or a partial agonist with an $EC_{50}$ in said assay of less than a value selected from the interval of about 10 nM to 1 µM. In some embodiments, the modulator is an agonist or a partial agonist with an $EC_{50}$ in said assay of less than a value selected from the interval of about 10 nM to 100 nM.

In some embodiments, the modulator is an inverse agonist or an antagonist with an $IC_{50}$ of less than about 10 µM, of less than about 1 µM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 µM. In some embodiments, the modulator is an inverse agonist or an antagonist with an $IC_{50}$ of less than a value selected from the interval of about 10 nM to 1 µM. In some embodiments, the modulator is an inverse agonist or an antagonist with an $IC_{50}$ of less than a value selected from the interval of about 10 nM to 100 nM. In some embodiments, the modulator is an inverse agonist or an antagonist with an $IC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 µM, of less than about 1 µM, of less than about 100 nM, or of less than about 10 nM in said assay. In some embodiments, the modulator is an inverse agonist or an antagonist with an $IC_{50}$ in said assay of less than a value selected from the interval of about 10 nM to 10 µM. In some embodiments, the modulator is an inverse agonist or an antagonist with an $IC_{50}$ in said assay of less than a value selected from the interval of about 10 nM to 1 µM. In some embodiments, the modulator is an inverse agonist or an antagonist with an $IC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a fifth aspect, the invention features a method of increasing hypothalamic proopiomelanocortin (POMC)-derived biologically active peptide secretion comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of treating or preventing a POMC-derived biologically active peptide-related disorder ameliorated by increasing a level of secretion of the POMC-derived biologically active peptide comprising administering to a vertebrate in need thereof a therapeutically effective amount of a modulator of the vertebrate GPR101 or a pharmaceutical composition comprising the modulator and a pharmaceutically acceptable carrier. In certain embodiments, the level of secretion is a level of hypothalamic secretion.

The invention also relates to a method of treating or preventing obesity or a condition related thereto comprising administering to a vertebrate in need thereof a therapeutically effective amount of a modulator of the vertebrate GPR101 or a pharmaceutical composition comprising the modulator and a pharmaceutically acceptable carrier. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, non-alcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke. It is expressly contemplated that each individual condition related to obesity is a separate embodiment within the scope of the present invention.

The invention also relates to a method of promoting satiety comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

The invention also relates to a method of treating or preventing hyperphagia comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

The invention also relates to a method of treating or preventing pyrexia comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of treating or preventing an inflammation-associated disorder. In certain embodiments, the inflammation-associated disorder is selected from the group consisting of inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder. It is expressly contemplated that each individual inflammation-associated disorder is a separate embodiment within the scope of the present invention. In some embodiments, the brain inflammation-related disorder is selected from the group consisting of brain injury or trauma, multiple sclerosis, amyotrophic lateral sclerosis, Parkinson's disease, prion-associated disease, cerebral ischemia, AIDS dementia and Alzheimer's disease. It is expressly contemplated that each individual brain inflammation-related disorder is a separate embodiment within the scope of the present invention.

The invention also relates to a method of decreasing body mass comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

The invention also relates to a method of decreasing adiposity comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

The invention also relates to a method of decreasing percentage body fat comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

The invention also relates to a method of decreasing food intake comprising administering to a vertebrate in need thereof a therapeutically effective amount of a modulator of the vertebrate GPR101 or a pharmaceutical composition comprising the modulator and a pharmaceutically acceptable carrier. In certain embodiments, the vertebrate is obese. In certain embodiments, the vertebrate is overweight.

In certain embodiments, the vertebrate is a mammal. In certain embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator is an agonist. In some embodiments, the modulator is a partial agonist.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an agonist or a partial agonist with an $EC_{50}$ of less than about 10 µM, of less than about 1 µM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 µM. In some embodiments, the modulator is an agonist or a partial agonist with an $EC_{50}$ of less than a value selected from the interval of about 10 nM to 1 µM. In some embodiments, the modulator is an agonist or a partial agonist with an $EC_{50}$ of less than a value selected from the interval of about 10 nM to 100 in nM. In some embodiments, the modulator is an agonist or a partial agonist with an $EC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 µM, of less than about 1 µM, of less than about 100 nM, or of less than about 10 nM in said assay. In some embodiments, the modulator is an agonist or a partial agonist with an $EC_{50}$ in said assay of less than a value selected from the interval of about 10 nM to 10 µM. In some embodiments, the modulator is an agonist or a partial agonist with an $EC_{50}$ in said assay of less than a value selected from the interval of about 10 nM to 1 µM. In some embodiments, the modulator is an agonist or a partial agonist with an $EC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a sixth aspect, the invention features a method of decreasing hypothalamic proopiomelanocortin (POMC)-derived biologically active peptide secretion comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of treating or preventing a POMC-derived biologically active peptide-related disorder ameliorated by decreasing a level of secretion of the POMC-derived biologically active peptide comprising administering to a vertebrate in need thereof a therapeutically effective amount of a modulator of the vertebrate GPR101 or a pharmaceutical composition comprising the modulator and a pharmaceutically acceptable carrier. In certain embodiments, the level of secretion is a level of hypothalamic secretion.

The invention also relates to a method of treating or preventing a cachexia. In some embodiments, the cachexia is selected from the group consisting of AIDS-related weight loss, cancer-related weight loss and anorexia-related weight loss. It is expressly contemplated that AIDS-related weight loss, cancer-related weight loss and anorexia-related weight loss are separate embodiments within the scope of the present invention.

The invention also relates to a method of increasing body mass comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of increasing adiposity comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of increasing percentage body fat comprising administering to a vertebrate in need thereof a therapeutically effective amount of a modulator of the vertebrate GPR101 or a pharmaceutical composition comprising the modulator and a pharmaceutically acceptable carrier.

The invention also relates to a method of increasing food intake comprising administering to a vertebrate in need thereof a therapeutically effective amount of a modulator of the vertebrate GPR101 or a pharmaceutical composition comprising the modulator and a pharmaceutically acceptable carrier.

In certain embodiments, the vertebrate is a mammal. In certain embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator is an inverse agonist. In some embodiments, the modulator is an antagonist.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an inverse agonist or an antagonist with an $IC_{50}$ of less than about 10 µM, of less than about 1 µM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 µM. In some embodiments, the modulator is an inverse agonist or an antagonist with an $IC_{50}$ of less than a value selected from the interval of about 10 nM to 1 µM. In some embodiments, the modulator is an inverse agonist or an antagonist with an $IC_{50}$ of less than a value selected from the interval of about 10 nM to 100 nM. In some embodiments, the modulator is an inverse agonist or an antagonist with an $IC_{50}$ of less than about 10 µM, of less than about 1 µM, of less than about 100 nM, or of less than about 110 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 µM, of less than about 1 µM, of less than about 100 nM, or of less than about 10 nM in said assay. In some embodiments, the modulator is an inverse agonist or an antagonist with an $IC_{50}$ in said assay of less than a value selected from the interval of about 10 nM to 10 µM. In some embodiments, the modulator is an inverse agonist or an antagonist with an $IC_{50}$ in said assay of less than a value selected from the interval of about 10 nM to 1 µM. In some embodiments, the modulator is an inverse agonist or an antagonist with an $IC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a seventh aspect, the invention features use of a modulator of a vertebrate GPR101 in the manufacture of a medicament for increasing proopiomelanocortin (POMC)-derived biologically active peptide secretion. In some embodiments, the invention features use of a modulator of a vertebrate GPR101 in the manufacture of a medicament for increasing proopiomelanocortin (POMC)-derived biologically active peptide secretion in the vertebrate.

The invention also relates to use of a modulator of a vertebrate GPR101 in the manufacture of a medicament for treating or preventing a POMC-derived biologically active peptide-related disorder ameliorated by increasing a level of secretion of the POMC-derived biologically active peptide. In some embodiments, the invention relates to use of a modulator of a vertebrate GPR101 in the manufacture of a medicament for treating or preventing a POMC-derived biologically active peptide-related disorder ameliorated by increasing a level of secretion of the POMC-derived biologically active peptide in the vertebrate. In certain embodiments, the level of secretion is a level of hypothalamic secretion.

The invention also relates to use of a modulator of a vertebrate GPR101 in the manufacture of a medicament for treating or preventing obesity or a condition related thereto. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke. It is expressly contemplated that each individual condition related to obesity is a separate embodiment within the scope of the present invention. In some embodiments, the invention relates to use of a modulator of a vertebrate GPR101 in the manufacture of a medicament for treating or preventing obesity or a condition related thereto in the vertebrate.

The invention also relates to use of a modulator of a vertebrate GPR101 in the manufacture of a medicament for promoting satiety. In some embodiments, the invention relates to use of a modulator of a vertebrate GPR101 in the manufacture of a medicament for promoting satiety in the vertebrate.

The invention also relates to use of a modulator of a vertebrate GPR101 in the manufacture of a medicament for treating or preventing hyperphagia. In some embodiments, the invention relates to use of a modulator of a vertebrate GPR101 in the manufacture of a medicament for treating or preventing hyperphagia in the vertebrate.

The invention also relates to use of a modulator of a vertebrate GPR101 in the manufacture of a medicament for treating or preventing pyrexia. In some embodiments, the invention relates to use of a modulator of a vertebrate GPR101 in the manufacture of a medicament for treating or preventing pyrexia in the vertebrate.

The invention also relates to use of a modulator of a vertebrate GPR101 in the manufacture of a medicament for treating or preventing an inflammation-associated disorder. In certain embodiments, the inflammation-associated disorder is selected from the group consisting of inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder. It is expressly contemplated that each individual inflammation-associated disorder is a separate embodiment within the scope of the present invention. In some embodiments, the brain inflammation-related disorder is selected from the group consisting of brain injury or trauma, multiple sclerosis, amyotrophic lateral sclerosis, Parkinson's disease, prion-associated disease, cerebral ischemia, AIDS dementia and Alzheimer's disease. It is expressly contemplated that each individual brain inflammation-related disorder is a separate embodiment within the scope of the present invention. In some embodiments, the invention also relates to use of a modulator of a vertebrate GPR101 in the manufacture of a medicament for treating or preventing an inflammation-associated disorder in the vertebrate.

The invention also relates to use of a modulator of a vertebrate GPR101 in the manufacture of a medicament for decreasing body mass. In some embodiments, the invention relates to use of a modulator of a vertebrate GPR101 in the manufacture of a medicament for decreasing body mass in the vertebrate.

The invention also relates to use of a modulator of a vertebrate GPR101 in the manufacture of a medicament for decreasing adiposity. In some embodiments, the invention relates to use of a modulator of a vertebrate GPR101 in the manufacture of a medicament for decreasing adiposity in the vertebrate.

The invention also relates to use of a modulator of a vertebrate GPR101 in the manufacture of a medicament for decreasing percentage body fat. In some embodiments, the invention relates to use of a modulator of a vertebrate GPR101 in the manufacture of a medicament for decreasing percentage body fat in the vertebrate.

The invention also relates to use of a modulator of a vertebrate GPR101 in the manufacture of a medicament for decreasing food intake. In some embodiments, the invention relates to use of a modulator of a vertebrate GPR101 in the manufacture of a medicament for decreasing food intake in the vertebrate.

In certain embodiments, the vertebrate is a mammal. In certain embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator is an agonist. In some embodiments, the modulator is a partial agonist.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an agonist or a partial agonist with an $EC_{50}$ of less than about 10 μM, of less than about 1 μM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 μM. In some embodiments, the modulator is an agonist or a partial agonist with an $EC_{50}$ of less than a value selected from the interval of about 10 nM to 1 μM. In some embodiments, the modulator is an agonist or a partial agonist with an $EC_{50}$ of less than a value selected from the interval of about 10 nM to 100 nM. In some embodiments, the modulator is an agonist or a partial agonist with an $EC_{50}$ of less than about 10 μM, of less than about 1

µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 µM, of less than about 1 µM, of less than about 100 nM, or of less than about 10 nM in said assay. In some embodiments, the modulator is an agonist or a partial agonist with an $EC_{50}$ in said assay of less than a value selected from the interval of about 10 nM to 10 µM. In some embodiments, the modulator is an agonist or a partial agonist with an $EC_{50}$ in said assay of less than a value selected from the interval of about 10 nM to 1 µM. In some embodiments, the modulator is an agonist or a partial agonist with an $EC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In an eighth aspect, the invention features use of a modulator of a vertebrate GPR101 in the manufacture of a medicament for decreasing proopiomelanocortin (POMC)-derived biologically active peptide secretion. In some embodiments, the invention features use of a modulator of a vertebrate GPR101 in the manufacture of a medicament for decreasing proopiomelanocortin (POMC)-derived biologically active peptide secretion in the vertebrate.

The invention also relates to use of a modulator of a vertebrate GPR101 in the manufacture of a medicament for treating or preventing a POMC-derived biologically active peptide-related disorder ameliorated by decreasing a level of secretion of the POMC-derived biologically active peptide. In some embodiments, the invention relates to use of a modulator of a vertebrate GPR101 in the manufacture of a medicament for treating or preventing a POMC-derived biologically active peptide-related disorder ameliorated by decreasing a level of secretion of the POMC-derived biologically active peptide in the vertebrate. In certain embodiments, the level of secretion is a level of hypothalamic secretion.

The invention also relates to use of a modulator of a vertebrate GPR101 in the manufacture of a medicament for treating or preventing a cachexia. In some embodiments, the cachexia is selected from the group consisting of AIDS-related weight loss, cancer-related weight loss and anorexia-related weight loss. It is expressly contemplated that AIDS-related weight loss, cancer-related weight loss and anorexia-related weight loss are separate embodiments within the scope of the present invention. In some embodiments, the invention relates to use of a modulator of a vertebrate GPR101 in the manufacture of a medicament for treating or preventing a cachexia in the vertebrate.

The invention also relates to use of a modulator of a vertebrate GPR101 in the manufacture of a medicament for increasing body mass. In some embodiments, the invention relates to use of a modulator of a vertebrate GPR101 in the manufacture of a medicament for increasing body mass in the vertebrate.

The invention also relates to use of a modulator of a vertebrate GPR101 in the manufacture of a medicament for increasing adiposity. In some embodiments, the invention relates to use of a modulator of a vertebrate GPR101 in the manufacture of a medicament for increasing adiposity in the vertebrate.

The invention also relates to use of a modulator of a vertebrate GPR101 in the manufacture of a medicament for increasing percentage body fat. In some embodiments, the invention relates to use of a modulator of a vertebrate GPR101 in the manufacture of a medicament for increasing percentage body fat in the vertebrate.

The invention also relates to use of a modulator of a vertebrate GPR101 in the manufacture of a medicament for increasing food intake. In some embodiments, the invention relates to use of a modulator of a vertebrate GPR101 in the manufacture of a medicament for increasing food intake in the vertebrate.

In certain embodiments, the vertebrate is a mammal. In certain embodiments, the vertebrate is a human. In some embodiments, the modulator of the human GPR101 receptor is a modulator of human GPR101 having the amino acid sequence of SEQ ID NO: 2.

In some embodiments, the modulator is according to the second aspect.

In certain embodiments, the modulator is an inverse agonist. In some embodiments, the modulator is an antagonist.

In certain embodiments, the modulator is a small molecule. In some embodiments, the modulator is a small molecule with the proviso that the small molecule is not a polypeptide, an antibody or an antigen-binding fragment thereof, or a lipid. In some embodiments, the modulator is a small molecule with the proviso that the small molecule is not a polypeptide. In some embodiments, the modulator is a small molecule with the proviso that the small molecule is not an antibody or an antigen-binding fragment thereof. In some embodiments, the modulator is a small molecule with the proviso that the small molecule is not a lipid.

In some embodiments, the modulator is an inverse agonist or an antagonist with an $IC_{50}$ of less than about 10 µM, of less than about 1 µM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 µM. In some embodiments, the modulator is an inverse agonist or an antagonist with an $IC_{50}$ of less than a value selected from the interval of about 10 nM to 1 µM. In some embodiments, the modulator is an inverse agonist or an antagonist with an $IC_{50}$ of less than a value selected from the interval of about 10 nM to 100 nM. In some embodiments, the modulator is an inverse agonist or an antagonist with an $IC_{50}$ of less than about 10 µM, of less than about 1 µM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 μM, of less than about 1 μM, of less than about 100 nM, or of less than about 10 nM in said assay. In some embodiments, the modulator is an inverse agonist or an antagonist with an $IC_{50}$ in said assay of less than a value selected from the interval of about 10 nM to 10 μM. In some embodiments, the modulator is an inverse agonist or an antagonist with an $IC_{50}$ in said assay of less than a value selected from the interval of about 10 nM to 1 μM. In some embodiments, the modulator is an inverse agonist or an antagonist with an $IC_{50}$ in said assay of less than a value selected from the interval of about 10 nM to 100 nM.

In one aspect of the present invention, the GPR101 modulator is a selective GPR101 modulator, wherein the selective GPR101 modulator has a selectivity for GPR101 over GPR161 receptor of at least about 10-fold, of at least about 100-fold or of at least about 1000-fold.

In certain embodiments, the modulator is orally active.

In certain embodiments, the modulator is able to cross the blood-brain barrier.

In a ninth aspect, the invention features a method of screening compounds to identify modulators of hypothalamic proopiomelanocortin (POMC)-derived biologically active peptide secretion, which is characterized by using a GPCR comprising an amino acid sequence selected from the group consisting of:
  (a) the amino acid sequence of SEQ ID NO: 2;
  (b) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
  (c) the amino acid sequence of SEQ ID NO: 4;
  (d) the amino acid sequence of SEQ ID NO:6;
  (e) the amino acid sequence of a G protein-coupled receptor encoded by a polynucleotide hybridizing under stringent conditions to the complement of SEQ ID NO: 1, SEQ ID NO: 3 or SEQ ID NO: 5;
  (f) the amino acid sequence of a G protein-coupled receptor having an amino acid sequence having at least about 70% identity to SEQ ID NO: 2, SEQ ID NO: 4 or SEQ ID NO: 6;
  (g) the amino acid sequence of a G protein-coupled receptor having a variant of the amino acid sequence of SEQ ID NO: 2, SEQ ID NO: 4 or SEQ ID NO: 6; and
  (h) a biologically active fragment of any one of (a) to (g);
  comprising the steps:
  (a') contacting a candidate compound with said GPCR under conditions which permit interaction between said receptor and said candidate compound; and
  (b') detecting binding of the compound to said receptor.

In certain embodiments, the GPCR comprises the amino acid sequence of SEQ ID NO: 2 or the amino acid sequence of a G protein-coupled receptor having at least about 70% identity to SEQ ID NO: 2.

In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

The invention additionally features a method of identifying a candidate compound as a modulator of hypothalamic proopiomelanocortin (POMC)-derived biologically active peptide secretion, comprising steps (a') and (b') of this ninth aspect, and further comprising:
  (c') optionally synthesizing a compound which binds to the receptor in step (b');
  (d') contacting a compound which binds to the receptor in step (b') in vitro with a cell that expresses a G protein-coupled receptor of the invention and is capable of secreting a POMC-derived biologically active peptide or with a vertebrate hypothalamic cell or with vertebrate hypothalamic tissue; and
  (e') determining whether the compound modulates secretion of a POMC-derived biologically active peptide from the cell that expresses a G protein-coupled receptor of the invention and is capable of secreting a POMC-derived biologically active peptide or from the vertebrate hypothalamic cell or from the vertebrate hypothalamic tissue;
wherein the ability of the candidate compound to modulate secretion of a POMC-derived biologically active peptide from the cell that expresses a G protein-coupled receptor of the invention and is capable of secreting a POMC-derived biologically active peptide or from the vertebrate hypothalamic cell or from the vertebrate hypothalamic tissue is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a') and (b') of this ninth aspect, and further comprising:
  (c') optionally synthesizing a compound which binds to the receptor in step (b');
  (d') administering a compound which binds to the receptor in step (b') to a vertebrate; and
  (e') determining whether the compound modulates secretion of a POMC-derived biologically active peptide in the vertebrate;
wherein the ability of the candidate compound to modulate secretion of a POMC-derived biologically active peptide in the vertebrate is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a') and (b') of this ninth aspect, and further comprising:
  (c') optionally synthesizing a compound which binds to the receptor in step (b');
  (d') contacting a compound which binds to the receptor in step (b') in vitro with a cell that expresses a G protein-coupled receptor of the invention and is capable of expressing POMC polypeptide or mRNA or with a vertebrate hypothalamic cell or with vertebrate hypothalamic tissue; and
  (e') determining whether the compound modulates expression of POMC polypeptide or mRNA in the cell that expresses a G protein-coupled receptor of the invention and is capable of secreting a POMC-derived biologically active peptide or in the vertebrate hypothalamic cell or in the vertebrate hypothalamic tissue;
wherein the ability of the candidate compound to modulate expression of POMC polypeptide or mRNA in the cell that expresses a G protein-coupled receptor of the invention and is capable of secreting a POMC-derived biologically active peptide or in the vertebrate hypothalamic cell or in the vertebrate hypothalamic tissue is indicative of the compound being a modulator of POMC-derived biologically active peptide secretion.

The invention additionally features a method of identifying a candidate compound as a modulator of hypothalamic proopiomelanocortin (POMC)-derived biologically active peptide secretion, comprising steps (a') and (b') of this ninth aspect, and further comprising:
- (c') optionally synthesizing a compound which binds to the receptor in step (b');
- (d') administering a compound which binds to the receptor in step (b') to a vertebrate; and
- (e') determining whether the compound modulates expression of POMC polypeptide or mRNA in the vertebrate;

wherein the ability of the candidate compound to modulate expression of POMC polypeptide or mRNA in the vertebrate is indicative of the compound being a modulator of POMC-derived biologically active peptide secretion.

In certain embodiments, the POMC-derived biologically active peptide of step (e') is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, the G protein-coupled receptor of the invention is a G protein-coupled receptor having the amino acid sequence of SEQ ID NO: 2 or an endogenous or non-endogenous G protein-coupled receptor having an amino acid sequence having at least about 70% identity to SEQ ID NO: 2.

In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is a hypothalamic cell, a pituitary cell, a skin cell or a leukocyte. In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is an immortalized cell. In certain embodiments, the cell that expresses a G protein-coupled receptor of the invention and is capable of secreting a POMC-derived biologically active peptide or the cell that expresses a G protein-coupled receptor of the invention and is capable of expressing POMC polypeptide or mRNA is not an immortalized cell.

In certain embodiments, said determining whether the compound modulates secretion of a POMC-derived biologically active peptide is carried out by a process comprising hypothalamic slice assay. In certain embodiments, said hypothalamic slice assay is rat hypothalamic slice assay. In certain embodiments, said hypothalamic slice comprises a POMC neuron. In certain embodiments, said hypothalamic slice comprises a POMC neuron comprising GPR101.

In certain embodiments, the vertebrate hypothalamic tissue is mammalian hypothalamic tissue. In certain embodiments, the mammalian hypothalamic tissue is non-human mammalian hypothalamic tissue, such as but not limited to rat or mouse hypothalamic tissue. In certain embodiments, the vertebrate hypothalamic tissue is human hypothalamic tissue.

In certain embodiments, said determining whether the compound modulates expression of POMC mRNA in the vertebrate is carried out by a process comprising in situ hybridization histochemical analysis. In certain embodiments, said determining whether the compound modulates expression of POMC mRNA in the vertebrate is carried out by a process comprising in situ hybridization histochemical analysis of hypothalamic tissue. In certain embodiments, said determining whether the compound modulates expression of POMC mRNA in the vertebrate is carried out by a process comprising in situ hybridization histochemical analysis of hypothalamic tissue comprising hypothalamic arcuate nucleus tissue. In certain embodiments, said determining whether the compound modulates expression of POMC mRNA in the vertebrate is carried out by a process comprising in situ hybridization histochemical analysis carried out on serial sections prepared from hypothalamic tissue.

In certain embodiments, the screen is for a compound that stimulates hypothalamic proopiomelanocortin (POMC)-derived biologically active peptide secretion. In certain embodiments, the screen is for an agonist of the GPCR. In certain embodiments, the screen is for a partial agonist of the GPCR.

In certain embodiments, the screen is for a compound that inhibits hypothalamic proopiomelanocortin (POMC)-derived biologically active peptide secretion. In certain embodiments, the screen is for an inverse agonist of the GPCR. In certain embodiments, the screen is for an antagonist of the GPCR.

In certain embodiments, said receptor is recombinant.

In certain embodiments, said contacting comprises contacting the candidate compound with a host cell or with membrane of a host cell comprising recombinant said receptor. In some embodiments, said host cell comprises an expression vector comprising a polynucleotide encoding the receptor. In certain embodiments, the host cell is a eukaryotic cell. In some embodiments, the eukaryotic cell is a yeast cell. In some embodiments, the eukaryotic cell is a melanophore cell. In some embodiments, the eukaryotic cell is a mammalian host cell. In some embodiments, the mammalian cell is an HEK-293 cell, a COS-7 cell or a CHO cell.

In some embodiments, said determining is carried out with membrane comprising the GPCR.

In some embodiments, the candidate compound is not a compound known to be a ligand of a vertebrate GPR101 receptor. In some embodiments, the candidate compound is not a compound known to be an agonist, a partial agonist, an inverse agonist or an antagonist at a vertebrate GPR101 receptor. In some embodiments, the vertebrate is a mammal. In some embodiments, the vertebrate is a human.

In certain embodiments, the candidate compound is a small molecule. In some embodiments, the candidate compound is a small molecule with the proviso that the small molecule is not a polypeptide, an antibody or an antigen-binding fragment thereof, or a lipid. In some embodiments, the candidate compound is a small molecule with the proviso that the small molecule is not a polypeptide. In some embodiments, the candidate compound is a small molecule with the proviso that the small molecule is not an antibody or an antigen-binding fragment thereof. In some embodiments, the candidate compound is a small molecule with the proviso that the small molecule is not a lipid.

In certain embodiments, said method comprises determining whether the candidate compound is an agonist of the receptor. In certain embodiments, said method comprises determining whether the candidate compound is a partial agonist of the receptor. In certain embodiments, said method comprises determining whether the candidate compound is an inverse agonist of the receptor. In certain embodiments, said method comprises determining whether the candidate compound is an antagonist of the receptor.

In some embodiments, said method further comprises the step of formulating the modulator into a pharmaceutical composition. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises synthesis of the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises: optionally, determining the structure of the modulator; and providing the modulator or the name or structure of the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In some embodiments, said method further comprises: optionally, determining the structure of the modulator; optionally, providing the modulator or the name or structure of the modulator; and producing or synthesizing the modulator. In some embodiments, the modulator is an agonist of the GPCR. In some embodiments, the modulator is a partial agonist of the GPCR. In some embodiments, the modulator is an inverse agonist of the GPCR. In some embodiments, the modulator is an antagonist of the GPCR.

In a tenth aspect, the invention features a method of identifying a candidate compound as a ligand of a GPCR comprising an amino acid sequence selected from the group consisting of:
  (a) the amino acid sequence of SEQ ID NO: 2;
  (b) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
  (c) the amino acid sequence of SEQ ID NO: 4;
  (d) the amino acid sequence of SEQ ID NO:6;
  (e) the amino acid sequence of a G protein-coupled receptor encoded by a polynucleotide hybridizing under stringent conditions to the complement of SEQ ID NO: 1, SEQ ID NO: 3 or SEQ ID NO: 5;
  (f) the amino acid sequence of a G protein-coupled receptor having an amino acid sequence having at least about 70% identity to SEQ ID NO: 2, SEQ ID NO: 4 or SEQ ID NO: 6;
  (g) the amino acid sequence of a G protein-coupled receptor having a variant of the amino acid sequence of SEQ ID NO: 2, SEQ ID NO: 4 or SEQ ID NO: 6; and
  (h) a biologically active fragment of any one of (a) to (g);
comprising the steps of:
  (a') contacting said GPCR with an optionally labeled known ligand to the GPCR in the presence or absence of the candidate compound;
  (b') detecting the complex between the known ligand and said GPCR; and
  (c') determining whether less of said complex is formed in the presence of the candidate compound than in the absence of the candidate compound;
wherein said determination is indicative of the candidate compound being a ligand of said receptor. The invention also features a method of screening candidate compounds as pharmaceutical agents for a POMC-derived biologically active peptide-related disorder, said method comprising:
  (a) contacting a candidate compound with a GPCR, under conditions which permit interaction between said receptor and said candidate compound, wherein said receptor comprises an amino acid sequence selected from the group consisting of:
    (i) the amino acid sequence of SEQ ID NO: 2;
    (ii) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
    (iii) the amino acid sequence of SEQ ID NO: 4;
    (iv) the amino acid sequence of SEQ ID NO:6;
    (v) the amino acid sequence of a G protein-coupled receptor encoded by a polynucleotide hybridizing under stringent conditions to the complement of SEQ ID NO: 1, SEQ ID NO: 3 or SEQ ID NO: 5;
    (vi) the amino acid sequence of a G protein-coupled receptor having an amino acid sequence having at least about 70% identity to SEQ ID NO: 2, SEQ ID NO: 4 or SEQ ID NO: 6;
    (vii) the amino acid sequence of a G protein-coupled receptor having a variant of the amino acid sequence of SEQ ID NO: 2, SEQ ID NO: 4 or SEQ ID NO: 6; and
    (viii) a biologically active fragment of any one of (i) to (vii); and
  (b) detecting a ligand bound to said GPCR.

In certain embodiments, the GPCR comprises the amino acid sequence of SEQ ID NO: 2 or the amino acid sequence of a G protein-coupled receptor having at least about 70% identity to SEQ ID NO: 2.

In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, said receptor is recombinant.

In certain embodiments, said contacting comprises contacting the candidate compound with a host cell or with membrane of a host cell comprising recombinant said receptor. In some embodiments, said host cell comprises an expression vector comprising a polynucleotide encoding the receptor. In certain embodiments, the host cell is a eukaryotic cell. In some embodiments, the eukaryotic cell is a yeast cell. In some embodiments, the eukaryotic cell is a melanophore cell. In some embodiments, the eukaryotic cell is a mammalian host cell. In some embodiments, the mammalian cell is an HEK-293 cell, a COS-7 cell or a CHO cell.

In some embodiments, said determining is carried out with membrane comprising the GPCR.

In certain embodiments, the screen is for modulators of hypothalamic proopiomelanocortin (POMC)-derived biologically active peptide secretion. In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, the candidate compounds are screened as radioimaging agents for identifying a vertebrate at risk for or progressing toward obesity or a condition related thereto. In certain embodiments, a level of expression of GPR101 receptor in brain below a normal level is indicative of the vertebrate being at risk for or progressing toward obesity or a condition related thereto or being at risk for or progressing toward an inflammation-associated disorder. In certain embodiments, a level of expression of GPR101 receptor in hypothalamus below a normal level is indicative of the vertebrate being at risk for or progressing toward obesity or a condition related thereto. In certain embodiments, the vertebrate is a mammal. In certain embodiments, the vertebrate is a human.

In an eleventh aspect, the invention features use of a GPCR to screen candidate compounds as modulators of hypothalamic proopiomelanocortin (POMC)-derived biologically active peptide secretion, wherein the GPCR comprises an amino acid sequence selected from the group consisting of:
(a) the amino acid sequence of SEQ ID NO: 2;
(b) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
(c) the amino acid sequence of SEQ ID NO: 4;
(d) the amino acid sequence of SEQ ID NO:6;
(e) the amino acid sequence of a G protein-coupled receptor encoded by a polynucleotide hybridizing under stringent conditions to the complement of SEQ ID NO: 1, SEQ ID NO: 3 or SEQ ID NO: 5;
(f) the amino acid sequence of a G protein-coupled receptor having an amino acid sequence having at least about 70% identity to SEQ ID NO: 2, SEQ ID NO: 4 or SEQ ID NO: 6;
(g) the amino acid sequence of a G protein-coupled receptor having a variant of the amino acid sequence of SEQ ID NO: 2, SEQ ID NO: 4 or SEQ ID NO: 6; and
(h) a biologically active fragment of any one of (a) to (g).

In certain embodiments, the GPCR comprises the amino acid sequence of SEQ ID NO: 2 or the amino acid sequence of a G protein-coupled receptor having at least about 70% identity to SEQ ID NO: 2.

In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, the screen is for a compound that stimulates hypothalamic proopiomelanocortin (POMC)-derived biologically active peptide secretion. In certain embodiments, the screen is for an agonist of the GPCR. In certain embodiments, the screen is for a partial agonist of the GPCR.

In certain embodiments, the screen is for a pharmaceutical agent for obesity or a condition related thereto. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke. It is expressly contemplated that each individual condition related to obesity is a separate embodiment within the scope of the present invention. In certain embodiments, the screen is for an agonist of the GPCR. In certain embodiments, the screen is for a partial agonist of the GPCR.

In certain embodiments, the screen is for a pharmaceutical agent for promoting satiety. In certain embodiments, the screen is for an agonist of the GPCR. In certain embodiments, the screen is for a partial agonist of the GPCR.

In certain embodiments, the screen is for a pharmaceutical agent for hyperphagia. In certain embodiments, the screen is for an agonist of the GPCR. In certain embodiments, the screen is for a partial agonist of the GPCR.

In certain embodiments, the screen is for a pharmaceutical agent for pyrexia. In certain embodiments, the screen is for an agonist of the GPCR. In certain embodiments, the screen is for a partial agonist of the GPCR.

In certain embodiments, the screen is for a pharmaceutical agent for an inflammation-associated disorder. In certain embodiments, the inflammation-associated disorder is selected from the group consisting of inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder. It is expressly contemplated that each individual inflammation-associated disorder is a separate embodiment within the scope of the present invention. In some embodiments, the brain inflammation-related disorder is selected from the group consisting of brain injury or trauma, multiple sclerosis, amyotrophic lateral sclerosis, Parkinson's disease, prion-associated disease, cerebral ischemia, AIDS dementia and Alzheimer's disease. It is expressly contemplated that each individual brain inflammation-related disorder is a separate embodiment within the scope of the present invention. In certain embodiments, the screen is for an agonist of the GPCR. In certain embodiments, the screen is for a partial agonist of the GPCR.

In certain embodiments, the screen is for an agent that decreases an energy homeostasis-related parameter selected from the group consisting of body mass, adiposity, percentage body fat and food intake. In certain embodiments, the screen is for an agent that decreases body mass. In certain embodiments, the screen is for an agent that decreases adiposity. In certain embodiments, the screen is for an agent that decreases percentage body fat. In certain embodiments, the screen is for an agent that decreases food intake. In certain embodiments, the screen is for an agonist of the GPCR. In certain embodiments, the screen is for a partial agonist of the GPCR.

In certain embodiments, the screen comprises determining whether the modulator is an agonist of the GPCR. In certain embodiments, the screen comprises determining whether the modulator is a partial agonist of the GPCR.

In certain embodiments, the screen is for a compound that inhibits hypothalamic proopiomelanocortin (POMC)-derived biologically active peptide secretion. In certain embodiments, the screen is for an inverse agonist of the GPCR. In certain embodiments, the screen is for an antagonist of the GPCR.

In certain embodiments, the screen is for a pharmaceutical agent for a cachexia. In some embodiments, the cachexia is selected from the group consisting of AIDS-related weight loss, cancer-related weight loss and anorexia-related weight loss. It is expressly contemplated that AIDS-related weight loss, cancer-related weight loss and anorexia-related weight loss are separate embodiments within the scope of the present invention. In certain embodiments, the screen is for an inverse agonist of the GPCR. In certain embodiments, the screen is for an antagonist of the GPCR.

In certain embodiments, the screen is for an agent that increases an energy homeostasis-related parameter selected from the group consisting of body mass, adiposity, percentage body fat and food intake. In certain embodiments, the screen is for an agent that increases body mass. In certain embodiments, the screen is for an agent that increases adiposity. In certain embodiments, the screen is for an agent that increases percentage body fat. In certain embodiments, the screen is for an agent that increases food intake. In certain embodiments, the screen is for an inverse agonist of the GPCR. In certain embodiments, the screen is for an antagonist of the GPCR.

In certain embodiments, the screen comprises determining whether the modulator is an inverse agonist of the GPCR. In certain embodiments, the screen comprises determining whether the modulator is an antagonist of the GPCR.

The invention also relates to use of a GPCR to screen candidate compounds as pharmaceutical agents for a POMC-derived biologically active peptide-related disorder, wherein the GPCR comprises an amino acid sequence selected from the group consisting of:
  (a) the amino acid sequence of SEQ ID NO: 2;
  (b) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
  (c) the amino acid sequence of SEQ ID NO: 4;
  (d) the amino acid sequence of SEQ ID NO:6;
  (e) the amino acid sequence of a G protein-coupled receptor encoded by a polynucleotide hybridizing under stringent conditions to the complement of SEQ ID NO: 1, SEQ ID NO: 3 or SEQ ID NO: 5;
  (f) the amino acid sequence of a G protein-coupled receptor having an amino acid sequence having at least about 70% identity to SEQ ID NO: 2, SEQ ID NO: 4 or SEQ ID NO: 6;
  (g) the amino acid sequence of a G protein-coupled receptor having a variant of the amino acid sequence of SEQ ID NO: 2, SEQ ID NO: 4 or SEQ ID NO: 6; and
  (h) a biologically active fragment of any one of (a) to (g).

In certain embodiments, the GPCR comprises the amino acid sequence of SEQ ID NO: 2 or the amino acid sequence of a G protein-coupled receptor having at least about 70% identity to SEQ ID NO: 2.

In certain embodiments, the POMC-derived biologically active peptide is selected from the group consisting of ACTH, β-endorphin, α-MSH, β-MSH and γ-MSH. It is expressly contemplated that POMC-derived biologically active peptides may be included in embodiments of the invention individually or in any combination.

In certain embodiments, the POMC-derived biologically active peptide-related disorder is ameliorated by increasing a level of secretion of the POMC-derived biologically active peptide. In certain embodiments, the POMC-derived biologically active peptide-related disorder is ameliorated by decreasing a level of secretion of the POMC-derived biologically active peptide. In certain embodiments, the level of secretion is a level of hypothalamic secretion.

In certain embodiments, the screen is for a ligand of the GPCR.

Applicant reserves the right to exclude any one or more candidate compounds from any of the embodiments of the invention. Applicant reserves the right to exclude any one or more modulators from any of the embodiments of the invention. By way of example and not limitation, Applicant reserves the right to exclude any one or more agonists, partial agonists, inverse agonists or antagonists from any of the embodiments of the invention. Applicant reserves the right to exclude any polynucleotide or polypeptide from any of the embodiments of the invention. Applicant additionally reserves the right to exclude any condition related to obesity, any inflammation-associated disorder, any cachexia, or any parameter related to energy homeostasis from any of the embodiments of the invention. It is also expressly contemplated that conditions related to obesity of the invention can be included in an embodiment either individually or in any combination, that inflammation-associated disorders can be included in an embodiment either individually or in any combination, that cachexias can be included in an embodiment either individually or in any combination, and that parameters related to energy homeostasis can be included in an embodiment either individually or in any combination.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

Throughout this application, various publications, patents and published patent applications are cited. The disclosures of these publications, patents and published patent applications referenced in this application are herein incorporated by reference in their entirety into the present disclosure. Citation herein by Applicant of a publication, patent, or published patent application is not an admission by Applicant of said publication, patent, or published patent application as prior art.

This application claims the benefit of priority from the following provisional patent application, filed via U.S. Express mail with the United States Patent and Trademark Office on the indicated date: U.S. Provisional Patent Application No. 60/809,634, filed May 31, 2006. The disclosure of the foregoing provisional patent application is herein incorporated by reference in its entirety.

BRIEF DESCRIPTION OF THE DRAWINGS

FIG. 1 depicts results from a primary screen of candidate compounds against a "target receptor" which is a Gsα Fusion Protein construct of an endogenous, constitutively active Gs-coupled GPCR unrelated to GPR101. Results for "Compound A" are provided in well A2. Results for "Compound "B" are provided in well G9. (See, Example 6.)

DETAILED DESCRIPTION

Definitions

Figure 1:
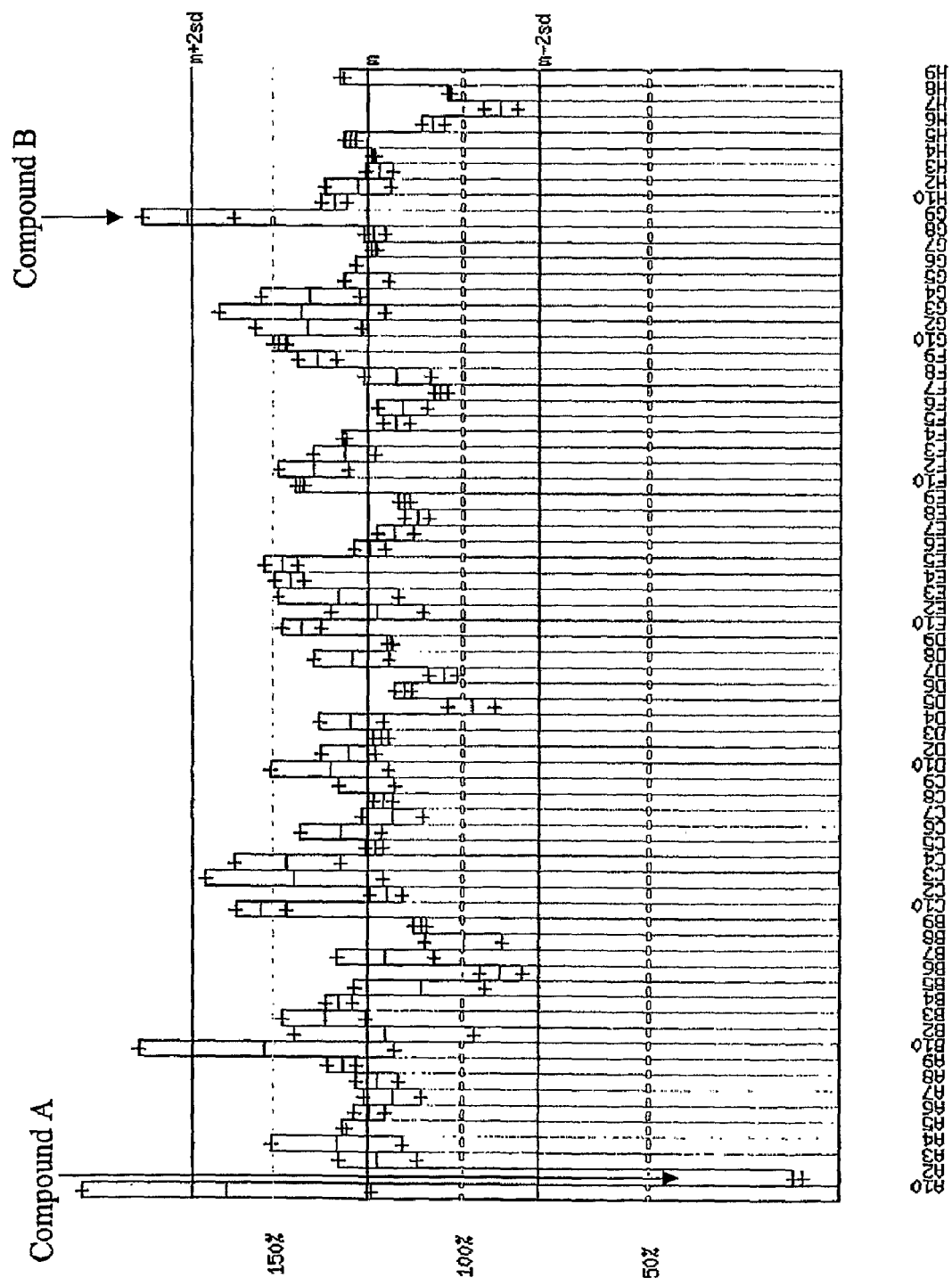
FIG. 1. By way of illustration and not limitation.

ADIPOSITY as used herein shall refer to body fat.

AGONIST shall mean an agent (e.g., ligand, candidate compound) that by virtue of binding to a GPCR activates the GPCR so as to elicit an intracellular response mediated by the GPCR.

ALZHEIMER'S DISEASE is a progressive neurodegenerative disease characterized by significant loss of function in more than one cognitive domain and often accompanied by changes in behavior or personality. Alzheimer's disease is the most common cause of dementia. In some embodiments, Alzheimer's disease encompasses mild cognitive impairment (MCI).

AMINO ACID ABBREVIATIONS used herein are set out in Table B:

TABLE B

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONIST shall mean an agent (e.g. ligand, candidate compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An antagonist typically does not diminish the baseline intracellular response in the absence of an agonist or partial agonist.

ANTIBODY is intended herein to encompass monoclonal antibody and polyclonal antibody. Antibodies of the present invention may be prepared by any suitable method known in the art.

BIOLOGICALLY ACTIVE FRAGMENT of a GPCR polypeptide or amino acid sequence shall mean a fragment of the polypeptide or amino acid sequence having structural and biochemical functions of a naturally occurring GPCR. In certain embodiments, the biologically active fragment couples to a G protein. In certain embodiments, the biologically active fragment binds to a ligand.

BRAIN INFLAMMATION-RELATED DISORDER is intended to include but not be limited to brain injury or trauma, multiple sclerosis, amyotrophic lateral sclerosis, Parkinson's disease, prion-associated disease, cerebral ischemia (e.g., ischemic stroke), AIDS dementia and Alzheimer's disease.

CACHEXIA shall mean a general weight loss and wasting occurring in the course of a chronic disease or emotional disturbance.

CANDIDATE COMPOUND shall mean a molecule (for example, and not limitation, a chemical compound) that is amenable to a screening technique and is used interchangeably herein with TEST COMPOUND.

CEREBRAL ISCHEMIA shall mean a deficiency of the blood supply to the brain caused by constriction or obstruction of the blood vessels.

CODON shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

COMPOSITION means a material comprising at least one component.

COMPOUND EFFICACY or EFFICACY shall mean a measurement of the ability of a compound to stimulate or inhibit G protein-coupled receptor functionality, as opposed to receptor binding affinity. Exemplary means of measuring compound efficacy are disclosed in the Examples section of this patent document.

CONDITION RELATED TO OBESITY is intended to include but not be limited to hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In some embodiments, the condition related to obesity is selected from the group consisting of hypertension, insulin resistance, metabolic syndrome, Type 2 diabetes, dyslipidemia, atherosclerosis, coronary heart disease, and stroke.

CONSTITUTIVELY ACTIVE RECEPTOR shall mean a receptor stabilized in an active state by means other than through binding of the receptor to its ligand or a chemical equivalent thereof. A constitutively active receptor may be endogenous or non-endogenous.

CONSTITUTIVELY ACTIVATED RECEPTOR shall mean an endogenous receptor that has been modified so as to be constitutively active or to be more constitutively active.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound" or "test compound", shall mean the screening of a compound against a G protein-coupled receptor in the absence of a known ligand (e.g., a known agonist) to the G protein-coupled receptor.

DYSLIPIDEMIA as used herein refers to abnormal concentrations of serum lipids such as HDL (low), LDL (high), VLDL (high), triglycerides (high), lipoprotein (a) (high), free fatty acids (high) and other serum lipids, or combinations thereof.

ENDOGENOUS shall mean a material that a vertebrate (for example, and not limitation, a mammal or a human) naturally produces. Endogenous in reference to, for example and not limitation, the term "receptor," shall mean that which is naturally produced by a vertebrate (for example, and not limitation, a mammal or a human). Endogenous shall be understood to encompass allelic variants of a gene as well as the allelic polypeptide variants so encoded. As used herein, "endogenous GPCR" and "native GPCR" are used interchangeably. By contrast, the term NON-ENDOGENOUS in this context shall mean that which is not naturally produced by a vertebrate (for example, and not limitation, a mammal or a human).

EXPRESSION VECTOR shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

G PROTEIN-COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous GPCR. In the preferred form, the G protein can be fused directly to the C-terminus of the GPCR or there may be spacers between the two.

HOST CELL shall mean a cell capable of having a vector incorporated therein. In the present context, the vector will typically contain nucleic acid encoding a GPCR or GPCR fusion protein in operable connection with a suitable promoter sequence to permit expression of the GPCR or GPCR fusion protein to occur.

IMPAIRED GLUCOSE TOLERANCE (IGT) as used herein is intended to indicate that condition associated with insulin-resistance that is intermediate between frank, type 2 diabetes and normal glucose tolerance (NGT). IGT is diagnosed by a procedure wherein an affected person's postprandial glucose response is determined to be abnormal as assessed by 2-hour postprandial plasma glucose levels. In this test, a measured amount of glucose is given to the patient and blood glucose levels are measured at regular intervals, usually every half hour for the first two hours and every hour thereafter. In a "normal" or non-IGT subject, glucose levels rise during the first two hours to a level less than 140 mg/dl and then drop rapidly. In an IGT subject, the blood glucose levels are higher and the drop-off level is at a slower rate.

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that a subject or animal requires or will benefit from treatment. This judgement is made based on a variety of factors that are in the realm of a caregiver's expertise, but that include the knowledge that the subject or animal is ill, or will be ill, as the result of a condition that is treatable by the compounds of the invention.

INFLAMMATION-ASSOCIATED DISORDER is intended to include but not be limited to inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder.

INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) subjects have insulin resistance. A diagnosis of insulin resistance can also be made using the euglycemic glucose clamp test.

INVERSE AGONIST shall mean an agent (e.g., ligand, candidate compound) which binds to a GPCR and which inhibits the baseline intracellular response initiated by the active form of the receptor below the normal base level activity which is observed in the absence of an agonist or partial agonist.

LIGAND as used herein shall mean a molecule that specifically binds to a GPCR. An endogenous ligand is an endogenous molecule that binds to a native GPCR. A ligand of a GPCR may be, but is not limited to, an agonist, a partial agonist, an inverse agonist or an antagonist of the GPCR.

METABOLIC SYNDROME as defined herein, and according to the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670), occurs when a person meets three or more of five criteria related to obesity, hypertriglyceridemia, low HDL cholesterol, high blood pressure, and high fasting glucose.

As used herein, the terms MODULATE or MODIFY are meant to refer to an increase or decrease in the amount, quality, or effect of a particular activity, function or molecule.

MODULATOR shall be understood to encompass agonist, partial agonist, inverse agonist and antagonist as hereinbefore defined.

OBESITY, as used herein, is defined as a body-mass index (BMI) of 30.0 or greater, in accordance with the WHO classifications of weight (Kopelman, Nature (2000) 404:635-643; the disclosure of which is herein incorporated by reference in its entirety). In certain embodiments, obesity is defined on the basis of body fat content: greater than 25% in males and greater than 30% in females.

OVERWEIGHT, as used herein, is defined as a body mass index (BMI) of 27-29.9.

PARKINSON'S DISEASE is a chronic, progressive neurodegenerative disorder characterized by motor symptoms such as tremor, bradykinesia, muscle rigidity, gait dysfunction, and postural instability. Researchers have identified degeneration of dopaminergic neurons in the substantia nigra as the primary pathophysiological mechanism.

PARTIAL AGONIST shall mean an agent (e.g., ligand, candidate compound) that by virtue of binding to a GPCR activates the GPCR so as to elicit an intracellular response mediated by the GPCR, albeit to a lesser extent or degree than does a full agonist.

PHARMACEUTICAL COMPOSITION shall mean a composition comprising at least one active ingredient, whereby the composition is amenable to investigation for a specified, efficacious outcome in a mammal (for example, and not limited to a human). Those of ordinary skill in the art will understand and appreciate the techniques appropriate for determining whether an active ingredient has a desired efficacious outcome e.g., based upon the needs of the artisan.

POLYNUCLEOTIDE shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, PEPTIDES, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

As used herein, POMC-DERIVED BIOLOGICALLY ACTIVE PEPTIDE shall refer to a peptide derived from POMC, such as by a process comprising proteolytic cleavage of POMC, capable of stimulating or inhibiting a biological activity. By way of illustration and not limitation, said biological activity may be activation of a GPCR.

As used herein, POMC-DERIVED BIOLOGICALLY ACTIVE PEPTIDE-RELATED DISORDER shall refer to disorders that are ameliorated by either increasing or decreasing a level of secretion of a POMC-derived biologically active peptide, wherein said level of secretion is intended to encompass but not necessarily be limited to a level of hypothalamic secretion.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

SECOND MESSENGER shall mean an intracellular response produced as a result of receptor activation. A second messenger can include, for example, inositol 1,4,5-triphosphate ($IP_3$), diacylglycerol (DAG), cyclic AMP (cAMP), cyclic GMP (cGMP), MAP kinase activity, MAPK/ERK kinase kinase-1 (MEKK1) activity, and $Ca^{2+}$. Second messenger response can be measured for a determination of receptor activation. In addition, second messenger response can be measured for the identification of candidate compounds as, for example, inverse agonists, partial agonists, agonists, and antagonists of the receptor.

SELECTIVE GPR101 LIGAND, as used herein, refers to a ligand of GPR101 having selectivity for GPR101 receptor over one or more closely related receptors, such as GPR161 (also known as RE2 receptor; see, e.g., GenBank® Accession No. CAI22624 for human GPR161).

SELECTIVE GPR101 MODULATOR, as used herein, refers to a modulator of GPR101 having selectivity for GPR101 receptor over one or more closely related receptors, such as GPR161 (also known as RE2 receptor; see, e.g., GenBank® Accession No. CAI22624 for human GPR161). By way of illustration and not limitation, a selective GPR101 modulator may be a selective GPR101 agonist, partial agonist, inverse agonist or antagonist.

SMALL MOLECULE shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 500 grams per mole.

STIMULATE or STIMULATING, in relationship to the term "response" shall mean that a response is increased in the presence of a compound as opposed to in the absence of the compound.

STROKE is a cardiovascular disease that affects the blood vessels supplying blood to the brain and is intended herein to include cerebral thrombosis, the most common type of STROKE. Cerebral thrombosis occurs when a blood clot (thrombus) forms and blocks blood flow in an artery bringing blood to part of the brain. Blood clots usually form in arteries damaged by atherosclerosis.

As used herein, SUBJECT is preferably a vertebrate, including but not limited to fish (such as commercially farmed fish, pet fish, etc.), amphibians (such as frogs, toads, pet amphibians, etc.), reptiles (such as snakes, lizards, turtles, pet reptiles, etc.), birds (such as chickens, turkeys, pet birds, etc.) and mammals (such as mice, rats, hamsters, rabbits, pigs, dogs, cats, horses, cows, sheep, goats, non-human primates (such as rhesus monkeys and chimpanzees), non-human mammals, pet non-human mammals, humans, etc.). In certain embodiments, the subject is a mouse, a rat, a hamster, a rabbit, a pig, a dog, a cat, a horse, a cow, a sheep, a goat, a non-human primate or a human (which may be included in embodiments of the invention individually or in any combination). In certain embodiments, the subject is a human companion animal (such as a dog, a cat, etc.), a farm animal (such as a cow, a sheep, a goat, a pig, a chicken, etc.), a sports animal (such as a horse, a dog, etc.), a beast of burden (such as a mule, a camel, etc.) or an exotic animal (such as an animal found in a zoo, etc.), which may be included in embodiments of the invention individually or in any combination. In certain embodiments, the subject is a mammal. In certain embodiments, the subject is a non-human mammal. In certain embodiments, the subject is a human.

THERAPEUTICALLY EFFECTIVE AMOUNT as used herein refers to the amount of active compound or pharmaceutical agent that elicits the biological or medicinal response in a tissue, system, animal, subject or human that is being sought by a researcher, veterinarian, medical doctor or other clinician, which includes one or more of the following:

(1) Preventing the disease; for example, preventing a disease, condition or disorder in a subject that may be predisposed to the disease, condition or disorder but does not yet experience or display the pathology or symptomatology of the disease, (2) Inhibiting the disease; for example, inhibiting a disease, condition or disorder in a subject that is experiencing or displaying the pathology or symptomatology of the disease, condition or disorder (i.e., arresting further development of the pathology and/or symptomatology), and (3) Ameliorating the disease; for example, ameliorating a disease, condition or disorder in a subject that is experiencing or displaying the pathology or symptomatology of the disease, condition or disorder (i.e., reversing the pathology and/or symptomatology).

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differ in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

A. Introduction

The order of the following sections is set forth for presentational efficiency and is not intended, nor should be construed, as a limitation on the disclosure or the claims to follow.

B. Receptor Expression

1. GPCR Polypeptides of Interest

A GPCR of the invention may comprise an amino acid sequence selected from the group consisting of:
  (a) the amino acid sequence of SEQ ID NO: 2;
  (b) the amino acid sequence of a G protein-coupled receptor encoded by a polynucleotide that is amplifiable by polymerase chain reaction (PCR) on a human DNA sample using specific primers SEQ ID NO: 7 and SEQ ID NO: 8;
  (c) the amino acid sequence of SEQ ID NO: 4;
  (d) the amino acid sequence of SEQ ID NO: 6;
  (e) the amino acid sequence of a G protein-coupled receptor encoded by a polynucleotide hybridizing under stringent conditions to the complement of SEQ ID NO: 1, SEQ ID NO: 3 or SEQ ID NO: 5;
  (f) the amino acid sequence of a G protein-coupled receptor having an amino acid sequence having at least about 70% identity to SEQ ID NO: 2, SEQ ID NO:4 or SEQ ID NO: 6;
  (g) the amino acid sequence of a G protein-coupled receptor having a variant of the amino acid sequence of SEQ ID NO: 2, SEQ ID NO: 4 or SEQ ID NO: 6; and
  (h) a biologically active fragment of any one of any one of (a) to (g).

In certain embodiments, a GPCR of the invention comprises the amino acid sequence of SEQ ID NO: 2.

In certain embodiments, the G protein-coupled receptor encoded by the polynucleotide that is amplifiable by polymerase chain reaction is an endogenous G protein-coupled receptor. In some embodiments, the G protein-coupled receptor encoded by the polynucleotide that is amplifiable by polymerase chain reaction and that is an endogenous G protein-coupled receptor is a human G protein-coupled receptor. In some embodiments, the G protein-coupled receptor encoded by the polynucleotide that is amplifiable by polymerase chain reaction and that is an endogenous G protein-coupled receptor is a human GPR101 receptor. In certain embodiments, the G protein-coupled receptor encoded by the polynucleotide that is amplifiable by polymerase chain reaction is SEQ ID NO:2 or an allele thereof. In certain embodiments, the G protein-coupled receptor encoded by a polynucleotide that is amplifiable by polymerase chain reaction is an allele of SEQ ID NO:2. In some embodiments, the G protein-coupled receptor encoded by the polynucleotide that is amplifiable by polymerase chain reaction exhibits a detectable level of constitutive activity. In some embodiments, the constitutive activity is for increasing a level of intracellular cAMP consistent with the G protein-coupled receptor being coupled to Gs. In some embodiments, the constitutive activity is for causing melanophore cells to undergo pigment dispersion. In some embodiments, the G protein-coupled receptor encoded by the polynucleotide that is amplifiable by polymerase chain reaction couples to Gs.

In some embodiments, the human DNA is genomic DNA.

In some embodiments, the polymerase chain reaction is reverse transcription-polymerase chain reaction (RT-PCR). RT-PCR techniques are well known to the skilled artisan. In some embodiments, the human DNA is human cDNA derived from a tissue or cell that expresses GPR101. In some embodiments, the human tissue that expresses GPR101 is brain or hypothalamus. In certain embodiments, the cDNA is from a human cell that expresses GPR101. In some embodiments, the cDNA is from a POMC neuronal cell. In some embodiments, the cell is a cell line.

In some embodiments, a GPCR of the invention is recombinant. In some embodiments, the recombinant GPCR is recombinant human GPR101.

In certain embodiments, a GPCR that may be used in the subject methods exhibits a detectable level of constitutive activity. In some embodiments, the constitutive activity is for increasing a level of intracellular cAMP consistent with the GPCR being coupled to Gs. In some embodiments, the constitutive activity is for causing melanophore cells to undergo pigment dispersion. In some embodiments, the GPCR couples to Gs.

In some embodiments, a GPCR of the invention is endogenous. In some embodiments, a GPCR of the invention is a mammalian GPR101. In some embodiments, a GPCR of the invention that is endogenous is a mammalian GPR101. In some embodiments, a GPCR of the invention that is endogenous is a human GPR101.

In some embodiments, a GPCR of the invention is non-endogenous.

By way of illustration and not limitation, deletion of an N-terminal methionine residue is envisioned to provide a biologically active fragment that may be used in the subject invention. By way of illustration and not limitation, amino acids 2-508 of SEQ ID NO: 2, amino acids 2-511 of SEQ ID NO: 4 and amino acids 2-508 of SEQ ID NO: 6 are expressly contemplated to be biologically active fragments within the scope of the invention. In some embodiments, a biologically active fragment of the invention is a fragment optionally fused at its N-terminus to a peptide comprising an N-terminal methionine residue and an HA epitope tag that exhibits a detectable level of constitutive activity. In some embodiments, the constitutive activity is for increasing a level of intracellular cAMP consistent with the biologically active fragment being coupled to Gs. In some embodiments, the constitutive activity is for causing melanophore cells to undergo pigment dispersion. In some embodiments, a biologically active fragment of the invention is a fragment optionally fused at its N-terminus to a peptide comprising an N-terminal methionine residue and an HA epitope tag couples to Gs. In certain embodiments, the fragment is fused at its N-terminus to a peptide consisting essentially of an N-terminal methionine residue and an HA epitope tag. Techniques for fusing a peptide comprising or consisting essentially of an N-terminal methionine residue and an HA epitope tag to the N-terminus of a polypeptide fragment are well known in the art and can be obtained commercially (e.g., Clontech, Mountain View, Calif.).

An allelic variant of human GPR101 of SEQ ID NO: 2, or of mouse GPR101 SEQ ID NO: 4 or of rat GPR101 of SEQ ID NO: 6 is envisioned to be within the scope of the invention. Human GPR101 is envisioned to be within the scope of the invention.

A variant which is a vertebrate ortholog of human GPR101 of SEQ ID NO: 2 is envisioned to be within the scope of the invention. A variant which is a mammalian ortholog of human GPR101 of SEQ ID NO: 2 is envisioned to be within the scope of the invention. By way of illustration and not limitation, mouse GPR101 (e.g., SEQ ID NO: 4), rat GPR101 (e.g., SEQ ID NO: 6), cow GPR101 (e.g., GenBank® Accession No. XP_582650), dog GPR101 (e.g., GenBank® Accession No. XP_549287) and non-human primate GPR101 are envisioned to be within the scope of the invention.

In certain embodiments, the G protein-coupled receptor having a variant of the amino acid sequence of SEQ ID NO: 2, a variant of the amino acid sequence of SEQ ID NO: 4 or a variant of the amino acid sequence of SEQ ID NO: 6 exhibits a detectable level of constitutive activity. In certain embodiments, the G protein-coupled receptor having a variant of the amino acid sequence of SEQ ID NO: 2, a variant of the amino acid sequence of SEQ ID NO: 4 or a variant of the amino acid sequence of SEQ ID NO: 6 is constitutively active. In some embodiments, the constitutive activity is for increasing a level of intracellular cAMP. In some embodiments, the constitutive activity is for increasing a level of intracellular cAMP consistent with the G protein-coupled receptor being coupled to Gs. In some embodiments, the constitutive activity is for causing melanophore cells to undergo pigment dispersion. In certain embodiments, the G protein-coupled receptor having a variant of the amino acid sequence of SEQ ID NO: 2, the amino acid sequence of SEQ ID NO: 4 or the amino acid sequence of SEQ ID NO: 6 couples to Gs.

A variant of SEQ ID NO: 2, SEQ ID NO: 4 or SEQ ID NO: 6 having at least about 70%, at least about 75%, at least about 80%, at least about 85%, at least about 90%, at least about 95%, at least about 96%, at least about 97%, at least about 98%, or at least about 99% identity to SEQ ID NO: 2, SEQ ID NO: 4 or SEQ ID NO: 6, respectively, is envisioned to be within the scope of the invention. In certain embodiments, the variant of SEQ ID NO: 2, SEQ ID NO: 4 or SEQ ID NO: 6 having at least about 70%, at least about 75%, at least about 80%, at least about 85%, at least about 90%, at least about 95%, at least about 96%, at least about 97%, at least about 98%, or at least about 99% identity to SEQ ID NO: 2, SEQ ID NO: 4 or SEQ ID NO: 6, respectively, is a GPCR. In some embodiments, the variant of SEQ ID NO: 2, SEQ ID NO: 4 or SEQ ID NO: 6 is an endogenous GPCR. In some embodiments, the variant of SEQ ID NO: 2, SEQ ID NO: 4 or SEQ ID NO: 6 is a non-endogenous GPCR. In some embodiments, the variant of SEQ ID NO: 2, SEQ ID NO: 4 or SEQ ID NO: 6 that is an endogenous GPCR is a mammalian GPCR. In some embodiments, the variant of SEQ ID NO: 2, SEQ ID NO: 4 or SEQ ID NO: 6 having at least about 70%, at least about 75%, at least about 80%, at least about 85%, at least about 90%, at least about 95%, at least about 96%, at least about 97%, at least about 98%, or at least about 99% identity to SEQ ID NO: 2, SEQ ID NO: 4 or SEQ ID NO: 6, respectively, exhibits a detectable level of constitutive activity. In some embodiments, the constitutive activity is for increasing a level of intracellular cAMP consistent with the variant coupling to Gs. In some embodiments, the constitutive activity is for causing melanophore cells to undergo pigment dispersion. In certain embodiments, the variant of SEQ ED NO: 2, SEQ ID NO: 4 or SEQ ID NO: 6 having at least about 70%, at least about 75%, at least about 80%, at least about 85%, at least about 90%, at least about 95%, at least about 96%, at least about 97%, at least about 98%, or at least about 99% identity to SEQ ID NO: 2, SEQ ID NO: 4 or SEQ ID NO: 6, respectively, couples to Gs. Percent identity can be determined conventionally using known computer programs.

In certain embodiments, a variant GPCR that may be used in the subject methods has an amino acid sequence having at least about 70%, at least about 75%, at least about 80%, at least about 85%, at least about 90%, at least about 95%, of at least about 96%, at least about 97%, at least about 98%, or at least about 99% identity to SEQ ID NO: 2. By a variant GPCR having, for example, 95% "identity" to SEQ ID NO: 2 is meant that the amino acid sequence of the variant is identical to amino acids 1-508 of SEQ ID NO: 2 except that it may include up to five amino acid alterations per each 100 amino acids of SEQ ID NO: 2. Thus, to obtain for example an amino acid sequence having at least 95% identity to the amino acid sequence of SEQ ID NO: 2, up to 5% (5 of 100) of the amino acid residues in the sequence may be inserted, deleted, or substituted with another amino acid compared with amino acids 1-508 of SEQ ID NO: 2. These alternations may occur at the amino or carboxy termini or anywhere between those terminal positions, interspersed either subjectly among residues in the sequence or in one or more contiguous groups within the sequence.

In some embodiments, a variant GPCR that may be used in the subject methods is a GPCR encoded by a polynucleotide hybridizing under stringent conditions to the complement of SEQ ID NO: 1, SEQ ID NO: 3 or SEQ ID NO: 5. In some embodiments, a variant GPCR that may be used in the subject methods is a GPCR encoded by a polynucleotide hybridizing under stringent conditions to the complement of SEQ ID NO: 1. In some embodiments, the GPCR encoded by a polynucleotide hybridizing under stringent conditions to the complement of SEQ ID NO: 1, SEQ ID NO: 3 or SEQ ID NO: 5 is an endogenous GPCR. In some embodiments, the GPCR encoded by a polynucleotide hybridizing under stringent conditions to the complement of SEQ ID NO: 1, SEQ ID NO: 3 or SEQ ID NO: 5 is a non-endogenous GPCR. In some embodiments, the GPCR encoded by a polynucleotide hybridizing under stringent conditions to the complement of SEQ ID NO: 1, SEQ ID NO: 3 or SEQ ID NO: 5 and that is an endogenous GPCR is a mammalian endogenous GPCR. In some embodiments, the GPCR encoded by a polynucleotide hybridizing under stringent conditions to the complement of SEQ ID NO: 1, SEQ ID NO: 3 or SEQ ID NO: 5 is SEQ ID NO: 2 or an allele thereof, SEQ ID NO: 4 or an allele thereof or SEQ ID NO: 6 or an allele thereof. In some embodiments, the GPCR encoded by a polynucleotide hybridizing under stringent conditions to the complement of SEQ ID NO: 1, SEQ ID NO: 3 or SEQ ID NO: 5 is a vertebrate ortholog of SEQ ID NO:2, SEQ ID NO: 4 or SEQ ID NO: 6. In certain embodiments, the vertebrate is a mammal. In certain embodiments, the GPCR encoded by a polynucleotide hybridizing under stringent conditions to the complement of SEQ ID NO: 1, SEQ ID NO: 3 or SEQ ID NO: 5 exhibits a detectable level of constitutive activity. In some embodiments, the constitutive activity is for increasing a level of intracellular cAMP consistent with the GPCR being coupled to Gs. In some embodiments, the constitutive activity is for causing melanophore cells to undergo pigment dispersion. In certain embodiments, the GPCR encoded by a polynucleotide hybridizing under stringent conditions to the complement of SEQ ID NO: 1, SEQ ID NO: 3 or SEQ ID NO: 5 couples to Gs. Hybridization techniques are well known to the skilled artisan (see, e.g., Maniatis T et al., *Molecular Cloning: A Laboratory Manual* (1989) Cold Spring Harbor Laboratory). Exemplary stringent hybridization conditions comprise conducting the hybridization reaction at 42° C. in a solution comprising 50% formamide, 5×SSC (1×SSC=150 mM NaCl, 15 mM sodium citrate), and 1% SDS and washing at 55-65° C. in a solution comprising 0.1-0.2×SSC and 0.1% SDS. In certain embodiments, stringent hybridization conditions comprise a wash in a solution comprising 0.1-0.2×SSC at 55-65° C. In certain embodiments, stringent hybridization conditions comprise a wash at 55° C. in a solution comprising 0.1-0.2×SSC and 0.1% SDS. In certain embodiments, stringent hybridization conditions comprise a wash at 60° C. in a solution comprising 0.1-0.2×SSC and 0.1% SDS. In certain embodiments, stringent hybridization conditions comprise a wash at 65° C. in a solution comprising 0.1-0.2×SSC and 0.1% SDS. In certain embodiments, stringent hybridization conditions comprise a wash in a solution comprising 0.1×SSC. In certain embodiments, stringent hybridization conditions comprise a wash in a solution comprising 0.1×SSC and 0.1% SDS. In certain embodiments, stringent hybridization conditions comprise a wash in a solution comprising 0.2×SSC. In certain embodiments, stringent hybridization conditions comprise a wash in a solution comprising 0.2×SSC and 0.1% SDS.

In some embodiments, a GPCR that may be used in the subject methods is a non-endogenous, constitutively activated receptor comprising the amino acid sequence of SEQ ID NO: 2, wherein the alanine at amino acid position 398 of SEQ ID NO: 2 is substituted with an amino acid other than alanine. In some embodiments, the amino acid other than alanine is lysine. In some embodiments, the amino acid other than alanine is arginine. In some embodiments, the amino acid other than alanine is histidine.

In certain embodiments, a GPCR of the invention forms part of a fusion protein with a G protein.

a. Sequence Identity

In certain embodiments, percent identity is evaluated using the Basic Local Alignment Search Tool ("BLAST"), which is well known in the art [See, e.g., Karlin and Altschul, Proc Natl Acad Sci USA (1990) 87:2264-2268; Altschul et al., J Mol Biol (1990) 215:403-410; Altschul et all, Nature Genetics (1993) 3:266-272; and Altschul et al., Nucleic Acids Res (1997) 25:3389-3402; the disclosure of each of which is herein incorporated by reference in its entirety]. The BLAST programs may be used with the default parameters or with modified parameters provided by the user. Preferably, the parameters are default parameters.

In some embodiments, a preferred method for determining the best overall match between a query sequence (e.g., the amino acid sequence of SEQ ID NO:2) and a sequence to be interrogated, also referred to as a global sequence alignment, can be determined using the FASTDB computer program based on the algorithm of Brutlag et al. [Comp App Biosci (1990) 6:237-245; the disclosure of which is herein incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bses of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion Proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula, Renilla reniformis* or *Renilla muelleri*), or light emitting variants thereof. Other suitable reporter domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques.

For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8).

In some embodiments, the codons of the nucleic acids encoding polypeptides of interest are optimized for expression in cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell and include expression vectors which are commercially available (e.g., from Invitrogen, Carlsbad, Calif.; Clontech, Mountain View, Calif.; Stratagene, La Jolla, Calif.). Commercially available expression vectors include, by way of non-limiting example, CMV promoter-based vectors. One suitable expression vector is pCMV. The expression vector may be adenoviral. An exemplary adenoviral vector may be purchased as AdEasy™ from Qbiogene (Carlsbad, Calif.) [He T C et al, Proc Natl Acad Sci USA (1998) 95:2509-2514; and U.S. Pat. No. 5,922,576; the disclosure of each of which is herein incorporated by reference in its entirety]. Other suitable expression vectors will be readily apparent to those of ordinary skill in the art.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol Pharmacol. 1999 56:1182-91; Ramsay et al., Br. J. Pharmacology, 2001, 315-323) and will not be described any further. It is expressly contemplated that such a fusion protein may contain a heterologous N-terminal domain (e.g., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites, multiple cloning sites, primer binding sites, ligatable ends, recombination sites etc., usually in order to facilitate the construction of a nucleic acid encoding a polypeptide of interest.

b. Host Cells

The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example, a yeast cell, a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); and mouse L cells (ATCC CCL-1).

In certain embodiments, melanophores are used. Melanophores are skin cells found in lower vertebrates. Relevant materials and methods will be followed according to the disclosure of U.S. Pat. No. 5,462,856 and U.S. Pat. No. 6,051, 386. These patent disclosures are herein incorporated by reference in their entirety.

Additional cell lines will become apparent to those of ordinary skill in the art, and a wide variety of cell lines are available from the American Type Culture Collection, 10801 University Boulevard, Manassas, Va. 20110-2209.

C. Screening of Candidate Compounds

1. Generic GPCR Screening Assay Techniques

When a G protein receptor becomes active, it binds to a G protein (e.g. Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. A preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid PIP$_2$, releasing two intracellular messengers: diacyclglycerol (DAG) and inositol 1,4,5-triphosphate (IP$_3$). Increased accumulation of IP$_3$ is associated with activation of Gq- and Go-associated receptors. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Assays that detect IP$_3$ accumulation can be utilized to determine if a candidate compound is, e.g., an inverse agonist to a Gq- or Go-associated receptor (i.e., such a compound would decrease the levels of IP$_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian or a melanophore expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the GPCR. The GPCR Fusion Protein may be preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments, it is preferred that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 4(a) below) be available for insertion of a GPCR sequence therein; this provides for further efficiency in the context of large-scale screening of a variety of different GPCRs having different sequences.

As noted above, activated GPCRs that couple to Gi, Gz and Go are expected to inhibit the formation of cAMP making assays based upon these types of GPCRs challenging (i.e., the cAMP signal decreases upon activation, thus making the direct identification of, e.g., agonists (which would further decrease this signal) challenging). As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

which can make the assessment of cAMP levels challenging. In certain embodiments, an effective technique in measuring the decrease in production of cAMP as an indication of activation of a receptor that predominantly couples Gi upon activation can be accomplished by co-transfecting a signal enhancer, e.g. a non-endogenous, constitutively activated receptor that predominantly couples with Gs upon activation (e.g., TSHR-A623I; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

D. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

TABLE C

| G protein | Effect on cAMP Production upon Activation of GPCR (i.e., constitutive activation or agonist binding) | Effect on IP$_3$ Accumulation upon Activation of GPCR (i.e., constitutive activation or agonist binding) | Effect on cAMP Production upon contact with an Inverse Agonist | Effect on IP$_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will force the endogenous Gi coupled receptor to couple to its non-endogenous G protein, Gq, such that the second messenger, for example, inositol triphosphate or diacylglycerol, can be measured in lieu of cAMP production.

4. Co-Transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments, direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of subject members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the subject library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

In some embodiments, the candidate compound is a polypeptide. In some preferred embodiments, the candidate compound is a small molecule. In some embodiments, the candidate compound is not an antibody or an antigen-binding fragment thereof.

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

In certain embodiments, a modulator of the invention is orally active. A number of computational approaches available to those of ordinary skill in the art have been developed for prediction of oral bioavailability of a drug [Ooms et al., Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). Furthermore, positron emission tomography (PET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety]. In some embodiments, a modulator of the invention is orally active.

In certain embodiments, a modulator of the invention which is orally active is able to cross the blood-brain barrier. A number of computational approaches available to those of ordinary skill in the art have been developed for prediction of the permeation of the blood-brain barrier [Ooms et al., Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). A number of in vitro methods have been developed to predict blood-brain barrier permeability of drugs [Lohmann et al., J Drug Target (2002) 10:263-76; Hansen et al., J Pharm Biomed Anal (2002) 27:945-58; Otis et al., J Pharmacol Toxicol Methods (2001) 45:71-7; Dehouck et al, J Neurochem (1990) 54:1798-801; the disclosure of each of which is herein incorporated by reference in its entirety]. Furthermore, a number of strategies have been developed to enhance drug delivery across the blood-brain barrier [Scherrmann, Vascul Pharmacol (2002) 38:349-54; Pardridge, Arch Neurol (2002) 59:35-40; Pardridge, Neuron (2002) 36:555-8; the disclosure of each of which is hereby incorporated by reference in its entirety]. Finally, positron emission tomography (PET) has been successfully used by a number of groups to obtain direct measurements of drug distribution, including that within brain, in the mammalian body, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety].

In certain embodiments, said modulator is selective for GPR101, wherein a modulator selective for GPR101 is understood to refer to a modulator having selectivity for GPR101 over one or more closely related receptors, such as GPR161 (GenBank® Accession No. CAI22624). In certain embodiments, a GPR101 selective modulator is a GPR101 selective agonist or partial agonist having a selectivity for GPR101 over GPR161 of at least about 10-fold, of at least about 100-fold or of at least about 1000-fold. In certain embodiments, a GPR101 selective modulator is a GPR101 selective inverse agonist or antagonist having a selectivity for GPR101 over GPR161 of at least about 10-fold, of at least about 100-fold or of at least about 1000-fold. In some preferred embodiments, GPR101 is human GPR101.

In some embodiments, the modulator is an agonist or a partial agonist with an $EC_{50}$ of less than about 10 μM, of less than about 1 μM, of less than about 100 nM, or of less than about 10 nM at human, mouse or rat GPR101, preferably at human GPR101. In some embodiments, the modulator is an agonist or a partial agonist with an $EC_{50}$ of less than a value selected from the interval of about 10 nM to 10 μM. In some embodiments, the modulator is an agonist or a partial agonist with an $EC_{50}$ of less than a value selected from the interval of about 10 nM to 1 μM. In some embodiments, the modulator is an agonist or a partial agonist with an $EC_{50}$ of less than a value selected from the interval of about 10 nM to 100 nM. In some embodiments, the modulator is an agonist or a partial agonist with an $EC_{50}$ of less than about 10 μM, of less than about 1 μM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an agonist or a partial agonist with an $EC_{50}$ of less than about 10 μM, of less than about 1 μM, of less than about 100 nM, or of less than about 10 nM in said assay. In some embodiments, the modulator is an agonist or a partial agonist with an $EC_{50}$ in said assay of less than a value selected from the interval of about 10 nM to 10 μM. In some embodiments, the modulator is an agonist or a partial agonist with an $EC_{50}$ in said assay of less than a value selected from the interval of about 10 nM to 1 μM. In some embodiments, the modulator is an agonist or a partial agonist with an $EC_{50}$ in said assay of less than a value selected from the interval of about 10 nM to 100 nM.

In some embodiments, the modulator is an inverse agonist or an antagonist with an $IC_{50}$ of less than about 10 μM, of less than about 1 μM, of less than about 100 nM, or of less than about 10 nM at human, mouse or rat GPR101, preferably at human GPR101. In some embodiments, the modulator is an inverse agonist or an antagonist with an $IC_{50}$ of less than a value selected from the interval of about 10 nM to 10 μM. In some embodiments, the modulator is an inverse agonist or an antagonist with an $IC_{50}$ of less than a value selected from the interval of about 10 nM to 1 μM. In some embodiments, the modulator is an inverse agonist or an antagonist with an $IC_{50}$ of less than a value selected from the interval of about 10 nM to 100 nM. In some embodiments, the modulator is an inverse agonist or an antagonist with an $IC_{50}$ of less than about 10 μM, of less than about 1 μM, of less than about 100 nM, or of less than about 10 nM in GTPγS binding assay carried out with membrane from transfected CHO cells, or in pigment dispersion assay carried out in transfected melanophores, in cAMP assay carried out in transfected CHO cells or with membrane from transfected CHO cells, or in cAMP assay carried out in transfected 293 cells, wherein the transfected CHO cells or the transfected melanophore cells or the transfected 293 cells express a recombinant GPR101 receptor having an amino acid sequence selected from SEQ ID NO: 2, SEQ ID NO: 4 and SEQ ID NO: 6. In some embodiments, the recombinant GPR101 receptor has the amino acid sequence of SEQ ID NO: 2. In some embodiments, the modulator is an inverse agonist or an antagonist with an $IC_{50}$ of less than about 10 μM, of less than about 1 μM, of less than about 100 nM, or of less than about 10 nM in said assay. In some embodiments, the modulator is an inverse agonist or an antagonist with an $IC_{50}$ in said assay of less than a value selected from the interval of about 10 nM to 10 μM. In some embodiments, the modulator is an inverse agonist or an antagonist with an $IC_{50}$ in said assay of less than a value selected from the interval of about 10 nM to 1 μM. In some embodiments, the modulator is an inverse agonist or an antagonist with an $IC_{50}$ in said assay of less than a value selected from the interval of about 10 nM to 100 nM.

E. Pharmaceutical Compositions

The invention provides methods of treatment (and prevention) (and modulation, such as increasing or decreasing) by administration to an subject in need of said treatment (or prevention) (or modulation) a therapeutically effect amount of a compound (e.g., a modulator or a ligand) of the invention (also see, e.g., PCT Application Number PCT/IB02/01461 published as WO 02/066505 on 29 Aug. 2002; the disclosure of which is herein incorporated by reference in its entirety). In one aspect, the modulator or the ligand is a small molecule. In one aspect, the modulator is a small molecule with the proviso that the small molecule is not a polypeptide, an antibody or an antigen-binding fragment thereof, or a lipid. In one aspect, the modulator is a small molecule with the proviso that the small molecule is not a polypeptide. In one aspect, the modulator is a small molecule with the proviso that the small molecule is not an antibody or an antigen-binding fragment thereof. In one aspect, the modulator is a small molecule with the proviso that the small molecule is not a lipid. In one aspect, the modulator is an an agonist or a partial agonist of a GPCR of the invention. In one aspect, the modulator is an agonist or a partial agonist of vertebrate GPR101 receptor. In one aspect, the modulator is an agonist or a partial agonist of a mammalian GPR101 receptor. In one aspect the modulator is an agonist or a partial agonist of a human GPR101 receptor. In one aspect, the modulator is an an agonist. In one aspect, the modulator is a partial agonist. In one aspect, the modulator is an an inverse agonist or an antagonist of a GPCR of the invention. In one aspect, the modulator is an inverse agonist or an antagonist of a vertebrate GPR101 receptor. In one aspect, the modulator is an inverse agonist or an antagonist of a mammalian GPR101 receptor. In one aspect, the modulator is an inverse agonist or an antagonist of a human GPR101 receptor. In one aspect, the modulator is an inverse agonist. In one aspect, the modulator is an antagonist. In one aspect, the modulator or the ligand is substantially purified. In one aspect, the subject is a vertebrate. In one aspect, the subject is a mammal. In one aspect, the subject is a human.

Modulators and ligands of the invention can be administered to non-human vertebrates (e.g., non-human mammals) (see Examples, infra) and/or humans, alone or in pharmaceutical compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical composition is then provided at a therapeutically effective dose. A therapeutically effective dose refers to that amount of a modulator or ligand sufficient to result in prevention or amelioration of symptoms or physiological status of a disorder as determined illustratively and not by limitation by the methods described herein wherein the prevention or amelioration of symptoms or physiological status of a disorder includes but is not limited to treating or preventing a POMC-derived biologically active peptide-related disorder, treating or preventing obesity or a condition related thereto, promoting satiety, treating or preventing hyperphagia, treating or preventing pyrexia, treating or preventing an inflammation-associated disorder, decreasing body mass in a subject, decreasing adiposity in a subject, decreasing percentage body fat, decreasing food intake, and treating or preventing a cachexia.

It is expressly considered that the modulators of the invention may be provided alone or in combination with other pharmaceutically or physiologically acceptable compounds. Other compounds for the treatment of disorders of the invention, wherein disorders of the invention include but are not limited to a POMC-derived biologically active peptide-related disorder ameliorated by increasing a level of secretion of the POMC-derived biologically active peptide, obesity and conditions related thereto, hyperphagia, pyrexia, a brain inflammation-related disorder, and a cachexia, are currently well known in the art. In certain embodiments, the level of secretion is a level of hypothalamic secretion.

While the compounds of the invention can be administered as the sole active pharmaceutical agent (i.e., mono-therapy), compounds of the invention can also be used in combination with other pharmaceutical agents (i.e., combination-therapy) for the treatment of the diseases/conditions/disorders described herein. Therefore, another aspect of the present invention includes methods of treatment comprising administering to a subject in need of treatment a therapeutically effective amount of a compound (e.g., a modulator, a ligand) of the present invention, such as but not limited to an agonist or a partial agonist of a vertebrate (e.g., mammalian, human) GPR101 receptor, in combination with one or more additional pharmaceutical agent as described herein. It will be understood that the scope of combination-therapy of the compounds of the present invention with other pharmaceutical agents is not limited to those listed herein, supra or infra, but includes in principle any combination with any pharmaceutical agent or pharmaceutical composition useful for the treatment diseases, conditions or disorders of the present invention in a subject.

In one aspect of the present invention, the other pharmaceutically or physiologically acceptable compound is an anti-obesity agent such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related protein (AGRP) antagonists, selective 5-HIT2C receptor agonists (including lorcaserin hydrochloride), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion). In some embodiments, the anti-obesity agent is selected from the group consisting of orlistat, sibutramine, bromocriptine, ephedrine, leptin, pseudoephedrine, and selective 5-HT2C agonist (including lorcaserin hydrochloride).

In one aspect of the present invention, the other pharmaceutically or physiologically acceptable compound is an anti-inflammatory agent such as nonsteroidal anti-inflammatory drugs (e.g., celecoxib, rofecoxib), aminosalicylates (e.g. sulfasalazine, mesalamine, azodisalicylate, balsalazide), hydroxychoroquine, aurothioglucose, sodium-aurothiomalate, auranofin, penicillamine, leflunomide, corticosteroids (e.g., prednisone, prednisolone, budesonide, hydrocortisone, methylprednisolone), immunosuppressants (e.g., azathioprine, cyclosporine, methotrexate, 6-mercaptopurine), and biologic agents (e.g., etanercept, infliximab, adiponectin or an orally active analog thereof)

In one aspect of the present invention, the other pharmaceutically or physiologically acceptable compound is an anti-pyrexia agent such as acetaminophen and ibuprofen.

In accordance to an aspect of the present invention, a compound of the present invention can be used in combination with a pharmaceutical agent or agents belonging to one or more of the classes of drugs cited herein.

Routes of Administration

Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In certain embodiments, route of administration is oral.

Composition/Formulation

Pharmaceutical or physiologically acceptable compositions and medicaments for use in accordance with the present invention may be formulated in a conventional manner using one or more pharmaceutically or physiologically acceptable carriers comprising excipients and auxiliaries. Compounds of the invention (e.g., modulators, ligands) can be formulated into pharmaceutical compositions using techniques well known in the art. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils; liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in multi-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). Other controlled release systems are discussed in the review by Langer (1990, Science 249: 1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase an intracellular level of cAMP in a cell comprising GPR101 in an in vitro assay. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the subject physician in view of the patient's condition. (See, e.g., Fingl et al., 1975, in "The Pharmacological Basis of Therapeutics", Ch. 1).

Dosage amount and interval may be adjusted subjectly to provide plasma levels of the active compound which are sufficient to prevent or treat a disorder of the invention, depending on the particular situation. Dosages necessary to achieve these effects will depend on subject characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention. Said desired results include, but are not limited to, increasing hypothalamic proopiomelanocortin (POMC)-derived biologically active peptide secretion in a subject, promoting satiety in a subject, decreasing body mass in a subject, decreasing adiposity in a subject, decreasing percentage body fat in a subject, decreasing food intake in a subject, treating or preventing obesity or a condition related thereto, treating or preventing hyperphagia, treating or preventing pyrexia, and treating or preventing an inflammation-associated disorder.

F. Methods of Treatment

The invention is drawn inter alia to methods including, but not limited to, methods of increasing hypothalamic proopiomelanocortin (POMC)-derived biologically active peptide secretion comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of treating or preventing a POMC-derived biologically active peptide-related disorder ameliorated by increasing a level of secretion of the POMC-derived biologically active peptide comprising administering to a vertebrate in need thereof a therapeutically effective amount of a modulator of the vertebrate GPR101 or a pharmaceutical composition comprising the modulator and a pharmaceutically acceptable carrier. A POMC-derived biologically active peptide-related disorder ameliorated by increasing a level of secretion of a POMC-derived biologically active peptide shall be understood to include but not be limited to obesity or a condition related thereto, hyperphagia, pyrexia and an inflammation-associated disorder. In certain embodiments, the level of secretion is a level of hypothalamic secretion. The invention is also drawn to methods of treating or preventing obesity or a condition related thereto comprising administering to a vertebrate in need thereof a therapeutically effective amount of a modulator of the vertebrate GPR101 receptor or a pharmaceutical composition comprising the modulator and a pharmaceutically acceptable carrier. In some embodiments, the condition related to obesity is selected from the group consisting of hypertension, congestive cardiomyopathy, varicosities, pulmonary embolism, coronary heart disease, stroke, idiopathic intracranial hypertension, meralgia parethetica, dyspnea, obstructive sleep apnea, hypoventilation syndrome, Pickwickian syndrome, asthma, immobility, degenerative osteoarthritis, low back pain, striae distensae or "stretch marks," venous stasis of the lower extremities, lymphedema, cellulitis, intertrigo, carbuncles, acanthosis nigricans, skin tags, gastro-esophageal reflux disorder, nonalcoholic fatty liver/steatohepatitis, cholelithiasis, hernias, colon cancer, stress incontinence, obesity-related glomerulopathy, breast and uterine cancer, depression and low self-esteem, impaired quality of life, metabolic syndrome, insulin resistance, Type 2 diabetes, dyslipidemia, atherosclerosis, hyperandrogenemia in women, polycystic ovarian syndrome, dysmenorrhea, infertility, pregnancy complications, and male hypogonadism. In certain embodiments, the condition related to obesity is selected from the group consisting of hypertension, insulin resistance, metabolic syndrome, Type 2 diabetes, dyslipidemia, atherosclerosis, coronary heart disease, and stroke. It is expressly contemplated that each individual condition related to obesity is a separate embodiment within the scope of the present invention. The invention is also drawn to methods of promoting satiety comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of treating or preventing hyperphagia comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of treating or preventing pyrexia comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of treating or preventing an inflammation-associated disorder comprising administering to a vertebrate in need thereof a therapeutically effective amount of a modulator of the vertebrate GPR101 receptor or a pharmaceutical composition comprising the modulator and a pharmaceutically acceptable carrier. In certain embodiments, the inflammation-associated disorder is selected from the group consisting of inflammatory bowel disease (such as Crohn's disease and ulcerative colitis), inflammatory arthritis (such as rheumatoid arthritis and psoriatic arthritis), psoriasis, asthma, chronic obstructive pulmonary disease, septic shock, ischemia/reperfusion injury, disseminated intravascular coagulation, atherosclerosis, osteoporosis, restenosis, systemic lupus erythematosus, acute transplant rejection, myocardial infarction, pancreatitis, hepatitis, venous thrombosis, multiple trauma, congestive heart failure, peripheral nerve injury, and a brain inflammation-related disorder. In some embodiments, the inflammation-associated disorder is selected from the group consisting of inflammatory bowel disease, inflammatory arthritis, septic shock, ischemia/reperfusion injury, atherosclerosis, osteoporosis, restenosis, myocardial infarction, congestive heart failure, and a brain inflammation-related disorder. It is expressly contemplated that each individual inflammation-associated disorder is a separate embodiment within the scope of the present invention. In some embodiments, the brain inflammation-related disorder is selected from the group consisting of brain injury or trauma, multiple sclerosis, amyotrophic lateral sclerosis, Parkinson's disease, prion-associated disease, cerebral ischemia, AIDS dementia and Alzheimer's disease. It is expressly contemplated that each individual brain inflammation-related disorder is a separate embodiment within the scope of the present invention. The invention is also drawn to methods of decreasing body mass comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of decreasing adiposity comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of decreasing percentage body fat comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of decreasing food intake comprising administering to a vertebrate in need thereof a therapeutically effective amount of a modulator of the vertebrate GPR101 receptor or a pharmaceutical composition comprising the modulator and a pharmaceutically acceptable carrier. In certain embodiments, the modulator is an agonist or a partial agonist. In some embodiments, the modulator is an agonist. In some embodiments, the modulator is a partial agonist. In some embodiments, said modulator is orally active. In some embodiments, said orally active modulator is further able to cross the blood-brain barrier. In some embodiments, the modulator is administered to the subject in a pharmaceutical composition. In some embodiments, the modulator is provided to the subject in a pharmaceutical composition. In some embodiments, the modulator is provided to the subject in a pharmaceutical composition that is taken orally. In some embodiments, the vertebrate is a mammal. In certain embodiments, the mammal is a mouse, a rat, a rabbit, a non-human primate, or a human. In some embodiments, the subject is a non-human mammal. In certain embodiments, the vertebrate is a human.

The invention is drawn inter alia to methods including, but not limited to, methods of decreasing hypothalamic proopiomelanocortin (POMC)-derived biologically active peptide secretion comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of treating or preventing a POMC-derived biologically active peptide-related disorder ameliorated by decreasing a level of secretion of the POMC-derived biologically active peptide comprising administering to a vertebrate in need thereof a therapeutically effective amount of a modulator of the vertebrate GPR101 or a pharmaceutical composition comprising the modulator and a pharmaceutically acceptable carrier. A POMC-derived biologically active peptide-related disorder ameliorated by decreasing a level of secretion of a POMC-derived biologically active peptide shall be understood to include but not be limited to a cachexia. In certain embodiments, the level of secretion is a level of hypothalamic secretion. The invention is also drawn to methods of treating or preventing a cachexia comprising administering to a vertebrate in need thereof a therapeutically effective amount of a modulator of the vertebrate GPR101 receptor or a pharmaceutical composition comprising the modulator and a pharmaceutically acceptable carrier. In some embodiments, the cachexia is selected from the group consisting of AIDS-related weight loss, cancer-related weight loss and anorexia-related weight loss. It is expressly contemplated that AIDS-related weight loss, cancer-related weight loss and anorexia-related weight loss are separate embodiments within the scope of the present invention. The invention is also drawn to methods of increasing body mass comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of increasing adiposity comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of increasing percentage body fat comprising administering to a vertebrate in need thereof a therapeutically effective amount of a modulator of the vertebrate GPR101 receptor or a pharmaceutical composition comprising the modulator and a pharmaceutically acceptable carrier. The invention is also drawn to methods of increasing food intake comprising administering to a vertebrate in need thereof a therapeutically effective amount of a modulator of the vertebrate GPR101 receptor or a pharmaceutical composition comprising the modulator and a pharmaceutically acceptable carrier. In certain embodiments, the modulator is an inverse agonist or an antagonist. In some embodiments, the modulator is an inverse agonist. In some embodiments, the modulator is an antagonist. In some embodiments, said modulator is orally active. In some embodiments, said orally active modulator is further able to cross the blood-brain barrier. In some embodiments, the modulator is administered to the subject in a pharmaceutical composition. In some embodiments, the modulator is provided to the subject in a pharmaceutical composition. In some embodiments, the modulator is provided to the subject in a pharmaceutical composition that is taken orally. In some embodiments, the vertebrate is a mammal. In certain embodiments, the mammal is a mouse, a rat, a rabbit, a non-human primate, or a human. In some embodiments, the subject is a non-human mammal. In certain embodiments, the vertebrate is a human.

G. Other Utility

Agents that modulate (e.g., inhibit or stimulate) receptor functionality of a GPCR of the invention such as a mammalian GPR101 may be identified by contacting a candidate compound with the GPCR and determining the effect of the candidate compound on receptor functionality. The selectivity of a compound that modulates the functionality of a mammalian GPR101 such as human GPR101 can be evaluated by comparing its effects on GPR101 to its effects on one or more other G protein-coupled receptors. In certain embodiments, the GPR101 modulator is a selective GPR101 modulator, such as but not limited to an agonist or partial agonist, wherein the selective GPR101 modulator has a selectivity for GPR101 over GPR161 receptor of at least about 10-fold, of at least about 100-fold or of at least about 1000-fold. Following identification of compounds that modulate GPR101 functionality, such compounds may be further tested in other assays including, but not limited to, in vivo models, in order to confirm or quantitate their activity. Modulators of GPR101 functionality are therapeutically useful, e.g., in treatment of diseases and physiological conditions in which normal or aberrant GPR101 functionality is involved.

Agents that are ligands of a GPCR of the invention such as a mammalian GPR101 may be identified by contacting a candidate compound with the GPCR and determining whether the candidate compound binds to the receptor. The selectivity of a compound that binds to a mammalian GPR101 such as human GPR101 can be evaluated by comparing its binding to GPR101 to its binding to one or more other G protein-coupled receptors. In some embodiments, the GPR101 ligand is a selective GPR101 ligand, wherein the selective GPR101 ligand has a selectivity for GPR101 over GPR161 receptor of at least about 10-fold, of at least about 100-fold or of at least about 1000-fold. Ligands that are modulators of GPR101 receptor functionality are therapeutically useful in treatment of diseases and physiological conditions in which normal or aberrant GPR101 functionality is involved.

The present invention also relates to radioisotope-labeled versions of compounds of the invention identified as modulators or ligands of a GPCR of the invention such as a mammalian GPR101 that would be useful in radioimaging as well as in assays, both in vitro and in vivo, for localizing and quantitating GPR101 in tissue samples, including human, and for identifying GPR101 ligands in methods relating to inhibition of binding of a radioisotope-labeled compound such as a known ligand of GPR101 or in methods of direct binding. It is a further object of this invention to develop novel assays relating to a GPCR of the invention such as a mammalian GPR101, such as human GPR101, which comprise such radioisotope-labeled compounds. By way of illustration and not limitation, it is envisioned that reduced brain GPR101 below a normal range visualized by radioimaging identifies a subject at risk for obesity or a condition related thereto or at risk for an inflammation-associated disorder. In some embodiments, the brain GPR101 is hypothalamic GPR101. In some embodiments, the brain GPR101 is hypothalamic arcuate nucleus GPR101. In some embodiments, the subject is a human.

The present invention also relates a method of radioimaging comprising administering to a mammal in need of said radioimaging a radiolabeled compound that is a modulator or a ligand of the mammalian GPR101 receptor. In one aspect, the ligand of the mammalian GPR101 receptor is not a modulator of the mammalian GPR101 receptor. In some embodiments, the mammal is a human. In some embodiments, the method of radioimaging is for identifying whether the mammal is at risk for or progressing toward obesity or a condition related thereto, wherein a level of brain GPR101 in the mammal below a normal range is indicative of the mammal being at risk for or progressing toward obesity or a condition related thereto. In some embodiments, the method of radioimaging is for identifying the mammal for prevention or treatment of obesity or a condition related thereto with an agonist or a partial agonist of the mammalian GPR101 or with a pharmaceutical composition comprising the agonist or partial agonist and a pharmaceutically acceptable carrier, wherein a level of brain GPR101 in the mammal below a normal range identifies the mammal for prevention or treatment of obesity or the condition related thereto with the agonist or the partial agonist of the mammalian GPR101 or with the pharmaceutical composition comprising the agonist or the partial agonist and a pharmaceutically acceptable carrier. In some embodiments, the method of radioimaging is for identifying whether the mammal is at risk for or progressing toward an inflammation-associated disorder, wherein a level of brain GPR101 in the mammal below a normal range is indicative of the mammal being at risk for or progressing toward the inflammation-associated disorder. In some embodiments, the method of radioimaging is for identifying the mammal for prevention or treatment of an inflammation-associated disorder with an agonist or a partial agonist of the mammalian GPR101 or with a pharmaceutical composition comprising the agonist or partial agonist and a pharmaceutically acceptable carrier, wherein a level of brain GPR101 in the mammal below a normal range identifies the mammal for prevention or treatment of the inflammation-associated disorder with the agonist or the partial agonist of the mammalian GPR101 or with the pharmaceutical composition comprising the agonist or the partial agonist and a pharmaceutically acceptable carrier. In some embodiments, the brain GPR101 is hypothalamic GPR101. In some embodiments, the brain GPR101 is hypothalamic arcutate nucleus GPR101. Radioimaging techniques are well known to the skilled artisan (see, e.g., Campbell, Q J Nucl Med (1997) 41:163-9).

The present invention embraces radioisotope-labeled versions of compounds of the invention identified as modulators or ligands of a GPCR of the invention such as a mammalian GPR101, such as human GPR101.

The present invention also relates to radioisotope-labeled versions of test compounds that are useful for detecting a ligand bound to a GPCR of the invention such as a mammalian GPR101, such as human GPR101. In some embodiments, the present invention expressly contemplates a library of said radiolabeled test compounds useful for detecting a ligand bound to a GPCR of the invention such as a mammalian GPR101, such as human GPR101. In certain embodiments, said library comprises at least about 10, at least about $10^2$, at least about $10^3$, at least about $10^5$, or at least about $10^6$ said radiolabeled test compounds. It is a further object of this invention to develop novel assays relating to a GPCR of the invention such as a mammalian GPR101, such as human GPR101, which comprise such radioisotope-labeled test compounds.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (deuterium), $^3H$ (tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compound will depend on the specific application of that radio-labeled compound. For example, for in vitro GPR101 receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful. In some embodiments, the radionuclide is selected from the group consisting of $^3H$, $^{11}C$, $^{18}F$, $^{14}C$, $^{125}I$, $^{124}I$, $^{131}I$, $^{35}S$ and $^{82}Br$.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3H$]—This procedure is rather inexpensive and requires precursors containing reducible functional groups such as aldehydes, ketones, lactones, esters, and the like.

C. Reduction with Lithium Aluminum Hydride [$^3H$]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl (3H) products by treating appropriate precursors with high specific activity methyl iodide (3H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro GPR101 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Methods for adding one or more substituents comprising a radionuclide are within the purview of the skilled artisan and include, but are not limited to, addition of radioisotopic iodine by enzymatic method (Marchalonic J J, Biochemical Journal (1969) 113:299-305; Thorell J I and Johansson B G, Biochimica et Biophysica Acta (1969) 251:363-9; the disclosure of each of which is herein incorporated by reference in its entirety) and or by Chloramine-T/Iodogen/Iodobead methods (Hunter W M and Greenwood F C, Nature (1962) 194: 495-6; Greenwood F C et al., Biochemical Journal (1963) 89:114-23; the disclosure of each of which is herein incorporated by reference in its entirety).

The foregoing techniques are intended to be illustrative and not limiting. Other techniques for radiolabeling a test compound or a compound known to be a ligand of a G protein-coupled receptor of the invention are well known to the skilled artisan.

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. Such modified approaches are considered within the purview of this disclosure. Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Recombinant DNA techniques relating to the subject matter of the present invention and well known to those of ordinary skill in the art can be found, e.g, in Maniatis T et al., *Molecular Cloning: A Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is herein incorporated by reference in its entirety.

Example 1

Full-Length Cloning of Endogenous Human GPR101

Polynucleotide encoding endogenous human GPR101 was cloned by polymerase chain reaction PCR) using primers

```
                              (SEQ ID NO: 7; sense)
5'-GCTGTTGCCATGACGTCCACCTGCAC-3'
and (SEQ ID NO: 8; antisense)
5'-GGACAGTTCAAGGTTTGCCTTAGAAC-3'
``` and human genomic DNA (Clontech) as template. TaqPlus Precision DNA polymerase (Stratagene) was used for the amplification by the following cycle with step 2 to step 4 repeated 35 times: 94° C., 3 minutes; 94° C., 20 seconds; 65° C., 20 seconds; 72° C., 2 minutes; 72° C., 7 minutes.

A 1.5 Kb PCR fragment was isolated and cloned into the pCRII-TOPO vector (Invitrogen) and completely sequenced using the ABI Big Dye Terminator kit (P.E. Biosystem). The nucleic acid sequence of human GPR101 is set forth in SEQ ID NO: 1; the encoded amino acid sequence of human GPR101 is set forth in SEQ ID NO: 2.

Example 2

Receptor Expression

A variety of cells are available to the art for the expression of proteins including, but not limited to, yeast cells, mammalian cells and melanophore cells. In certain embodiments, yeast cells are utilized. In certain embodiments, mammalian cells are utilized. In certain embodiments, melanophore cells are utilized. Of the mammalian cells, CHO, COS-7, MCB3901, 293 and 293T cells are particularly preferred, although the specific mammalian cell utilized can be predicated upon the particular needs of the artisan. See infra as relates to melanophores, including Example 9.

a. Transient Transfection

On day one, $4\times10^6$ 293 cells per 10 cm dish are plated out. On day two, two reaction tubes are prepared (the proportions to follow for each tube are per plate): tube A is prepared by mixing 4 µg DNA (e.g., pCMV vector; pCMV vector comprising polynucleotide encoding a GPCR of the invention, etc.) in 0.5 ml serum free DMEM (Gibco BRL); tube B is prepared by mixing 24 µl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12\times10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to 80% confluency), the cells are transfected using 12 µg of DNA (e.g., pCMV-neo$^r$ vector comprising polynucleotide encoding a GPCR of the invention). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/ml. The transfected cells now undergo selection for positively transfected cells containing the G418 resistance gene. The medium is replaced every four to five days as selection occurs. During selection, cells are grown to create stable pools, or split for stable clonal selection.

Example 3

Assays for Determination of GPCR Activation (e.g., Screening Assays)

A variety of approaches are available for assessing activation of a GPCR of interest, or "target" GPCR. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used to screen candidate compounds as modulators of GPCRs. The assay is generic and has application to drug discovery at all G protein-coupled receptors.

The [$^{35}$S]GTPγS assay is incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 µg membrane protein (e.g 293 cells expressing a GPCR of the invention; this amount can be adjusted for optimization) and 10 µM GDP (this amount can be changed for optimization) for 1 hour. Wheatgerm agglutinin beads (25 µl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty-four to forty-eight hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) is prepared and maintained in accordance with the manufacturer's instructions. Assay Buffer is prepared fresh for screening and contains 50 µl of Stimulation Buffer, 3 ul of test compound (12 µM final assay concentration) and 50 µl cells. Assay Buffer is stored on ice until utilized. The assay, preferably carried out e.g. in a 96-well plate, is initiated by addition of 50 µl of cAMP standards to appropriate wells followed by addition of 50 ul of PBS to wells H-11 and H12. 50 µl of Stimulation Buffer is added to all wells. DMSO (or selected candidate compounds) is added to appropriate wells using a pin tool capable of dispensing 3 µl of compound solution, with a final assay concentration of 12 µM test compound and 100 µl total assay volume. The cells are then added to the wells and incubated for 60 min at room temperature. 100 µl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP Assay for Gi-Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi coupled Target GPCR to establish a baseline level of cAMP. The Gi coupled receptor is co-transfected with the signal enhancer, and it is this material that can be used for screening. Such an approach can be utilized to effectively generate a signal when a cAMP assay is used. In some embodiments, this approach is preferably used in the identification of candidate compounds against G1 coupled receptors. It is noted that for a Gi coupled GPCR, when this approach is used, an inverse agonist of the Target GPCR will increase the cAMP signal and an agonist will decrease the cAMP signal.

On day one, $4 \times 10^6$ 293 cells per 10 cm dish will be plated out. On day two, two reaction tubes will be prepared (the proportions to follow for each tube are per plate): tube A will be prepared by mixing 21 g DNA of each receptor transfected into the mammalian cells, for a total of 4 µg DNA (e.g., pCMV vector; pCMV vector with mutated THSR (TSHR-A623I); TSHR-A623I and the Target GPCR, etc.) in 0.5 ml serum free DMEM (Irvine Scientific, Irvine, Calif.); tube B will be prepared by mixing 24 µl lipofectamine (Gibco BRL) in 0.5 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 5 ml serum free DMEM. 1.0 ml of the transfection mixture will then be added to the cells, followed by incubation for 4 hrs at 37° C./5% $CO_2$. The transfection mixture will then be removed by aspiration, followed by the addition of 10 ml of DMEM/10% Fetal Bovine Serum. Cells will then be incubated at 37° C./5% $CO_2$. After approximately 24-48 hr incubation, cells will then be harvested and utilized for analysis.

A Flash Plate™ Adenylyl Cyclase kit (New England Nuclear; Cat. No. SMP0004A) is designed for cell-based assays, but can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty-four to forty-eight hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) will be prepared and maintained in accordance with the manufacturer's instructions. Assay Buffer should be prepared fresh for screening and contained 50 µl of Stimulation Buffer, 3 µl of test compound (12 µM final assay concentration) and 50 µl cells, Assay Buffer can be stored on ice until utilized. The assay can be initiated by addition of 50 µl of cAMP standards to appropriate wells followed by addition of 50 µl of PBS to wells H-11 and H12. Fifty µl of Stimulation Buffer will be added to all wells. Selected compounds (e.g., TSH) will be added to appropriate wells using a pin tool capable of dispensing 3 µl of compound solution, with a final assay concentration of 12 µM test compound and 100 µl total assay volume. The cells will then be added to the wells and incubated for 60 min at room temperature. 100 µl of Detection Mix containing tracer cAMP will then be added to the wells. Plates are then incubated additional 2 hours followed by counting in a Wallac MicroBeta scintillation counter. Values of cAMP/well will then be extrapolated from a standard cAMP curve which is contained within each assay plate.

4. Reporter-Based Assays a. Cre-Luc Reporter Assay (Gs-Associated Receptors)

293 and 293T cells are plated-out on 96 well plates at a density of $2 \times 10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS are added to each well after a 4 hr incubation in a cell culture incubator. The following day the transfected cells are changed with 200 µl/well of DMEM with 10% FCS. Eight (8)

hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue #219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP (secreted alkaline phosphatase expression plasmid; alkaline phosphatase activity is measured in the media of transfected cells to control for variations in transfection efficiency between samples).

c. Srf-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with, e.g. 1 µM, test compound. Cells are then lysed and assayed for luciferase activity using a Luclite™ Kit (Packard, Cat. #6016911) and "Trilux 1450 Microbeta" liquid scintillation and luminescence counter (Wallac) as per the manufacturer's instructions. The data can be analyzed using GraphPad Prisms 2.0a (GraphPad Software Inc.).

d. Intracellular IP3 Accumulation Assay (Gq-Associated Receptors)

On day 1, cells comprising the receptors (endogenous or non-endogenous) can be plated onto 24 well plates, usually $1 \times 10^5$ cells/well (although his number can be optimized. On day 2 cells can be transfected by first mixing 0.25 µg DNA in 50 µl serum free DMEM/well and 2 µl lipofectamine in 50 µl serum free DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3H$-myo-inositol. Briefly, the media is removed and the cells are washed with 0.5 ml PBS. Then 0.5 ml inositol-free/serum free media (GIBCO BRL) is added/well with 0.25 µCi of $^3H$-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 µM pargyline 10 mM lithium chloride or 0.4 ml of assay medium and optionally 50 µl of test compound to final concentration of 10 µM. The cells are then incubated for 30 min at 37° C. The cells are then washed with 0.5 ml PBS and 200 µl of fresh/ice cold stop solution (1M KOH; 18 nM Na-borate; 3.8 mM EDTA) is added/well. The solution is kept on ice for 5-10 min or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 4

Fusion Protein Preparation a. GPCR:Gs Fusion Construct

The design of the GPCR-G protein fusion construct can be accomplished as follows: both the 5' and 3' ends of the rat G protein Gsα (long form; Itoh, H. et al., 83 PNAS 3776 (1986)) are engineered to include a HindIII (5'-AAGCTT-3') sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the Gsα sequence is determined after subcloning into pcDNA3.1(−). The modified pcDNA3.1(−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

A Gq(del)/Gi fusion construct is a chimeric G protein whereby the first six (6) amino acids of the Gq-protein α-subunit ("Gαq") are deleted and the last five (5) amino acids at the C-terminal end of Gαq are replaced with the corresponding amino acids of the Gαi subunit. A Gq(del)/Gi fusion construct will force an endogenous Gi coupled receptor to couple to its non-endogenous G protein, Gq (in the form of Gq(del)/Gi), such that the second messenger, for example, inositol triphosphate or diacylglycerol or $Ca^{2+}$, can be measured in lieu of cAMP production.

The Gq(del)/Gi fusion construct was designed as follows: the N-terminal six (6) amino acids (amino acids 2 through 7, having the sequence of TLESIM (SEQ ID NO: 9) of the Gαq-subunit were deleted and the C-terminal five (5) amino acids, having the sequence EYNLV (SEQ ID NO: 10) were replaced with the corresponding amino acids of the Gαi Protein, having the sequence DCGLF (SEQ ID NO: 11). This fusion construct was obtained by PCR using the following primers:

```
                                                   (SEQ ID NO: 12)
5'-gatcaagcttcCATGGCGTGCTGCCTGAGCGAGGAG-3'
and (SEQ ID NO: 13)
5'-gatcggatccTTAGAACAGGCCGCAGTCCTTCAGGTTCA
GCTGCAGGATGGTG-3'
``` and Plasmid 63313 (ATCC® Number 63313) which contains the mouse Gαq-wild-type version with a hemagglutinin tag as a template. Nucleotides in lower case include cloning sites for HindIII/BamHI and spacers.

TaqPlus Precision DNA polymerase (Stratagene) was utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product was cloned into a pCRII-TOPO vector (Invitrogen) and sequenced using the ABI Big Dye Terminator kit (P. E. Biosystems). Inserts from a TOPO clone containing the sequence of the fusion construct was shuttled into the expression vector pcDNA3.1(+) at the HindIII/BamHI site by a 2 step cloning process. See, SEQ ID NO: 14 for the nucleic acid sequence and SEQ ID NO: 15 for the encoded amino acid sequence of Gq(del)/Gi construct.

Example 5

[$^{35}$S]GTPγS Assay

1. Membrane Preparation

In some embodiments membranes comprising a Target GPCR and for use in the identification of candidate compounds as, e.g., inverse agonists, agonists, or antagonists, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM MgCl$_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

2. Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 μl Binding Buffer. Thereafter, 10 μl of Bradford Protein Standard (1 mg/ml) will be added to each tube, and 10 μl of membrane Protein will then be added to just one tube (not the blank). Thereafter, 200 μl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595 nm.

3. Identification Assay a. Materials

GDP Buffer consists of 37.5 ml Binding Buffer and 2 mg GDP (Sigma, cat. no. G-7127), followed by a series of dilutions in Binding Buffer to obtain 0.2 μM GDP (final concentration of GDP in each well was 0.1 μM GDP); each well comprising a candidate compound, has a final volume of 200 μl consisting of 100 μl GDP Buffer (final concentration, 0.1 μM GDP), 50 μl Membrane Protein in Binding Buffer, and 50 μl [$^{35}$S]GTPγS (0.6 nM) in Binding Buffer (2.5 μl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 μg/well). Thereafter, 100 μl GDP Buffer is added to each well of a Wallac Scintistrip™ (Wallac). A 5 ul pin-tool will then be used to transfer 5 μl of a candidate compound into such well (i.e., 5 μl in total assay volume of 200 μl is a 1:40 ratio such that the final screening concentration of the candidate compound is 10 μM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 μl of Membrane Protein will be added to each well (a control well comprising membranes without the Target GPCR was also utilized), and pre-incubated for 5-10 minutes at room temperature. Thereafter, 50 μl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

Example 6

Cyclic AMP Assay

Another assay approach for identifying candidate compounds as, e.g., inverse agonists, agonists, or antagonists, is accomplished by utilizing a cyclase-based assay. In addition to so identifying candidate compounds, this assay approach can be utilized as an independent approach to provide confirmation of the results from the [$^{35}$S]GTPγS approach as set forth in Example 5, supra.

A modified Flash Plate™ Adenylyl Cyclase kit (New England Nuclear; Cat. No. SMP004A) is preferably utilized for identification of candidate compounds as modulators of a Target GPCR in accordance with the following protocol.

Cells transfected with the Target GPCR are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 0.1 mM MgCl$_2$, to yield a final protein concentration of 0.60 mg/ml (the resuspended membranes are placed on ice until use).

cAMP standards and Detection Buffer (comprising 2 μCi of tracer {[$^{125}$I]cAMP (100 μl) to 11 ml Detection Buffer] are prepared and maintained in accordance with the manufacturer's instructions. Assay Buffer is prepared fresh for screening and contains 20 mM HEPES, pH 7.4, 10 mM MgCl$_2$, 20 mM phosphocreatine (Sigma), 0.1 units/ml creatine phosphokinase (Sigma), 50 μM GTP (Sigma), and 0.2 mM ATP (Sigma); Assay Buffer is then stored on ice until utilized.

Candidate compounds are added, preferably, to e.g. 96-well plate wells (3 μl/well; 12 μM final assay concentration), together with 40 μl Membrane Protein (30 μg/well) and 50 μl of Assay Buffer. This admixture was then incubated for 30 minutes at room temperature, with gentle shaking.

Following the incubation, 100 μl of Detection Buffer is added to each well, followed by incubation for 2-24 hours. Plates are then counted in a Wallac MicroBeta™ plate reader using "Prot. #31" (as per manufacturer's instructions).

By way of example and not limitation, an illustrative screening assay plate (96 well format) result obtained is presented in FIG. 1. Each bar represents the result for a compound that differs in each well, the "Target GPCR" being a Gsα Fusion Protein construct of an endogenous, constitutively active Gs-coupled GPCR unrelated to GPR101. The results presented in FIG. 1 also provide standard deviations based upon the mean results of each plate ("m") and the mean plus two arbitrary preference for selection of inverse agonists as "leads" from the primary screen involves selection of candidate compounds that that reduce the percent response by at least the mean plate response, minus two standard deviations. Conversely, an arbitrary preference for selection of agonists as "leads" from the primary screen involves selection of candidate compounds that increase the percent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, it is possible to ascertain compounds that are able to reduce the functional activity of this receptor (Compound A) as well as increase the functional activity of the receptor (Compound B).

Example 7

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at 5.5×10$^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 μl DMSO and 467 μl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 μl of 4 μM Fluo4-AM/ 2.5 mM Probenicid (Sigma, #P8761)/20 mM HEPES/complete medium at pH 7.4. Incubation at 37° C./5% CO$_2$ is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% CO$_2$ for 60 min.

FLIPR (Fluorometric Imaging Plate Reader; Molecular Device) is programmed to add 50 μl candidate compound on the 30th second and to record transient changes in intracellular calcium concentration ([Ca$^{2+}$]) evoked by the candidate compound for another 150 seconds. Total fluorescence change counts are used to determine agonist activity using the FLIPR software. The instrument software normalizes the fluorescent reading to give equivalent initial readings at zero.

By way of illustration and not limitation, the skilled artisan would appreciate that a candidate compound can be screened as an antagonist of the receptor by assessing its ability to inhibit the transient increase in intracellular ([Ca$^{2+}$]) evoked by subsequent contact with a known agonist.

In some embodiments, the cells comprising Target Receptor further comprise Gα15, Gα16, or Gq(del)/Gi chimeric G protein.

Although the foregoing provides a FLIPR assay for agonist activity using stably transfected cells, a person of ordinary skill in the art would readily be able to modify the assay in order to characterize antagonist activity. The person of ordinary skill in the art would also readily appreciate that, alternatively, transiently transfected cells could be used.

Example 8

MAP Kinase Assay

MAP kinase (mitogen activated kinase) may be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then be aspirated through the filter, which retains, the phosphorylated myelin basic protein. The filter is washed and counted for $^{32}$P by liquid scintillation counting.

Example 9

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods can be followed according to the disclosure of U.S. Pat. No. 5,462,856 and U.S. Pat. No. 6,051, 386. These patent disclosures are herein incorporated by reference in their entirety.

The cells are plated in e.g. 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7X L-15 (Gibco). After one hour, the cells in serum-free media remain in a pigment-dispersed state while the melatonin-treated cells are in a pigment-aggregated state. At this point, the cells are treated with a dose response of a test/candidate compound. If the plated GPCRs bind to the test/candidate compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Example 10

Yeast Reporter Assay for GPR101 Modulator (e.g., Agonist) Activity

The yeast cell-based reporter assays have previously been described in the literature (e.g., see Miret et al, J Biol Chem (2002) 277:6881-6887; Campbell et al, Bioorg Med Chem Lett (1999) 9:2413-2418; King et al, Science (1990) 250:121-123; WO 99/14344; WO 00/12704; and U.S. Pat. No. 6,100, 042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Ste3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic readout.

Yeast cells are transformed by an adaptation of the lithium acetate method described by Agatep et al (Agatep et al, 1998, Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 µg), 2 µg of each of two Fus1p-LacZ reporter plasmids (one with URA selection marker and one with TRP), 2 µg of GPR101 (e.g., human receptor) in yeast expression vector (2 µg origin of replication) and a lithium acetate/polyethylene glycol/TE buffer is pipetted into an Eppendorf tube. The yeast expression plasmid containing the receptor/no receptor control has a LEU marker. Yeast cells are inoculated into this mixture and the reaction proceeds at 30° C. for 60 min. The yeast cells are then heat-shocked at 42° C. for 15 min. The cells are then washed and spread on selection plates. The selection plates are synthetic defined yeast media minus LEU, URA and TRP (SD-LUT). After incubating at 30° C. for 2-3 days, colonies that grow on the selection plates are then tested in the LacZ assay.

In order to perform fluorimetric enzyme assays for β-galactosidase, yeast cells carrying the subject GPR101 receptor are grown overnight in liquid SD-LUT medium to an unsaturated concentration (i.e. the cells are still dividing and have not yet reached stationary phase). They are diluted in fresh medium to an optimal assay concentration and 90 μl of yeast cells are added to 96-well black polystyrene plates (Costar). Test compounds, dissolved in DMSO and diluted in a 10% DMSO solution to 10× concentration, are added to the plates and the plates placed at 30° C. for 4 h. After 4 h, the substrate for the β-galactosidase is added to each well. In these experiments, Fluorescein di (β-D-galactopyranoside) is used (FDG), a substrate for the enzyme that releases fluorescein, allowing a fluorimetric read-out. 20 μl per well of 500 μM FDG/2.5% Triton X100 is added (the detergent is necessary to render the cells permeable). After incubation of the cells with the substrate for 60 min, 20 μl per well of 1M sodium carbonate is added to terminate the reaction and enhance the fluorescent signal. The plates are then read in a fluorimeter at 485/535 nm.

An increase in fluorescent signal in GPR101-transformed yeast cells over that in yeast cells transformed with empty vector and over the signal obtained in the presence of 1% DMSO without compound is indicative of a test compound being a compound that stimulates GPR101 receptor functionality, e.g., an agonist or a partial agonist of the receptor.

A decrease in fluorescent signal in GPR101-transformed yeast cells over that in yeast cells transformed with empty vector and over the signal obtained in the presence of 1% DMSO without compound is indicative of a test compound being a compound that inhibits GPR101 receptor functionality, e.g., an inverse agonist or an antagonist of the receptor.

Example 11

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

In other aspect, a test compound can be radiolabeled and shown to be a ligand of a subject GPCR of the invention by evaluating its ability to bind to a cell comprising the subject GPCR or to membrane comprising the subject GPCR.

A level of specific binding of the radiolabeled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabeled known ligand.

Example 12

Endogenous GPR101 Exhibits Constitutive Activity for Increasing a Level of Intracellular cAMP Human HEK293 cells were transiently transfected with either pCMV vector or an amount of a cDNA plasmid encoding endogenous human GPR101. Transfection was carried out using Lipofectamine (Invitrogen). Forty-eight hours after transfection, whole cell cAMP was determined using the Adenylyl Cyclase Flashplate Assay kit from Perkin Elmer catalog #:SMP004B], as described below.

The transfected cells were placed into anti-cAMP antibody-coated wells. All conditions were tested in triplicate. A Detection Mix (provided in the Perkin Elmer kit) containing $^{125}$I-cAMP was added to each well and the plate was allowed to incubate for an hour at room temperature. The wells were then aspirated to remove unbound $^{125}$I-cAMP. Bound $^{125}$I-cAMP was detected using a Wallac Microbeta Counter. The amount of cAMP in each sample was determined by comparison to a standard curve, obtained by placing known concentrations of cAMP in some wells on the plate. Results are presented in FIG. 2.

Figure 2:
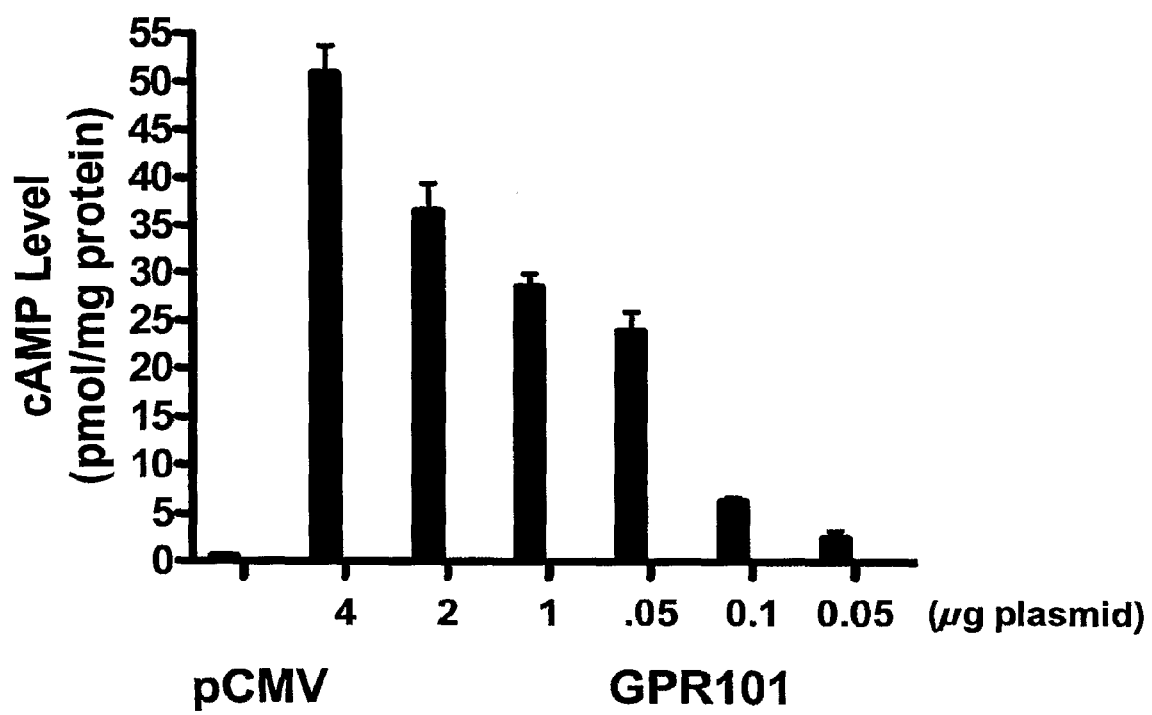
FIG. 2. GPR101 exhibits detectable constitutive activity for increasing a level of intracellular cAMP. (See, Example 12.)

As shown in FIG. 2, endogenous human GPR101 is detectably constitutively active, exhibiting dose-dependent constitutive activity for increasing a level of intracellular cAMP, consistent with being coupled to Gs.

Example 13

Expression of GPR101 in RAT

A. RT-PCR Analysis of GPR101 Expression in Rat Tissues

Expression of GPR101 in rat tissue was investigated by RT-PCR. Rat RNA isolated from various tissues was obtained from Zyagen (San Diego, Calif.). cDNA was synthesized from total RNA using iScript cDNA synthesis kit from Bio-Rad, following the manufacturer's protocol. GPR101 expression was evaluated using RT-PCR using the following primers:

```
5'-CTTTCTTCTGGCCTCTCAACATCC-3'    (SEQ ID NO: 16;
                                   sense)
and
5'-CAGAAGGCATTACGGTCATCAAAA-3'    (SEQ ID NO: 17;
                                   antisense).
```

Figure 3A:
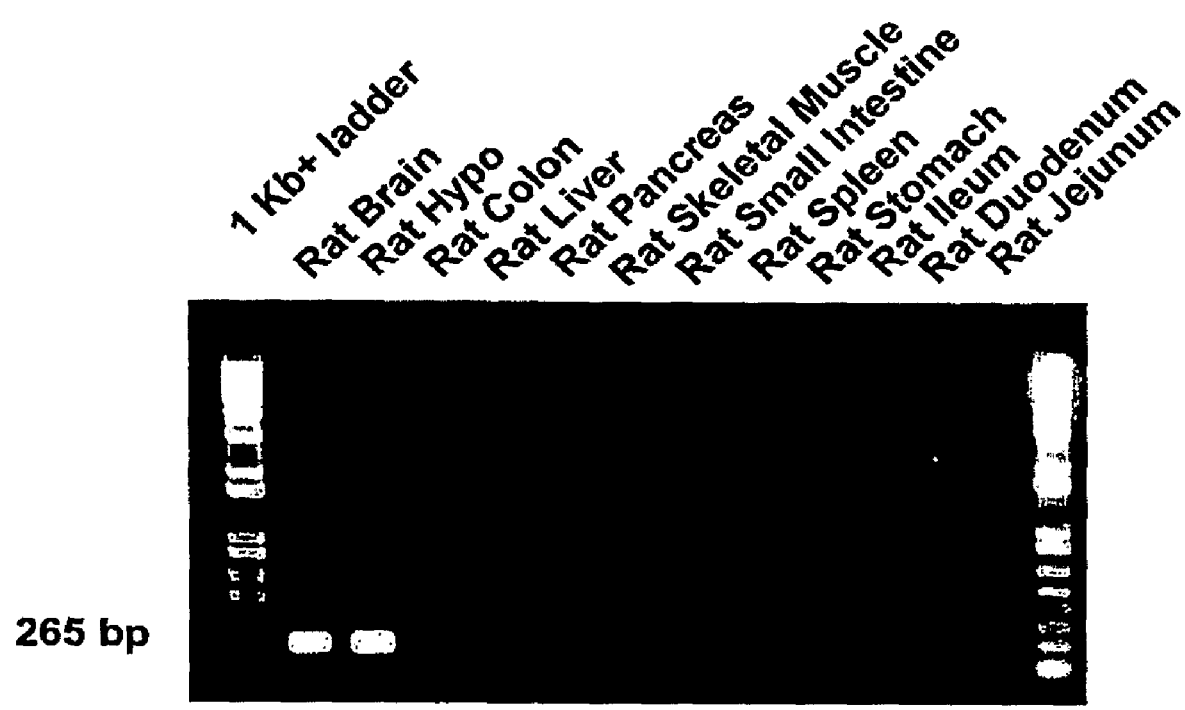
FIGS. 3A to 3C. A. RT-PCR analysis of GPR101 expression in rat tissues. B. In situ hybridization histochemical analysis of GPR101 expression in rat brain, including hypothalamic arcuate nucleus. C. Immunohistochemical analysis of GPR101 expression in rat brain, including hypothalamic arcuate nucleus. (See, Example 13.)

Results are presented in FIG. 3A. The position of the expected 265 bp amplification product is indicated. Rat GPR101 was found to be selectively expressed in brain, including hypothalamus.

B. In-Situ Hybridization Histochemical Analysis of GPR101 Expression in Rat Brain, Including Hypothalamic Arcuate Nucleus Expression of GPR101 in rat brain was investigated by in-situ hybridization histochemistry. In-situ hybridization histochemistry was carried out as described below (see, e.g., Bagnol et al, J Neurosci (1999) 19:RC26 (1-7)).

In situ hybridization was carried out on 300- to 350-g male Sprague-Dawley rats obtained from Charles River Laboratories, Inc. (Wilmington, Mass.). Rats were killed by rapid decapitation. Brains were remove and frozen in isopentane (−40° C.), and stored at −80° C. Serial 10-µm sections through hypothalamus and poms were prepared on a cryostat, thaw-mounted onto polylysine-subbed slides, and stored at −80° C. until processing.

Sense and antisense $^{33}$P-radiolabelled probes were generated by in vitro transcription by incubating linearized plasmid (plasmid into which rat cDNA having SEQ ID NO: 5 had been inserted) in transcription buffer containing RNasin (40 units), DTT (2 mM), ATP, CTP and GTP (0.33 mM), [α-$^{33}$P]-UTP (Perkin Elmer, 50 µCi, NEG307 H001MC) and the appropriate polymerase (T7, 50 units, or T3, 20 units). Probes were treated with DNase, purified by ethanol precipitation, and resuspended in 2× hybridisation mix (8×SET, 2×Denhardt's, 0.4% SDS, 200 mM dithiothreitol (DTT), 500 ug/ml tRNA, 50 ug/ml polyA, and 50 ug/ml polyC).

Tissue sections were removed from the freezer and allowed to air-dry for 30 min. Sections were subsequently fixed in 4% paraformaldehyde in phosphate buffer (0.1 M, pH 7.4) for 30 min at room temperature, rinsed 3 times in 1×PBS, acetylated in 0.1M triethanolamine (TEA), pH 8.0 for 2 min, then incubated briefly in the same buffer containing 0.25% acetic anhydride. Slides were then rinsed for 5 minutes in 1×PBS and dehydrated through a graded alcohol series and air-dried. Radiolabelled probes were diluted in 2× hybridization buffer to yield an approximate concentration of 8×10$^6$ cpm per slide. Dextran sulphate/formamide (20%) was added to give a 1:1 ratio with 2× hybridization buffer. Diluted probes were placed on slides, coverslipped, and incubated at 55° C. for 16-18 hours in plastic trays humidified with 1×PBS. Coverslips were floated off with 1 mM DTT/4×SSC (600 mM sodium chloride and 60 mM sodium citrate, pH 7.2), and sections were subsequently washed once in 4×SSC for 10 min, incubated in ribonuclease A (200 ug/ml) for 60 min at room temperature on a rocker, then rinsed in 2×, 1×, and 0.5×SSC for 5 minutes each. Sections were washed to a final stringency of 0.1×SSC at 65° C. for 1 hour, then washed twice in 0.1× SSC to cool them to room temperature. Slides were then dehydrated through graded alcohols (70% and 95%) containing 300 mM ammonium acetate, then 100% ethanol, exposed to x-ray sensitive film (Bio-Max, Kodak, Eastman Kodak Co., Rochester, N.Y.) for 2-7 days, dipped in photographic emulsion (IB1654433, Kodak), dried, and stored in slide boxes with desiccant at 4° C. for 2-4 weeks depending on the level of expression. After development of the dipped slides according to the manufacturer's recommendations (Kodak D19), the sections were washed extensively in water, stained with thionin, dehydrated in alcohol, and mounted in a xylene-based mounting medium for microscopy. Radioactive probes were visualized under darkfield by silver grain distribution.

Figure 3B:
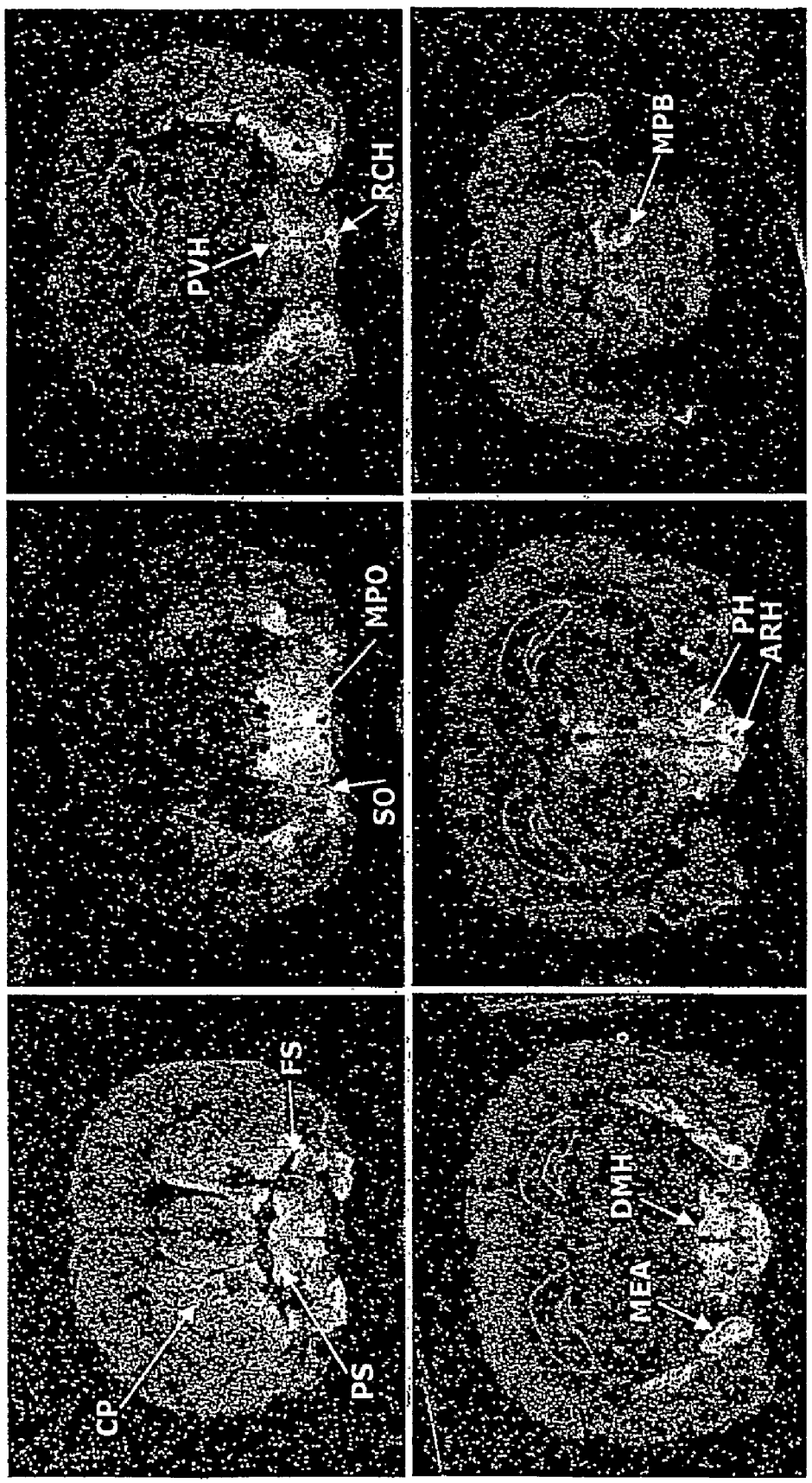

Results using labeled antisense probe are shown in FIG. 3B. Expression of GPR101 was detected in Caudate-Putamen (CP); fundus of the striatum (FS); Parastrial nucleus (PS); supraoptic nucleus (SO); medial preoptic nucleus (MPO); paraventricular nucleus hypothalamus (PHV); retrochiasmatic area (RCH); dorsomedial nucleus hypothalamus (DMH); arcuate nucleus hypothalamus (ARH); posterior hypothalamic nucleus (PH); medial nucleus amygadala (MEA); and medial parabrachial nucleus (MPB). Specificity of hybridization was confirmed by control experiment using sense probe; no specific hybridization signals were observed under this condition.

C. Immunohistochemical Analysis of GPR101 Expression in Rat Brain, Including Hypothalamic Arcuate Nucleus Expression of GPR101 in rat brain was investigated by immunohistochemistry, using protein A affinity-purified rabbit anti-peptide polyclonal antibody specific for the carboxy terminus of rat, mouse and human GPR101 receptor. Immunohistochemistry was carried out as described below (see, e.g., Wilson et al, Endocrinology (1999) 140:2387-2397).

Immunohistochemistry was carried out on 300- to 350-g male Sprague-Dawley rats obtained from Charles River Laboratories, Inc. (Wilmington, Mass.). For tissue preparation, rats were anesthetized, then perfused with 250 ml 0.9% NaCl and 2.2% sodium nitrite, followed by 500 ml 4% paraformaldehyde in 0.1 M phosphate buffer. Brains were removed, incubated in the same fixative for 2 h at 4° C., then cryoprotected with a 20% phosphate-buffered saccharose solution overnight at 4° C. Serial sections through hypothalamus prepared by cryostat (30 µm) were stored in a cryopreservative solution (30% sucrose and 30% ethylene glycol in 50 mM potassium PBS) at −20° C. until use.

For immunohistochemistry, free-floating sections were washed in 50 mM potassium PBS (KBPS), incubated with 0.3% hydrogen peroxide (30 min), rinsed in 50 mM KBPS, and incubated with blocking solutions (Vector Laboratories, Burlingame, Calif.) for 15 min at a 1:5 dilution. Sections were incubated in antibody diluent composed of 50 mM KPBS, 0.4% Triton X-100, 1% BSA, and 1% normal goat serum for 30 min at 22° C., then transferred to GPR101 antibody. After 48 h at 4° C., tissues were washed in 50 mM KPBS with 0.02% Triton X-100, incubated with biotinylated goat anti-rabbit IgG (Vector Laboratories, Inc.) for 1 h at 22° C., then incubated with avidin-biotin complex coupled to horseradish peroxidase for 1 h at 22° C. The horseradish peroxidase reaction product was visualized with 0.04% 3,3'-diaminobenzidine tetrahydrochloride, 2.5% nickel chloride, and 0.01% $H_2O_2$, dissolved in 0.1 M sodium acetate. The reaction was terminated by two consecutive 0.9% NaCl washes, after which free floating tissues were mounted on gelating-coated slides. Finally, the sections were treated with graded alcohol and xylene, and then coverslipped with Permount.

Figure 3C:
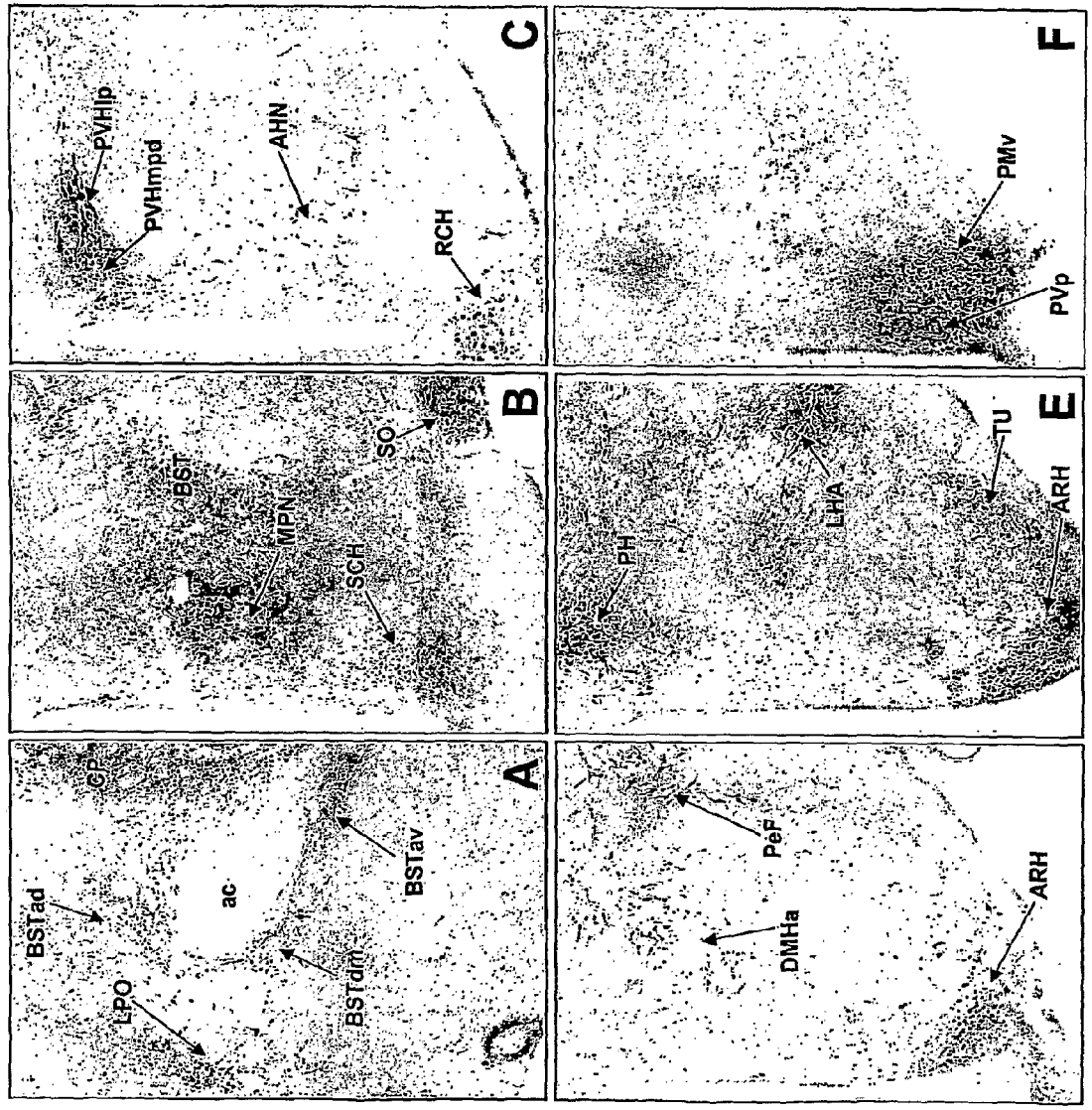

Results are shown in FIG. 3C. Expression of GPR10 was detected in Caudate-Putamen (CP); bed nucleus of the stria terminalis (BSTad), anterior division, anterolateral area; bed nucleus of the stria terminalis (BSTdm), anterior division, dorsomedial area; bed nucleus of the stria terminalis (BSTav), anterior division, anteroventral area; anterior commissure (ac); lateral preoptic area (LPO); bed nucleus of the stria terminalis (BST); medial preoptic nucleus (MPN); suprachiasmatic nucleus (SCH); supraoptic nucleus (SO); retrochiasmatic area (RCH); anterior hypothalamic nucleus (AHN); paraventricular nucleus hypothalamus (PHVmpd), medial parvicellular part, ventral zone; paraventricular nucleus hypothalamus (PHVlp), lateral parvicellular part; dorsomedial nucleus hypothalamus (DMHa), anterior part; arcuate nucleus hypothalamus (ARH); Perifornical area (PeF); Lateral hypothalamic area (LHA); Tuberal nucleus (TU); posterior hypothalamic nucleus (PH); Posterior periventricular nucleus hypothalamus (PVp); and Ventral premammillary nucleus (PMv). Specificity of immunostaining was confirmed by control experiment using blocking immunizing peptide.

Example 14

Selective Expression of GPR101 in POMC Neurons Over NPY/AgRP Neurons in Rat Hypothalamic Arcuate Nucleus Expression of GPR101 by POMC neurons and by NPY/AgRP neurons in hypothalamic arcuate nucleus was investigated by in situ hybridization, using radiolabeled antisense probe for GPR101 in combination with a digoxigenin (Dig)-labeled antisense probe for POMC or for NPY. The rat GPR101 probe corresponded to the nucleotide sequence of SEQ ID NO: 5. The rat POMC probe corresponded to rat POMC coding sequence (see, e.g., GenBank® Accession No. BC058443). The rat NPY probe corresponded to rat NPY coding sequence (see, e.g., GenBank® Accession No. NM_012614). In situ hybridization was carried out essentially as described below (see, e.g., Wilson et al, Endocrinology (1999) 140:2387-2397).

Rat were killed by rapid decapitation 1-2 h after initiation of the light cycle. Brains were removed, frozen in isopentene (−40° C.), and stored at −80° C. Serial 10-μm sections from hypothalamic arcuate nucleus were prepared on a cryostat, thaw-mounted onto polylysine-subbed slides, and stored at −80° C. until processing.

Sense and antisense $^{33}$P-radiolabelled GPR101 probe was generated by in vitro transcription by incubating linearized plasmid in transcription buffer containing RNasin (40 units), DTT (2 mM), ATP, CTP and GTP (0.33 mM), [α-$^{33}$P]-UTP (Perkin Elmer, 50 μCi, NEG307 H001MC) and the appropriate polymerase (T7, 50 units, or T3, 20 units). Probes were treated with DNase, purified by ethanol precipitation, and resuspended in 2× hybridisation mix (8×SET, 2×Denhardt's, 0.4% SDS, 200 mM dithiothreitol (DTT), 500 ug/ml tRNA, 50 ug/ml polyA, and 50 ug/ml polyc). Digoxigenin-labeled probes were generated in a similar fashion, but with 140-320 μM digoxigenin-UTP (Boehringer Mannheim, Indianapolis, Ind.); the reaction was supplemented with conjugated UTP to a final concentration of 400 μM. RNA probes were separated from free nucleotides on Sephadex G-50 columns. The specificity of hybridization was confirmed by control experiments using sense probes. No specific hybridization was observed using sense probes.

Before hybridization, sections were air dried for 15 min and fixed for 1 h at 22° C. in 4% paraformaldehyde in PBS. The sections were rinsed three times in 2×SSC (300 mM sodium chloride and 30 mM sodium citrate, pH 7.2) and once in distilled water (5 min/rinse), then treated with 0.1 M triethanolamine, pH 8.0, and acetic anhydride (0.25%) for 10 min at 22° C. Sections were rinsed in water, dehydrated through graded alcohols, and allowed to air-dry.

Radiolabeled and digoxigenin-labeled probes were diluted together in hybridization buffer (50% formamide, 10% dextran sulfate, 3×SSC, 50 mM sodium phosphate buffer (pH 7.4), 1×Denhardt's solution, 0.1 mg/ml yeast transfer RNA, and 10 mM dithiothreitol) to yield an approximate concentration of 2-2.5×10$^6$ cpm/70 μl. Appropriate dilutions for nonradioactive probes were estimated from pilot experiments. Diluted probe (70 μl) was placed on each slide, and the sections were coverslipped. Slides were placed in plastic trays lined with filter paper dampened with 50% formamide-50% water. Trays were sealed and incubated at 55° C. for 16 h. Coverslips were floated off in 2×SSC, and sections were rinsed three times in 2×SSC, incubated in ribonuclease A (200 μg/ml) for 60 min at 37° C., then rinsed in 2, 1, 0.5, and 0.1×SSC. Sections were washed to a final stringency of 0.1× SSC at 70° C. for 60 min, then allowed to cool to room temperature.

After hybridization and washing, sections were processed for detection of the digoxigenin-labeled probe by rinsing in 0.1 M phosphate buffer containing 150 mM NaCl, pH 7.5, and incubating in blocking solution (0.1 M phosphate buffer containing 150 mM NaCl and 0.5% casein, pH 7.5) for 2-4 h at room temperature. Sections were incubated for 2 h at room temperature with sheep antidigoxigenin antibody conjugated to alkaline phosphatase (Fab fragment, Boehringer Mannheim), diluted 1:300 in blocking solution. Sections were then washed three times in 0.1 M phosphate buffer, twice in Tris-buffered saline, and once in alkaline substrate buffer (100 mM Tris, 150 mM NaCl, and 50 mM MgCl$_2$, pH 9.5) before carrying out the color reaction in alkaline substrate buffer containing 5% polyvinyl alcohol, 0.025% levanisole, 0.45% 4-nitro blue tetrazodium chloride, and 0.35% 5-bromo-4-chloro-3-indoyl-phosphate, 4-toluidine salt. Sections were incubated in the dark for 12-24 h at room temperature and examined under a microscope to determine reaction completion. Slides were then washed extensively in water, incubated in 0.1 M glycine and 0.5% Triton X-100, pH 2.2, for 10 min at room temperature to remove the antibody, and then washed in water. Finally, sections were fixed in 2.5% glutaraldehyde for 1 h, washed in water, and air-dried. Sections were initially exposed to x-ray film for 1-7 days, then dipped in emulsion (KD-5, Ilford, Paramus, N.J.) and stored in light-tight boxes for 7-35 days at 4° C. After development (Kodak D-19, Eastman Kodak Co., Rochester, N.Y.) of dipped slides, sections were generally dehydrated in alcohols and mounted in a xylene-based mounting medium (Permount, Fisher Scientific, Fairlawn, N.Y.) for photomicrography.

Images of the distribution of GPR101 and either POMC or NPY mRNA-containing cells were obtained using an Olympus BX51 microscope connected to a videocamera (NTSC 750CE) using Stereoinvestigator® v6.55.2 software (Microbrightfield, Vt.). Nonradioactive riboprobes were visualized under brightfield as a purple precipitate, and radioactive probes were visualized under darkfield by silver grain distribution.

Figure 4A:
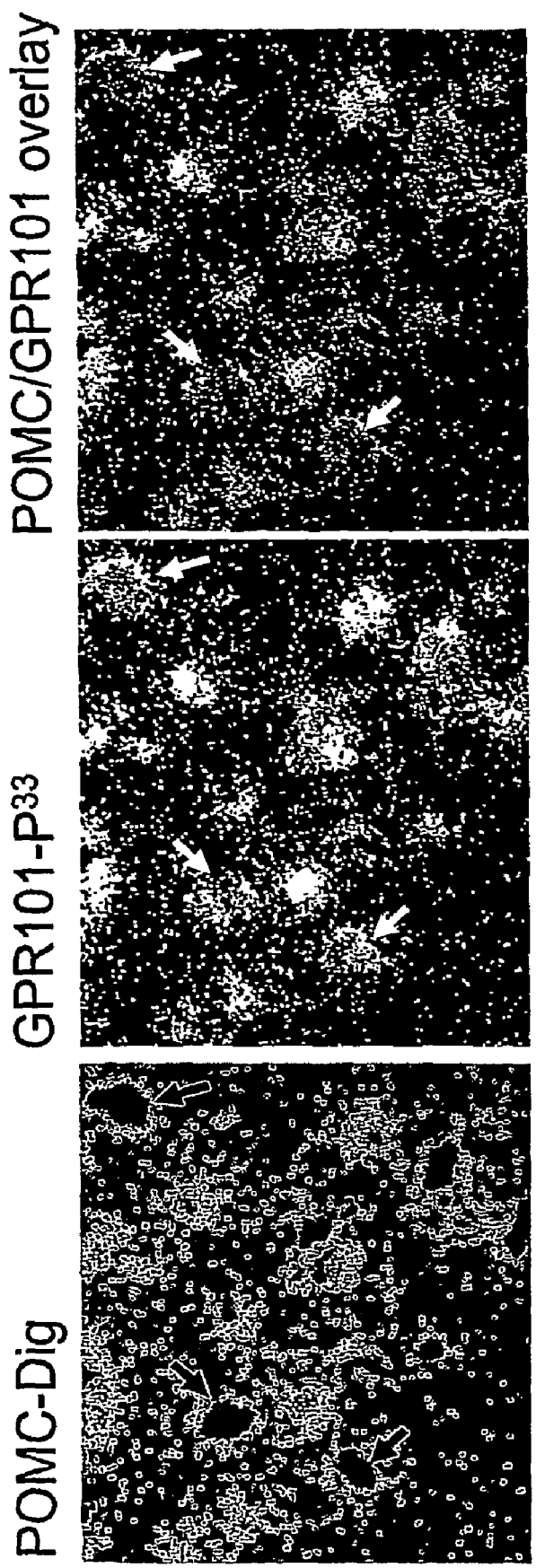
FIGS. 4A to 4B. A. Analysis of expression of GPR101 by POMC neurons of rat hypothalamic arcuate nucleus. B. Analysis of expression of GPR101 by NPY/AgRP neurons of rat hypothalamic arcuate nucleus. (See, Example 14.)
Figure 4B:
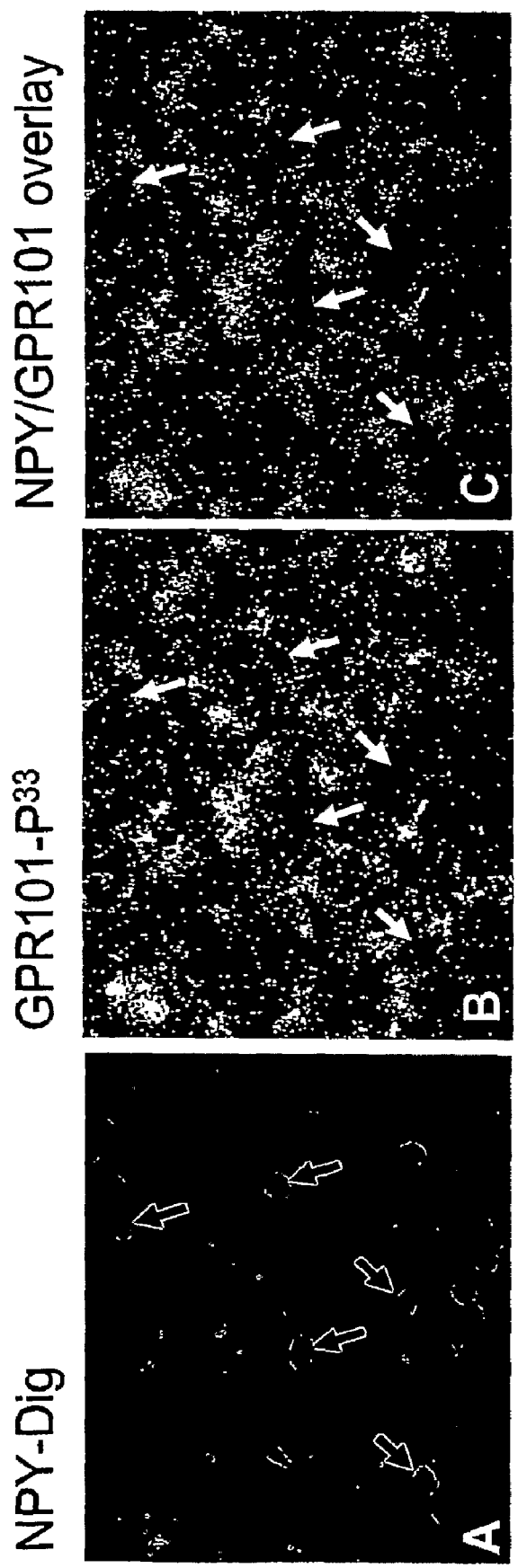

Results are presented in FIG. 4A (for POMC) and in FIG. 4B (for NPY). Whereas the vast majority of POMC neurons in hypothalamic arcuate nucleus were found to express GPR101 (FIG. 4A), there was essentially no detectable expression of GPR101 by NPY neurons (FIG. 4B). Table D below indicates the percentage of POMC neurons in rostrocaudal extension of rat hypothalamic arcuate nucleus expressing GPR101 as observed for a number of serial sections positioned 120 μM apart.

TABLE D

Expression of GPR101 by POMC Neurons in Rat Hypothalamic Arcuate Nucleus

| Section number | Total number of POMC neurons | Percentage of POMC neurons expressing GPR101 |
| --- | --- | --- |
| 233 | 9 | 100 |
| 243 | 95 | 91.6 |
| 253 | 78 | 98.7 |
| 263 | 124 | 96 |
| 273 | 113 | 90.3 |
| 283 | 130 | 88.5 |
| 293 | 93 | 88 |
| 303 | 125 | 89.6 |
| 313 | 71 | 95.8 |
| Total number of POMC neurons: 838 | | Average percentage: 93.2 |

Example 15

Taqman Analysis of GPR101 Expression in Mouse in Mouse Tissues

Expression of GPR101 in mouse tissue was investigated by TaqMan analysis. Mouse RNA isolated from various tissues (excluding C57Bl/6J brain and pancreas) was obtained from Zyagen (San Diego, Calif.). For quantitative PCR (qPCR) analysis, cDNA was synthesized from total RNA using iScript cDNA synthesis kit from BioRad, following the manufacturer's protocol. C57Bl/6J brain and pancreas were collected in-house and RNA extracted using Trizol standard procedure.

The qPCR reactions were performed using the ABI Prism 7900HT machine with the following temperatures and times: 50° C., 2 minutes; 95° C., 10 minutes; followed by 40 cycles of 95° C., 15 seconds and 60° C., 1 minute.

Primers and probe sequences used for qPCR analysis mouse GPR101 were as follows:

```
Forward Primer-
5'-TCAGGCTAGCAGCGCAAAG-3'          (SEQ ID NO: 18)

Reverse Primer-
5'-AATGTTGCACTGATTGGCATCT-3'       (SEQ ID NO: 19)

TaqMan MGB probe-6FAM-
5'-CAGACACCGGCCGC-3'               (SEQ ID NO: 20)
```

Figure 5:
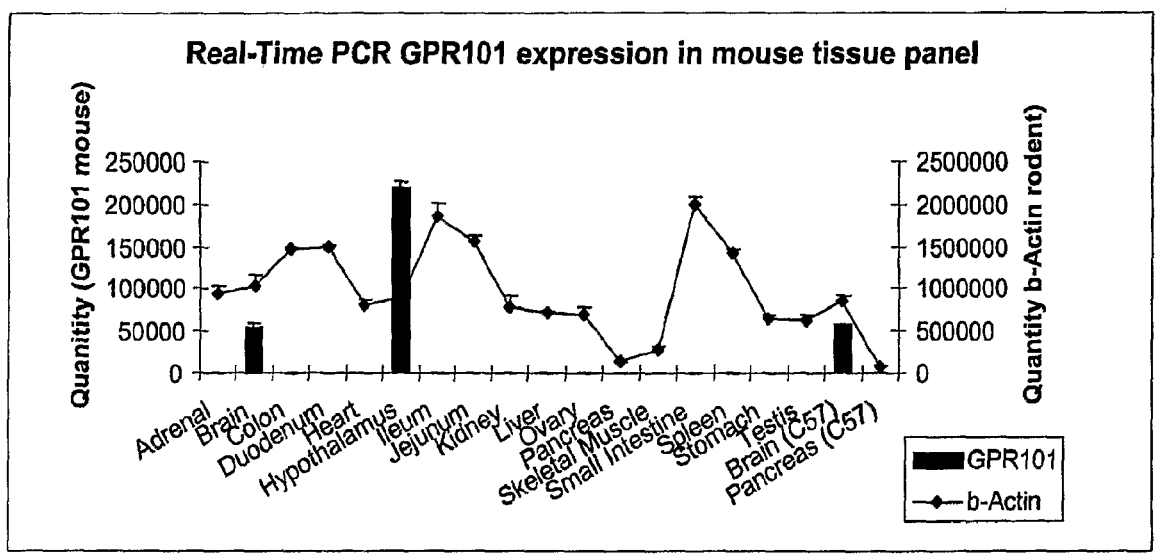
FIG. 5. TaqMan analysis of GPR101 expression in mouse tissues. (See, Example 15.)

Results are presented in FIG. 5. Mouse GPR101 was found to be selectively expressed in brain, including hypothalamus.

Example 16

Analysis of Expression of GPR101 in Human Hypothalamus

A. In Situ Hybridization Histochemical Analysis of Expression of GPR101 in Human Hypothalamus in Comparison to Expression of POMC and Corticotropin-Releasing Hormone (CRH)

The co-localization within human hypothalamus between GPR101 expression and POMC expression (POMC neurons) and CRH expression (CRH neurons) was investigated by in situ hybridization histochemical analysis carried out on serial sections prepared from hypothalamic tissue obtained from post mortem donors. Antisense probe was synthesized essentially as described in Example 13B. The human GPR101 probe corresponded to the nucleotide sequence of SEQ ID NO: 1. The human POMC probe corresponded to human POMC coding sequence (see, e.g., GenBank® Accession No. BC065832). The human CRH probe corresponded to human CRH coding sequence (see, e.g., GenBank® Accession No. BC011031).

The in situ hybridization histochemical analysis of serially sectioned human hypothalamus was carried out essentially as described in Example 13B. Radioactive probes were visualized under darkfield by silver grain distribution.

Figure 6A:
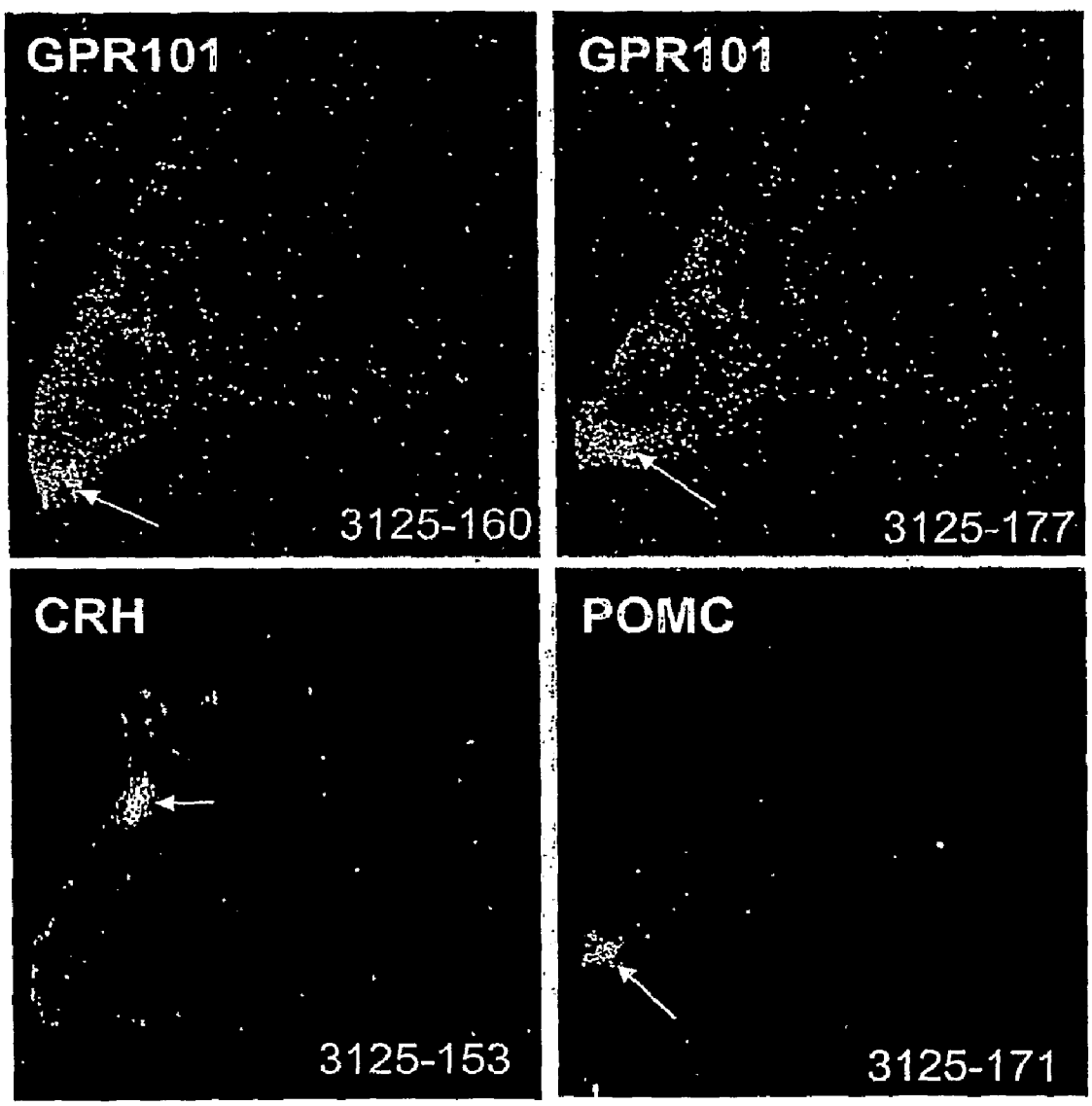
FIGS. 6A to 6B. A. In situ hybridization histochemical analysis of expression of GPR101 in human hypothalamus in comparison to expression of POMC and corticotropin-releasing hormone (CRH). B. Expression of GPR101 in POMC neurons in human hypothalamic arcuate nucleus. Arrows indicate POMC neurons within the field that express GPR101. The triangle indicates a POMC neuron within the field that does not detectably express GPR101. (See, Example 16.)

Representative results are shown in FIG. 6A, for hypothalamic tissue obtained post mortem from a 65 year old male with BMI 27. GPR101 expression is shown for serial sections numbered 160 and 177. CRH expression is shown for serial section number 153. POMC expression is shown for serial section number 171. From inspection of FIG. 6A, it is apparent that in human hypothalamus GPR101 expression is spatially more concordant with POMC expression than with CRH expression.

GPR101 was also detected in human brain in the caudate, the putamen, the globus pallidum and in the nucleus of the solitary tract.

B. Expression of GPR101 in POMC Neurons in Human Hypothalamic Arcuate Nucleus

Expression of GPR101 by POMC neurons in human hypothalamic arcuate nucleus was investigated by in situ hybridization histochemical analysis, using radiolabeled ($^{33}$P-labeled) antisense probe for GPR101 in combination with a digoxigenin (Dig)-labeled antisense probe for POMC. The analysis was carried out on serial sections prepared from human hypothalamic arcuate nucleus tissue obtained from post mortem donors, essentially as described in Example 14. The human GPR101 probe corresponded to the nucleotide sequence of SEQ ID NO: 1. The human POMC probe corresponded to human POMC coding sequence (see, e.g., GenBank® Accession No. BC065832).

Figure 6B:
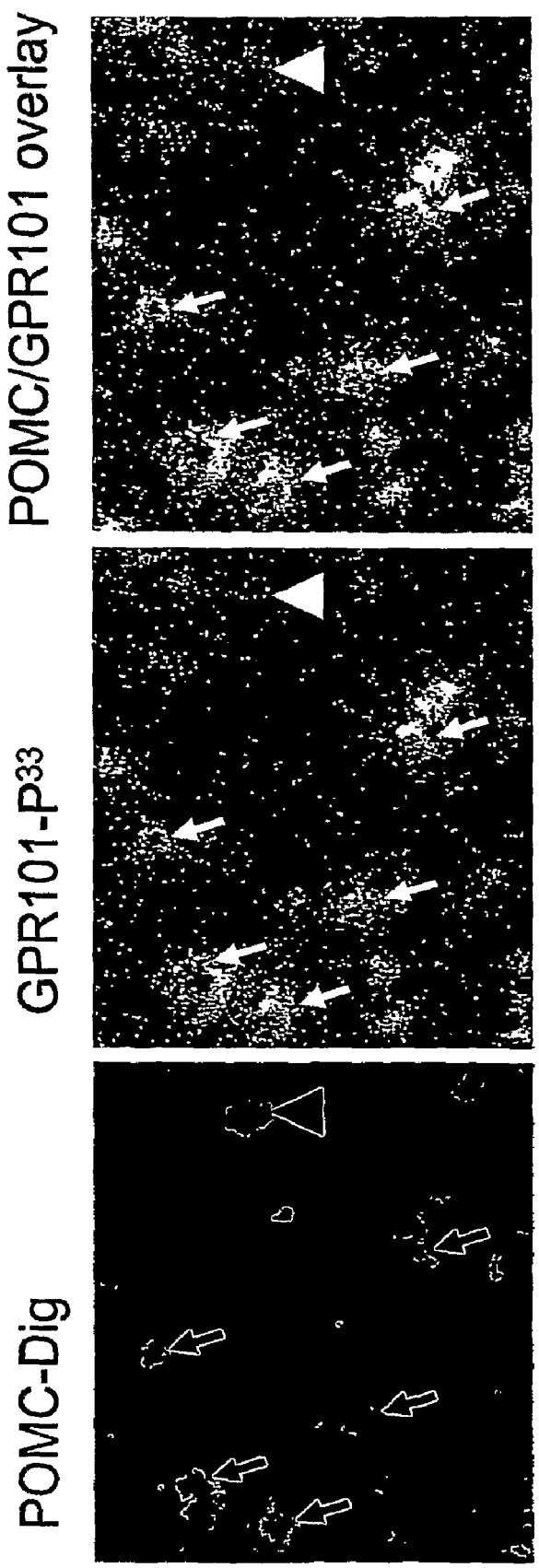

Results are presented in FIG. 6B. It was found that many POMC neurons within human hypothalamic arcuate nucleus express GPR101.

Example 17

Analysis of Hypothalamic Expression of GPR101 in Diet Induced Obese and db/db Mice A. Taqman Analysis Expression of GPR101 in brain regions, including hypothalamus, of diet induced obese mice and db/db mice was investigated by TaqMan analysis. The brain regions were hypothalamus (Hypo), caudate-putamen (Cpu) and cortex. All tissues were collected in-house from C57Bl/6J and db/db male mice (db/db mice have severe hyperphagia and obesity arising from a mutation in the leptin receptor gene) and RNA extracted using Trizol standard procedure. Diet Induced Obese (DIO) were fed with a high fat diet containing 59% Kcal/gm of fat (Bio-Serve S3282) for 25 weeks, whereas control (Control) mice were fed chow diet (Teklab 8604) for 25 weeks. For quantitative PCR (qPCR) analysis, cDNA was synthesized from total RNA using iScript cDNA synthesis kit from BioRad, following the manufacturer's protocol.

The qPCR reactions were performed using the ABI Prism 7900HT machine with the following temperatures and times: 50° C., 2 minutes; 95° C., 10 minutes; followed by 40 cycles of 95° C., 15 seconds and 60° C., 1 minute.

Primers and probe sequences used for qPCR analysis mouse GPR101 were as follows:

```
Forward Primer-
5'-TCAGGCTAGCAGCGCAAAG-3'         (SEQ ID NO: 18)

Reverse Primer-
5'-AATGTTGCACTGATTGGCATCT-3'      (SEQ ID NO: 19)

TaqMan MGB probe-6FAM-
5'-CAGACACCGGCCGC-3'              (SEQ ID NO: 20)
```

Expression of beta-actin (b-actin) was used as an internal control.

Figure 7A:
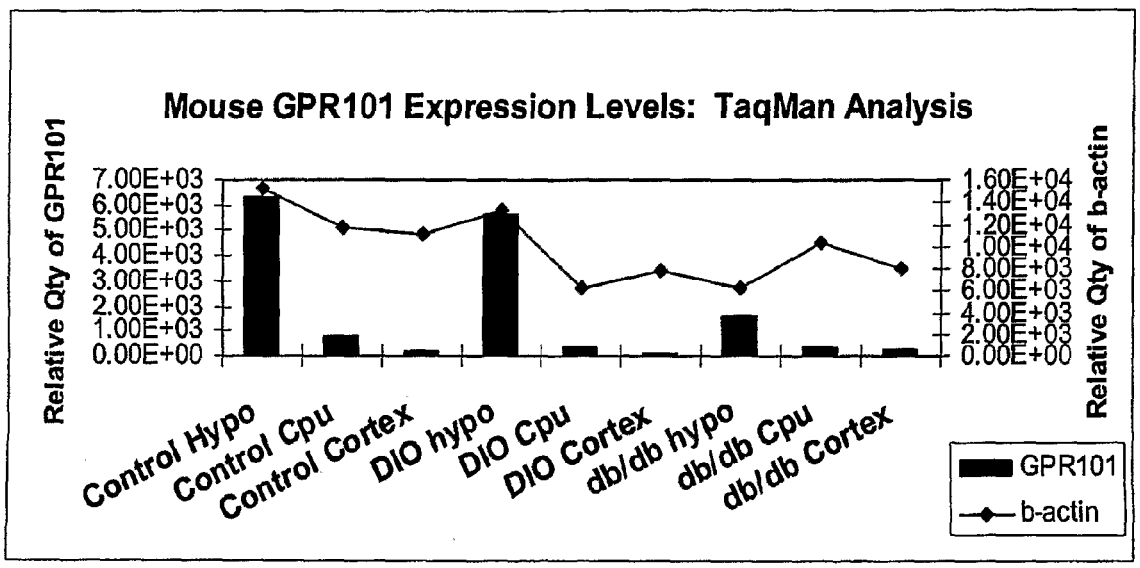
FIGS. 7A to 7B. A. TaqMan analysis of GPR101 expression in diet induced obese and db/db mice. B. In situ hybridization histochemical analysis of GPR101 expression in diet induced obese and db/db mice. (See, Example 17.)

Results are presented in FIG. 7A. Hypothalamic expression of GPR101 observed for the control mice was retained in the diet induced obese mice and db/db mice. Diet induced obese mice and db/db mice can be used as animal models of obesity for therapeutic intervention with a compound of the invention, e.g., a compound having agonist or partial agonist activity at mouse GPR101.

B. In Situ Hybridization Histochemical Analysis

Expression of GPR101 in brain of diet induced obese mice and db/db mice was investigated by in situ hybridization histochemical analysis carried out on serial sections prepared from hypothalamus. In situ hybridization histochemical analysis was carried out essentially as described in Example 13B. Polynucleotide corresponding to nucleotides 1197-1536 of SEQ ID NO: 3 was used to make antisense probe.

Figure 7B:

Results are presented in FIG. 7B. Expression of GPR101 observed for the control mice was retained in the diet induced obese mice and db/db mice. Diet induced obese mice and db/db mice can be used as animal models of obesity for therapeutic intervention with a compound of the invention, e.g., a compound having agonist or partial agonist activity at mouse GPR101.

Example 18

Analysis of Hypothalamic Expression of GPR101 in Obese Fa/Fa Zucker Rats

Expression of GPR101 in brain regions, including hypothalamus, of obese Fa/Fa Zucker male rats was investigated by TaqMan analysis. The brain regions were hypothalamus (Hypo), caudate-putamen (Cpu) and cortex. All tissues were collected in-house from Sprague Dawley (SD), lean fa/Fa Zucker, and obese Fa/Fa Zucker male rats and RNA extracted using Trizol standard procedure. For quantitative PCR (qPCR) analysis, cDNA was synthesized from total RNA using iScript cDNA synthesis kit from BioRad, following the manufacturer's protocol.

The qPCR reactions were performed using the ABI Prism 7900HT machine with the following temperatures and times: 50° C., 2 minutes; 95° C., 10 minutes; followed by 40 cycles of 95° C., 15 seconds and 60° C., 1 minute.

Primers and probe sequences used for qPCR analysis rat GPR101 were as follows:

```
Forward Primer-
5'-GGGCTGGAACTGAGCACTGA-3'        (SEQ ID NO: 21)

Reverse Primer-
5'-CG GTCCGTGTTTGCCTTT-3'         (SEQ ID NO: 22)

TaqMan MGB probe-6FAM-
5'-TCCAGGCTAGCAGCG-3'              (SEQ ID NO: 23)
```

Expression of beta-actin (b-actin) was used as an internal control.

Figure 8:
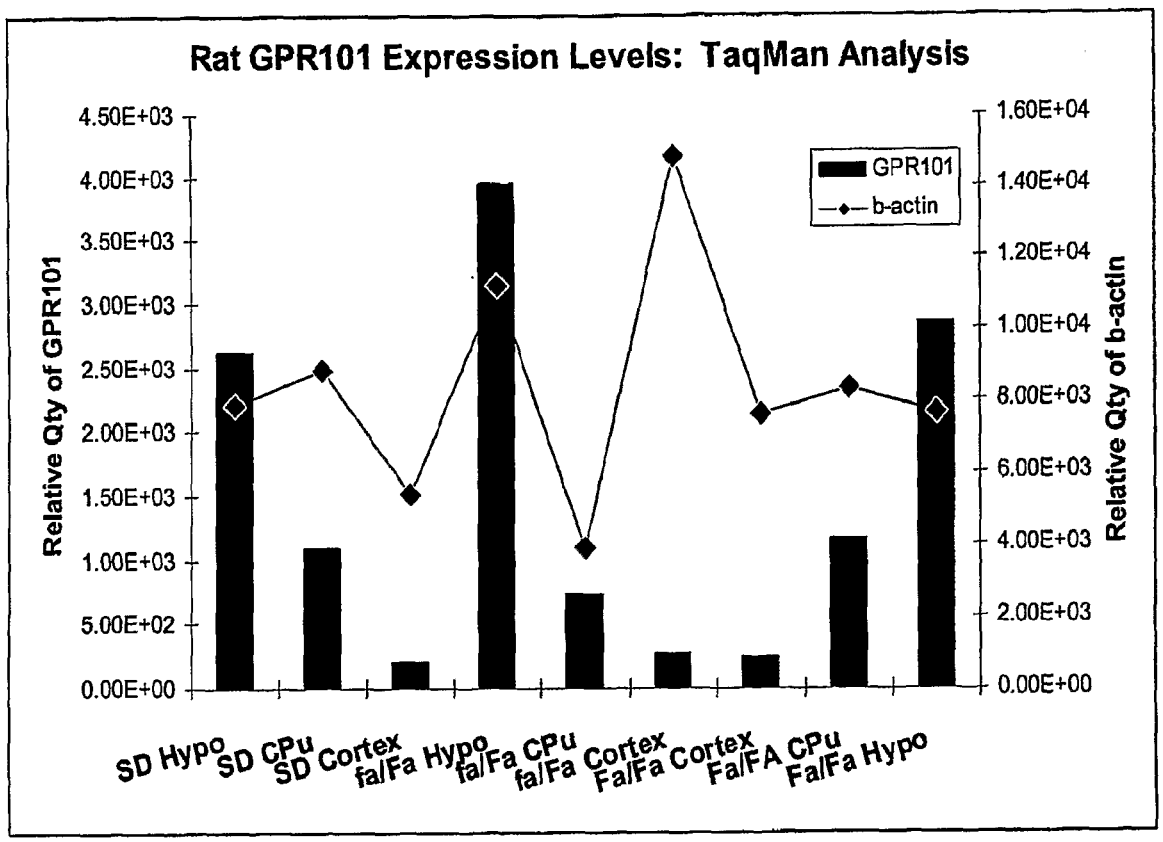
FIG. 8. Analysis of hypothalamic expression of GPR101 in obese Fa/Fa Zucker rats. (See, Example 18.)

Results are presented in FIG. 8. Hypothalamic expression of GPR101 observed for the control mice was retained in the obese Fa/Fa Zucker rats. Obese Fa/Fa Zucker rats can be used in animal models of obesity for therapeutic intervention with a compound of the invention, e.g., a compound having agonist or partial agonist activity at rat GPR101.

Example 19

Ex-Vivo Stimulation of Hypothalamic α-MSH Secretion by GPR101 Agonist

A compound of the invention, e.g. a compound having agonist activity at rat GPR101, can be shown to stimulate hypothalamic secretion of a POMC-derived biologically active peptide such as α-MSH using an in vitro hypothalamic slice assay (see, e.g., Fong et al, Neurosci Lett (2000) 283:5-8; and Abbott et al, Endocrinology (2003) 144:3943-3949).

Rats are killed by rapid decapitation and the brains removed. Slices (400 μM thick) from whole rat hypothalamus are prepared using a Vibratome with ice cold low calcium medium (consisting of the following components: 10 mM D-glucose, 26 mM $NaHCO_3$, 114 mM NaCl, 5 mM KCl, 1.2 mM $KH_2PO_4$, 10 mM HEPES, 9.1 mM $MgSO_4$, 0.2 mM $CaCl_2$; pH 7.4). The slices are allowed to achieve room temperature in the low calcium medium. The slices are then transferred to artificial cerebrospinal fluid (aCSF; 10 mM D-glucose, 26 mM $NaHCO_3$, 114 mM NaCl, 5 mM KCl, 1.2 mM $KH_2PO_4$, 10 mM HEPES, 1.3 mM $MgSO_4$, 2.4 mM $CaCl_2$; pH 7.4) and allowed to equilibrate at 37° C. for 1 h. The slices are then incubated for one hour at 37° C. in the presence or absence (vehicle alone) of a compound of the invention, e.g. a compound having agonist activity at rat GPR101. A preferred concentration of the compound is 0.001-100 μM. Other preferred concentration is selected from the group consisting of 1 nM, 10 nM, 100 nM, 1 μM, 10 μM, 25 μM, 50 μM and 100 μM. Following the one hour incubation, the supernatant is collected and frozen.

The supernatant samples are then run through a CIS column and lyophilized. α-MSH secretion (the amount of α-MSH released into the supernatant) is measured using an ELISA kit obtained from Phoenix Pharmaceuticals. Release of α-MSH into the supernatant is expressed as percentage of maximal release elicited by the effect of 56 nM KCl in hypothalamic slice assay.

Example 20

In Vivo Effects of a GPR101 Agonist on Increased Adiposity Induced by a High-Fat Diet in Mice An agonist of GPR101 receptor can be shown to confer protection from increased adiposity induced by a high fat diet.

Two groups of age- and sex-matched 5-30 week old wild-type C57Bl/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (e.g., D12266B, Research Diet, 31.8% fat/Kcal; or Bio-Serve S3282, 59% Kcal/gm of fat), for a period of 4-15 weeks. Over the course of the 4-15 week period, an agonist of GPR101 receptor having agonist activity at mouse GPR101 receptor or vehicle alone is injected daily into the tail vein. A preferred dose of the GPR10 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At the conclusion of the 4-15 week period, the mice are euthanized by $CO_2$ inhalation, and the epididymal and inguinal footpads are harvested and weighed as a measure of adiposity. The results can demonstrate that the GPR101 agonist confers protection from (that is, decreases) the increased adiposity (increased weight of the epididymal and inguinal footpads) induced by a high fat diet.

It is expressly contemplated that the GPR101 agonist can be a selective GPR101 agonist. It is expressly contemplated that a high fat diet having less or more than 31.8% fat/Kcal can be used. It is expressly contemplated that administration of the agonist can be other than intravenous, for example that administration of the agonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

It is also expressly contemplated that a GPR101 agonist can be shown to decrease adiposity in obese db/db mice and in obese Fa/Fa Zucker rats fed chow diet (e.g., Teklab 8604).

Example 21

In Vivo Effects of a GPR101 Agonist on Increased Percentage Body Fat Induced by a High-Fat Diet in Mice An agonist of GPR101 receptor can be shown to confer protection from increased percentage body fat induced by a high fat diet. Two groups of age- and sex-matched 5-30 week old wild-type C57Bl/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (e.g., D12266B, Research Diet, 31.8% fat/Kcal; or Bio-Serve S3282, 59% Kcal/gm of fat), for a period of 4-15 weeks. Over the course of the 4-15 week period, an agonist of GPR101 receptor having agonist activity at mouse GPR101 receptor or vehicle alone is injected daily into the tail vein. A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At the conclusion of the 4-15 week period, the mice are euthanized by $CO_2$ inhalation and percentage body fat is evaluated by determining body composition by densitometry using Dual energy X-ray absorptiometry (DEXA) (Lunar PIXImus, Lunar PIXImus Corp., Madison, Wis.). The data are analyzed using Lunar PIXImus 2.2.0 software according to the manufacturer's instructions. The results can demonstrate that the GPR101 agonist confers protection from (that is, decreases) the increased percentage body fat induced by a high fat diet.

It is expressly contemplated that the GPR101 agonist can be a selective GPR101 agonist. It is expressly contemplated that a high fat diet having less or more than 31.8% fat/Kcal can be used. It is expressly contemplated that administration of the agonist can be other than intravenous, for example that administration of the agonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

It is also expressly contemplated that a GPR101 agonist can be shown to decrease percentage body fat in obese db/db mice and in obese Fa/Fa Zucker rats fed chow diet (e.g., Teklab 8604).

Example 22

In Vivo Effects of a GPR101 Agonist on Weight Gain Induced by a High-Fat Diet in Mice An agonist of GPR101 receptor can be shown to confer protection from weight gain induced by a high fat diet. Two groups of age- and sex-matched 5-30 week old wild-type C57Bl/6J mice are housed individually and allowed free access to water and food. The mice are maintained on a 12 hour artificial light/12 h dark cycle and kept under constant humidity (70%) and temperature (22° C.) conditions. Mice are allowed free access to high fat diet (e.g., D12266B, Research Diet, 31.8% fat/Kcal; or Bio-Serve S3282, 59% Kcal/gm of fat), for a period of 4-15 weeks. Over the course of the 4-15 week period, an agonist of GPR101 receptor having agonist activity at mouse GPR101 receptor or vehicle alone is injected daily into the tail vein. A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

At weekly intervals over the course of the 4-15 week period, the mice are weighed. The results can demonstrate that the GPR101 agonist confers protection from (that is, decreases) weight gain induced by a high fat diet.

It is expressly contemplated that the GPR101 agonist can be a selective GPR101 agonist. It is expressly contemplated that a high fat diet having less or more than 31.8% fat/Kcal can be used. It is expressly contemplated that administration of the agonist can be other than intravenous, for example that administration of the agonist can be intraperitoneal or oral. It is expressly contemplated that mice younger than 5 weeks or older than 30 weeks can be used. It is expressly contemplated that the period of injection can be less than 4 weeks or longer than 15 weeks. It is expressly contemplated that a non-human mammal other than mouse can be used, for example rat.

It is also expressly contemplated that a GPR101 agonist can be shown to decrease weight gain in obese db/db mice and in obese Fa/Fa Zucker rats fed chow diet (e.g., Teklab 8604). It is also expressly contemplated that a GPR101 agonist can be shown to decrease weight gain in dogs given free access to water and fed pelleted chow (see, e.g., Sasaki et al, J Vet Med Sci (1998) 60:465-469).

Example 23

In Vivo Effects of a GPR101 Agonist on Food Intake in Rats

An agonist of GPR101 receptor can be shown to inhibit food intake in food-deprived rats. Male (weight 250-275 g)

Sprague-Dawley (SD) rats are purchased from Harlan (San Diego, Calif.) and housed 4 per cage in a temperature controlled environment under a 17 h/7 h light/dark cycle (lights out at 10:00 am). Water and Chow is available (LabDiet 8604) ad libitum for two weeks. The animals are handled for 2 occasions during this time. On the morning of the study, the animals are individually housed with no food or bedding and dosed with compound or vehicle 30 minutes prior to lights out by injection into the tail vein. At lights out, the animals are given a pre-weighed amount of chow and placed near the food bowl. Two hours later the remaining chow was weighed and the study concluded.

A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg. It is expressly contemplated that the GPR101 agonist can be a selective GPR101 agonist. It is expressly contemplated that administration of the agonist can be other than intravenous, for example that administration of the agonist can be intraperitoneal or oral. It is expressly contemplated that a non-human mammal other than rat can be used, for example mouse or non-human primate.

It is also expressly contemplated that a GPR101 agonist can be shown to decrease food intake in food-deprived obese db/db mice and in obese Fa/Fa Zucker rats.

Example 24

In Vivo Effects of a GPR101 Agonist on Pyrexia in Rabbits

A compound of the invention, e.g. a compound having agonist activity at GPR101, can be shown to reduce fever (i.e., to have antipyretic activity, to be effective in treating pyrexia) using the rabbit model of pyrexia described here (see, e.g., Murphy et al, Science (1983) 221:192-193). Adult New Zealand White rabbits are implanted with cannulas in a lateral cerebral ventricle and restrained in conventional stocks in an environmental chamber at 23° C. A thermistor probe (Yellow Springs No. 701) is inserted 10 cm into the rectum and taped in place. Temperature measurements are made automatically at 10 min intervals with a MINC 11 computer connected to a Datalogger digital temperature recorder (United Systems). Leukocyte pyrogen is injected intravenously after a 1 h baseline temperature has been determined. Test of the antipyretic effect of, e.g., a compound having agonist activity at GPR101 is performed in two separate experiments on the same animals, with the control (vehicle alone) response to leukocyte pyrogen being determined for each animal before each experiment. Each dose of the compound is injected intracerebroventricularly 30 min after the test injection of pyrogen and temperature measurements are taken at 10 min intervals over a 4 h period thereafter. All injections of pyrogen are separated by at least 48 h to minimize the development of tolerance.

A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg. It is expressly contemplated that the GPR101 agonist can be a selective GPR101 agonist. It is expressly contemplated that administration of the compound can be other than intracerebroventricular, for example that administration of the compound can be intravenous, intraperitoneal or oral.

It is expressly contemplated that a non-human mammal other than rabbit can be used, for example mouse, rat or non-human primate. An exemplary rat model can be found in Qin-Heng et al, Am J Physiol (1998) 275 (Regulatory Integrative Comp Physiol 44:) R524-R530.

Example 25

In Vivo Effects of a GPR101 Agonist on Atherogenesis in Mice

Male apoE$^{-/-}$ mice (Jackson Laboratory, Bar Harbor, Me.) are fed a normal chow. The apolipoprotein E-deficient (apoE$^{-/-}$) mouse is an established animal model of atherosclerosis, developing extensive atherosclerotic lesions on a chow diet (Zhang et al, Science (1992) 258:468-471). At the age of 12 weeks, an agonist of GPR101 having agonist activity at mouse GPR101 or vehicle alone is injected daily into the tail vein. A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

The mice are anesthetized with an intraperitoneal injection of pentobarbital (50 mg/kg), and the hearts, which contain the aoritic sinus and aortic arch, are harvested 14 days after the injection of the GPR101 agonist. Hearts are also harvested from uninjected mice at the start of the experiment. Ten mice are used for each of the three experimental groups.

The frozen cross-sections (10 µM thick) of aortic sinus embedded in Optimal Cutting Temperature (OCT; Sakura Finetechnical Co., Ltd) compound after overnight fixation in 10% formalin are mounted on slides. For the analysis of plaque size, 3 sections (100 µM apart) from each mouse were stained with Oil Red O. The lesion size and the diameter of lipid droplets in the lesions are quantified with an image analyzing computer software, and the mean values are determined. The mean value for the group injection with the GPR101 agonist is compared with the mean value for the group injected with vehicle alone.

Data are presented as means±SEM and are analyzed by Student's t test or the Mann-Whitney U test, depending on their distribution pattern. A value of P<0.05 is considered statistically significant. See, e.g., Okamoto et al, Circulation (2002) 106:2767-2770.

These results can demonstrate that the GPR101 agonist is an inhibitor of atherogenesis.

It is expressly contemplated that in other embodiment a GPR101 agonist can be shown to be an inhibitor of atherogenesis in the ApoE$^{-/-}$ mice using a non-invasive in vivo technique (see, e.g., Fayad et al, Circulation (1998) 98:1541-1547). It is expressly contemplated that in other embodiment, administration of the agonist is other than intravenous, for example that administration of the agonist is intraperitoneal or oral. It is expressly contemplated that in other embodiment, treatment begins other than at 12 weeks of age, either earlier or later than at 12 weeks of age. It is expressly contemplated that in other embodiment treatment continues for less than or more than 14 days. It is expressly contemplated that injection may be other than daily.

Example 26

In Vivo Effects of a GPR101 Agonist on Chronic Inflammatory Arthritis in Mice

Both male and female MRL-lpr mice (Jackson Laboratory, Bar Harbor, Me.) are used at 13-14 weeks of age. MRL-lpr mice spontaneously develop a chronic inflammatory arthritis with similar characteristics to human rheumatoid arthritis including cell infiltration, pannus formation, bone and cartilage breakdown, and the presence of serum rheumatoid factor. The disease normally develops towards the end of the animal's life span; however, injection with complete Freund's adjuvant (CFA) initiates early onset and increases the severity of arthritis (Rakay et al, J Immunol (1993) 151:5081-5087).

On Day 0 of each experiment, all groups of mice are injected with CFA intradermally into a thoracic and an inguinal site with 0.05 ml CFA supplemented to 10 mg/ml with heat inactivated *Mycobacterium tuberculosis* H37 Ra (Difco, Detroit, Mich.). Immediately, an agonist of GPR101 having agonist activity at mouse GPR101 or vehicle alone is injected daily into the tail vein. A preferred dose of the GPR101 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

Treatment is continued for 30 days. For quantifying swelling, ankle widths are measured with a micrometer. The statistical comparison of paired sets of ankle width measurements is carried out using the Student's t test.

Histopathological Analysis

At day 30 after CFA priming, the hind paws are fixed in buffered formalin. After decalcification in 10% formic acid for 48 hours, the tissues are processed for paraffin embedding. Serial sections of the tarso-metatarsal joints are cut to a thickness of 5 mm and stained with hematoxylin and eosin. Sections are examined by an individual without knowledge of the experimental protocol. A minimum of 10 sections/joint are assessed and scored to provide a semiquantitative measure of subsynovial inflammation (0, normal; 1 focal inflammatory infiltrates; 2, inflammatory infiltrate that dominates the cellular histology), synovial hyperplasia (0, normal; 1, a continuous, minimum three-layer thick, synovial lining seen in one joint; 2, minimum three-layer thick, synovial lining detected in several joints), pannus formation and cartilage erosion (0, normal; 1, pannus partially covered cartilage surfaces without evident cartilage loss; 2, pannus connected to evident cartilage loss), bone destruction (0, normal; 1, detectable destruction of bone by the pannus or osteoclast activity; 2, the pannus or osteoclast activity has destroyed a significant part of the bone), and finally, overall pathology is the overall assessment derived by the summation of the values for these criteria [see, e.g., Gong et al, J Exp Med (1997) 186:131-137]. Statistical analysis of the histopathology indices is done using the Student's t test.

These results can demonstrate that the GPR101 agonist is an inhibitor of a chronic inflammatory arthritis, for example that the GPR101 agonist is an inhibitor of rheumatoid arthritis.

It is expressly contemplated that in other embodiment, administration of the agonist is other than intravenous, for example that administration of the agonist is intraperitoneal or oral. It is expressly contemplated that in other embodiment, treatment begins other than at 13-14 weeks of age, either earlier or later than at 13-14 weeks of age. It is expressly contemplated that in other embodiment treatment continues for less than or more than 30 days. It is expressly contemplated that injection may be other than daily.

What is claimed is:

1. A method of identifying a candidate compound that stimulates hypothalamic proopiomelanocortin (POMC)-derived biologically active peptide secretion, said method comprising:
   (a) contacting the candidate compound with a recombinant host cell or a membrane thereof that comprises a G protein-coupled receptor (GPCR), wherein said receptor comprises an amino acid sequence selected from the group consisting of:
      (i) the amino acid sequence of SEQ ID NO:2;
      (ii) the amino acid sequence of a GPCR encoded by a polynucleotide that is amplifiable by polymerase chain reaction (PCR) on a human genomic DNA sample using primers having the nucleotide sequence set forth in SEQ ID NO: 7 and SEQ ID NO: 8;
      (iii) the amino acid sequence of SEQ ID NO: 4;
      (iv) the amino acid sequence of SEQ ID NO: 6;
      (v) the amino acid sequence of a GPCR encoded by a polynucleotide hybridizing under stringent conditions to the full-length complement of SEQ ID NO: 1, SEQ ID NO: 3 or SEQ ID NO: 5;
      (vi) the amino acid sequence of a GPCR that has an amino acid sequence having at least 70% identity to SEQ ID NO: 2, SEQ ID NO: 4 or SEQ ID NO: 6; and
      (vii) the amino acid sequence of SEQ ID NO:2, but wherein the alanine at amino acid position 398 of SEQ ID NO:2 is substituted with an amino acid selected from the group consisting of lysine, arginine, and histidine,
   wherein the receptor couples to a G protein or, wherein the GPCR induces cAMP accumulation; and
   (b) determining the ability of the candidate compound to stimulate functionality of the GPCR;
   (c) administering a vertebrate with a candidate compound that stimulates functionality of the GPCR; and
   (d) measuring an energy homeostasis-related parameter of the vertebrate, wherein the energy homeostasis-related parameter is selected from the group consisting of body mass, adiposity, and percentage body fat due to food intake,
   wherein the ability of the candidate compound to decrease an energy homeostasis-related parameter of the vertebrate is indicative of the candidate compound being a compound that stimulates hypothalamic POMC-derived biologically active peptide secretion.

2. The method of claim 1, wherein the GPCR comprises the amino acid sequence of SEQ ID NO: 2.

3. The method of claim 1, wherein the GPCR comprises the amino acid sequence of a GPCR that has an amino acid sequence having at least 70% identity to SEQ ID NO: 2.

4. The method of claim 3, wherein the GPCR comprises an amino acid sequence having at least 85% identity to SEQ ID NO: 2.

5. The method of claim 1, wherein the POMC-derived biologically active peptide is selected from the group consisting of adrenocorticotropic hormone (ACTH), β-endorphin, alpha-melanocyte stimulating hormone (α-MSH), beta-melanocyte stimulating hormone (β-MSH) and gamma-melanocyte stimulating hormone (γ-MSH).

6. The method of claim 1, wherein said determining is through the measurement of the level of a second messenger.

7. The method of claim 6, wherein the second messenger is cAMP.

8. The method of claim 1, wherein said determining is by using a Melanophore assay or by measuring GTPγS binding to a membrane comprising the GPCR or by using a cAMP-responsive reporter assay.

9. The method of claim 1, wherein the vertebrate is a non-human mammal.

10. The method of claim 1, wherein the vertebrate is a human.

11. The method of claim 1, wherein the method comprises identifying an agonist of the GPCR.

12. The method of claim 11, wherein the agonist is an agonist of human GPR101.

13. The method of claim 1, wherein the method comprises identifying a partial agonist of the GPCR.

14. The method of claim 13, wherein the partial agonist is a partial agonist of human GPR101.

15. A method of screening candidate compounds as pharmaceutical agents for a POMC-derived biologically active peptide-related disorder, said method comprising:
   (a) contacting the candidate compound with a recombinant host cell or a membrane thereof that comprises a G protein-coupled receptor (GPCR), wherein said receptor comprises an amino acid sequence selected from the group consisting of:
      the amino acid sequence of SEQ ID NO:2;
      the amino acid sequence of a GPCR encoded by a polynucleotide that is amplifiable by polymerase chain reaction (PCR) on a human genomic DNA sample using primers having the nucleotide sequence set forth in SEQ ID NO: 7 and SEQ ID NO: 8;
      (iii) the amino acid sequence of SEQ ID NO: 4;
      (iv) the amino acid sequence of SEQ ID NO: 6;
      (v) the amino acid sequence of a GPCR encoded by a polynucleotide hybridizing under stringent conditions to the full-length complement of SEQ ID NO: 1, SEQ ID NO: 3 or SEQ ID NO: 5;
      (vi) the amino acid sequence of a GPCR that has an amino acid sequence having at least 70% identity to SEQ ID NO: 2, SEQ ID NO: 4 or SEQ ID NO: 6; and
      (vii) the amino acid sequence of SEQ ID NO:2, but wherein the alanine at amino acid position 398 of SEQ ID NO:2 is substituted with an amino acid selected from the group consisting of lysine, arginine, and histidine,
      wherein the receptor couples to a G protein or, wherein the GPCR induces cAMP accumulation; and
   (b) detecting a ligand bound to said GPCR,
   (c) administering a vertebrate with a ligand that binds to said GPCR; and
   (d) measuring an energy homeostasis-related parameter of the vertebrate, wherein the energy homeostasis-related parameter is selected from the group consisting of body mass, adiposity, and percentage body fat due to food intake,
   wherein the ability of the ligand to decrease an energy homeostasis-related parameter of the vertebrate is indicative of the ligand being suitable as a pharmaceutical agent for a POMC-derived biologically active peptide-related disorder.

16. The method of claim 15, wherein the GPCR comprises the amino acid sequence of SEQ ID NO: 2.

17. The method of claim 15, wherein the POMC-derived biologically active peptide is selected from the group consisting of adrenocorticotropic hormone (ACTH), β-endorphin, alpha-melanocyte stimulating hormone (α-MSH), beta-melanocyte stimulating hormone (β-MSH) and gamma-melanocyte stimulating hormone (γ-MSH).

18. The method of claim 15, wherein the GPCR comprises an amino acid sequence having at least 70% identity to SEQ ID NO: 2.

19. The method of claim 18, wherein the GPCR comprises an amino acid sequence having at least 85% identity to SEQ ID NO: 2.

20. The method of claim 15, wherein the ligand that decreases an energy homeostasis-related parameter of the vertebrate is a ligand of human GPR101.

21. The method of claim 20, wherein the ligand of human GPR101 is a selective ligand.

22. The method of claim 15, wherein the vertebrate is a non-human mammal.

23. The method of claim 15, wherein the vertebrate is a human.

24. A method of identifying a compound that stimulates hypothalamic POMC-derived biologically active peptide secretion, said method comprising:
   (a) measuring an energy homeostasis-related parameter of a vertebrate, the vertebrate having been administered a GPR101 ligand, wherein the energy homeostasis-related parameter is selected from the group consisting of body mass, adiposity, and percentage body fat due to food intake;
   wherein the ability of the GPR101 ligand to decrease an energy homeostasis-related parameter of the vertebrate is indicative of a compound that stimulates hypothalamic POMC-derived biologically active peptide secretion.

25. The method of claim 24, wherein the vertebrate is a non-human mammal.

26. The method of claim 24, wherein the vertebrate is a human.

27. The method of claim 24, wherein the POMC-derived biologically active peptide is selected from the group consisting of adrenocorticotropic hormone (ACTH), β-endorphin, alpha-melanocyte stimulating hormone (α-MSH), beta-melanocyte stimulating hormone (β-MSH) and gamma-melanocyte stimulating hormone (γ-MSH).

28. The method of claim 24, wherein the GPR101 ligand that decreases an energy homeostasis-related parameter of the vertebrate is further identified as a ligand of human GPR101.

29. The method of claim 24, wherein the GPR101 ligand that decreases an energy homeostasis-related parameter of the vertebrate is an antibody.

30. The method of claim 24, wherein the GPR101 ligand that decreases an energy homeostasis-related parameter of the vertebrate is a selective GPR101 ligand having a selectivity for GPR101 over GPR161.

31. The method of claim 24, wherein the method identifies said GPR101 ligand as a GPR101 agonist.

32. The method of claim 31, wherein the agonist has an EC50 of less than 10 μM.

33. The method of claim 31, wherein the agonist has an EC50 of less than 1 μM.

34. The method of claim 31, wherein the agonist has an EC50 of less than 100 nM.

35. The method of claim 31, wherein the agonist has a selectivity for GPR101 over GPR161 of at least 10-fold.

36. The method of claim 31, wherein the agonist is a GPR101 partial agonist.

37. The method of claim 31, wherein the agonist is an agonist of human GPR101.

38. A method of identifying a compound that stimulates hypothalamic proopiomelanocortin (POMC)-derived biologically active peptide secretion, said method comprising:

(a) administering a vertebrate a GPR101 ligand; and
(b) measuring an energy homeostasis-related parameter of the vertebrate, wherein the energy homeostasis-related parameter is selected from the group consisting of body mass, adiposity, and percentage body fat due to food intake, wherein the ability of the GPR101 ligand to decrease an energy homeostasis-related parameter of the vertebrate is indicative of the GPR101 ligand being a compound that stimulates hypothalamic POMC-derived biologically active peptide secretion.

39. The method of claim 38, wherein the vertebrate is a non-human mammal.

40. The method of claim 38, wherein the vertebrate is a human.

41. The method of claim 38, wherein the POMC-derived biologically active peptide is selected from the group consisting of adrenocorticotropic hormone (ACTH), β-endorphin, alpha-melanocyte stimulating hormone (α-MSH), beta-melanocyte stimulating hormone (β-MSH) and gamma-melanocyte stimulating hormone (γ-MSH).

42. The method of claim 38, wherein the GPR101 ligand is further identified as a ligand of human GPR101.

43. The method of claim 38, wherein the GPR101 ligand is an antibody.

44. The method of claim 38, wherein the GPR101 ligand is a selective GPR101 ligand, said selective. GPR101 ligand having a selectivity for GPR101 over GPR161.

45. The method of claim 38, wherein the method identifies said GPR101 ligand as a GPR101 agonist.

46. The method of claim 45, wherein the agonist has an EC50 of less than 10 μM.

47. The method of claim 45, wherein the agonist has an EC50 of less than 1 μM.

48. The method of claim 45, wherein the agonist has an EC50 of less than 100 nM.

49. The method of claim 45, wherein the GPR101 agonist has a selectivity for GPR101 over GPR161 of at least 10-fold.

50. The method of claim 45, wherein the agonist is an agonist of human GPR101.

51. The method of claim 45, wherein the agonist is a GPR101 partial agonist.

52. A method of identifying a compound that stimulates hypothalamic POMC-derived biologically active peptide secretion, said method comprising:
(a) measuring a modulation of energy homeostasis in a vertebrate, the vertebrate having been administered a GPR101 ligand, wherein the modulation is selected from the group consisting of modulation of obesity, modulation of satiety, and modulation of hyperphagia, wherein the ability of the GPR101 ligand to oppose obesity, to promote satiety, or to oppose hyperphagia in the vertebrate is indicative of the GPR101 ligand being a compound that stimulates hypothalamic POMC-derived biologically active peptide secretion.

53. The method of claim 52, wherein the vertebrate is a non-human mammal.

54. The method of claim 52, wherein the vertebrate is a human.

55. A method of identifying a compound that stimulates hypothalamic proopiomelanocortin (POMC)-derived biologically active peptide secretion, said method comprising:
(a) administering a vertebrate a GPR101 ligand; and
(b) measuring a modulation of energy homeostasis in the vertebrate, wherein the modulation is selected from the group consisting of modulation of obesity, modulation of satiety, and modulation of hyperphagia, wherein the ability of the GPR101 ligand to oppose obesity, to promote satiety, or to oppose hyperphagia in the vertebrate is indicative of the GPR101 ligand being a compound that stimulates hypothalamic POMC-derived biologically active peptide secretion.

56. The method of claim 55, wherein the vertebrate is a non-human mammal.

57. The method of claim 55, wherein the vertebrate is a human.

* * * * *

UNITED STATES PATENT AND TRADEMARK OFFICE
CERTIFICATE OF CORRECTION

PATENT NO. : 8,142,762 B2  
APPLICATION NO. : 12/298740  
DATED : March 27, 2012  
INVENTOR(S) : Didier Bagnol Page 1 of 1

It is certified that error appears in the above-identified patent and that said Letters Patent is hereby corrected as shown below:

In claim 15, at column 123, line 25, before "the", insert -- (i) --.

In claim 15, at column 123, line 26, before "the", insert -- (ii) --.

In claim 44, column 125, line 28, delete "selective.", and insert -- selective --.

Signed and Sealed this  
Fifteenth Day of May, 2012

David J. Kappos  
*Director of the United States Patent and Trademark Office*

SEQUENCE LISTING

```
<160> NUMBER OF SEQ ID NOS: 23

<210> SEQ ID NO 1
<211> LENGTH: 1527
<212> TYPE: DNA
<213> ORGANISM: Homo sapiens

<400> SEQUENCE: 1
atgacgtcca cctgcaccaa cagcacgcgc gagagtaaca gcagccacac gtgcatgccc        60
ctctccaaaa tgcccatcag cctggcccac ggcatcatcc gctcaaccgt gctggttatc       120
ttcctcgccg cctctttcgt cggcaacata gtgctggcgc tagtgttgca gcgcaagccg       180
cagctgctgc aggtgaccaa ccgttttatc tttaacctcc tcgtcaccga cctgctgcag       240
atttcgctcg tggcccctg ggtggtggcc acctctgtgc ctctcttctg gcccctcaac       300
agccacttct gcacggccct ggttagcctc acccacctgt tcgccttcgc cagcgtcaac       360
accattgtcg tggtgtcagt ggatcgctac ttgtccatca tccaccctct ctcctacccg       420
tccaagatga cccagcgccg cggttacctg ctcctctatg gcacctggat tgtggccatc       480
ctgcagagca ctcctccact ctacggctgg ggccaggctg cctttgatga gcgcaatgct       540
ctctgctcca tgatctgggg ggccagcccc agctacacta ttctcagcgt ggtgtccttc       600
atcgtcattc cactgattgt catgattgcc tgctactccg tggtgttctg tgcagcccgg       660
aggcagcatg ctctgctgta caatgtcaag agacacagct tggaagtgcg agtcaaggac       720
tgtgtggaga atgaggatga agagggagca gagaagaagg aggagttcca ggatgagagt       780
gagtttcgcc gccagcatga aggtgaggtc aaggccaagg agggcagaat ggaagccaag       840 gacgcagcc tgaaggccaa ggaaggaagc acggggacca gtgagagtag tgtagaggcc       900
aggggcagcg aggaggtcag agagagcagc acggtggcca gcgacggcag catggagggt       960
```

```
aaggaaggca gcaccaaagt tgaggagaac agcatgaagg cagacaaggg tcgcacagag    1020
gtcaaccagt gcagcattga cttgggtgaa gatgacatgg agtttggtga agacgacatc    1080
aatttcagtg aggatgacgt cgaggcagtg aacatcccgg agagcctccc acccagtcgt    1140
cgtaacagca acagcaaccc tcctctgccc aggtgctacc agtgcaaagc tgctaaagtg    1200
atcttcatca tcattttctc ctatgtgcta tccctggggc cctactgctt tttagcagtc    1260
ctggccgtgt gggtggatgt cgaaacccag gtaccccagt gggtgatcac cataatcatc    1320
tggcttttct tcctgcagtg ctgcatccac ccctatgtct atggctacat gcacaagacc    1380
attaagaagg aaatccagga catgctgaag aagttcttct gcaaggaaaa gccccgaaa     1440 gaagatagcc acccagacct gcccggaaca gagggtggga ctgaaggcaa gattgtccct    1500
tcctacgatt ctgctacttt tccttga                                       1527
```

<210> SEQ ID NO 2
<211> LENGTH: 508
<212> TYPE: PRT
<213> ORGANISM: Homo sapiens

<400> SEQUENCE: 2

```
Met Thr Ser Thr Cys Thr Asn Ser Thr Arg Glu Ser Asn Ser Ser His
1               5                   10                  15

Thr Cys Met Pro Leu Ser Lys Met Pro Ile Ser Leu Ala His Gly Ile
            20                  25                  30

Ile Arg Ser Thr Val Leu Val Ile Phe Leu Ala Ala Ser Phe Val Gly
        35                  40                  45

Asn Ile Val Leu Ala Leu Val Leu Gln Arg Lys Pro Gln Leu Leu Gln
    50                  55                  60

Val Thr Asn Arg Phe Ile Phe Asn Leu Leu Val Thr Asp Leu Leu Gln
65                  70                  75                  80

Ile Ser Leu Val Ala Pro Trp Val Val Ala Thr Ser Val Pro Leu Phe
                85                  90                  95

Trp Pro Leu Asn Ser His Phe Cys Thr Ala Leu Val Ser Leu Thr His
            100                 105                 110

Leu Phe Ala Phe Ala Ser Val Asn Thr Ile Val Val Ser Val Asp
        115                 120                 125

Arg Tyr Leu Ser Ile Ile His Pro Leu Ser Tyr Pro Ser Lys Met Thr
    130                 135                 140

Gln Arg Arg Gly Tyr Leu Leu Leu Tyr Gly Thr Trp Ile Val Ala Ile
145                 150                 155                 160

Leu Gln Ser Thr Pro Pro Leu Tyr Gly Trp Gly Gln Ala Ala Phe Asp
                165                 170                 175

Glu Arg Asn Ala Leu Cys Ser Met Ile Trp Gly Ala Ser Pro Ser Tyr
            180                 185                 190

Thr Ile Leu Ser Val Val Ser Phe Ile Val Ile Pro Leu Ile Val Met
        195                 200                 205

Ile Ala Cys Tyr Ser Val Val Phe Cys Ala Ala Arg Arg Gln His Ala
    210                 215                 220

Leu Leu Tyr Asn Val Lys Arg His Ser Leu Glu Val Arg Val Lys Asp
225                 230                 235                 240

Cys Val Glu Asn Glu Asp Glu Glu Gly Ala Glu Lys Lys Glu Glu Phe
                245                 250                 255

Gln Asp Glu Ser Glu Phe Arg Gln His Gly Glu Val Lys Ala
            260                 265                 270
```

```
Lys Glu Gly Arg Met Glu Ala Lys Asp Gly Ser Leu Lys Ala Lys Glu
        275                 280                 285

Gly Ser Thr Gly Thr Ser Glu Ser Ser Val Glu Ala Arg Gly Ser Glu
    290                 295                 300

Glu Val Arg Glu Ser Ser Thr Val Ala Ser Asp Gly Ser Met Glu Gly
305                 310                 315                 320

Lys Glu Gly Ser Thr Lys Val Glu Glu Asn Ser Met Lys Ala Asp Lys
                325                 330                 335

Gly Arg Thr Glu Val Asn Gln Cys Ser Ile Asp Leu Gly Glu Asp Asp
            340                 345                 350

Met Glu Phe Gly Glu Asp Ile Asn Phe Ser Glu Asp Val Glu
        355                 360                 365

Ala Val Asn Ile Pro Glu Ser Leu Pro Pro Ser Arg Arg Asn Ser Asn
370                 375                 380

Ser Asn Pro Pro Leu Pro Arg Cys Tyr Gln Cys Lys Ala Ala Lys Val
385                 390                 395                 400

Ile Phe Ile Ile Ile Phe Ser Tyr Val Leu Ser Leu Gly Pro Tyr Cys
                405                 410                 415

Phe Leu Ala Val Leu Ala Val Trp Val Asp Val Glu Thr Gln Val Pro
            420                 425                 430

Gln Trp Val Ile Thr Ile Ile Ile Trp Leu Phe Phe Leu Gln Cys Cys
        435                 440                 445

Ile His Pro Tyr Val Tyr Gly Tyr Met His Lys Thr Ile Lys Lys Glu
    450                 455                 460

Ile Gln Asp Met Leu Lys Lys Phe Phe Cys Lys Glu Lys Pro Pro Lys
465                 470                 475                 480

Glu Asp Ser His Pro Asp Leu Pro Gly Thr Glu Gly Gly Thr Glu Gly
                485                 490                 495

Lys Ile Val Pro Ser Tyr Asp Ser Ala Thr Phe Pro
            500                 505

<210> SEQ ID NO 3
<211> LENGTH: 1536
<212> TYPE: DNA
<213> ORGANISM: Mus musculus

<400> SEQUENCE: 3
atgccaccca gctgcactaa cagtactcaa gagaacaatg gcagtcgagt gtgcctcccc        60
ctctccaaga tgcctattag tgtagctcac ggcatcatcc gctcagttgt gctgctcgtc       120
atccttggtg tagcctttct gggtaacgta gtgctgggtt atgtattgca ccgtaagcca       180
aacttgctgc aggtgaccaa ccggttcata tttaacctgc ttgtcactga cctgctgcag       240
gttgctctcg tggcccctg gtggtgtcc actgccattc ctttcttctg gcctctcaac        300
atccacttct gcactgccct ggttagcctc acccacttat ttgcctttgc tagtgtcaat       360
accattgtgg tggtgtcagt tgatcgttac ctgaccatca tccaccctct ttcctaccca       420
tccaagatga ccaaccgacg tagttatatt ctcctctatg gcacctggat tgcagccttc       480
ctgcagagca cacctccact ctatggctgg ggccacgcta cttttgatga ccgtaatgcc       540
ttctgttcca tgatctgggg agccagccct gcctatacgg ttgtcagtgt ggtatccttc       600
ctcgttattc cactgggtgt tatgattgcc tgctattctg tggtgttcgg tgcagcccgg       660
aggcagcaag ctctcctgta taaggccaag agccaccgct tggaggtgag agtcgaggac       720 tctgtgtgc atgagaatga agagggagca aagaagaggg atgagttcca ggacaagaat        780
gagttccagg ccaagatgg aggtggtcag gccgaggcta agggaagcag ctccatggaa        840
```

-continued

```
gagagtccca tggtagccga gggcagcagc cagaagaccg gaaaaggaag cctggatttc     900
agtgcaggta tcatggaggg caaggacagt gacgaggtca gtaatggcag catggagggg     960
ctggaagtca tcactgaatt tcaggctagc agcgcaaagg cagacaccgg ccgcatagat    1020
gccaatcagt gcaacattga cgtgggcgaa gatgatgtag agtttggcat ggatgaaatt    1080
catttcaacg acgatgttga ggcgatgcgc attccagaga gcagtccacc cagtcgtcga    1140
aacagcacca gcgacccacc tttgcctcca tgctatgagt gcaaagctgc tagagtgatc    1200
ttcgtcatca tttccactta tgtgctatct ctggggccct actgcttct agcagtgctg     1260 gctgtgtggg tggatatcga taccagggta ccccagtggg tgatcaccat aataatctgg    1320 cttttttcc tgcagtgttg catccaccca tatgtctatg ctatatgca caagagcatc      1380 aagaaggaaa tccaggaggt actgaagaag ttaatctgta agaaaagccc ccctgtagaa    1440
gatagccacc ctgaccttca tgaaacggaa gctggtacag agggaggtat tgaaggcaag    1500
gctgtcccct cccatgattc agctacttca ccttaa                              1536
```

<210> SEQ ID NO 4
<211> LENGTH: 511
<212> TYPE: PRT
<213> ORGANISM: Mus musculus

<400> SEQUENCE: 4

```
Met Pro Pro Ser Cys Thr Asn Ser Thr Gln Glu Asn Asn Gly Ser Arg
1               5                   10                  15

Val Cys Leu Pro Leu Ser Lys Met Pro Ile Ser Val Ala His Gly Ile
            20                  25                  30

Ile Arg Ser Val Val Leu Leu Val Ile Leu Gly Val Ala Phe Leu Gly
        35                  40                  45

Asn Val Val Leu Gly Tyr Val Leu His Arg Lys Pro Asn Leu Leu Gln
    50                  55                  60

Val Thr Asn Arg Phe Ile Phe Asn Leu Leu Val Thr Asp Leu Leu Gln
65                  70                  75                  80

Val Ala Leu Val Ala Pro Trp Val Val Ser Thr Ala Ile Pro Phe Phe
                85                  90                  95

Trp Pro Leu Asn Ile His Phe Cys Thr Ala Leu Val Ser Leu Thr His
            100                 105                 110

Leu Phe Ala Phe Ala Ser Val Asn Thr Ile Val Val Ser Val Asp
        115                 120                 125

Arg Tyr Leu Thr Ile Ile His Pro Leu Ser Tyr Pro Ser Lys Met Thr
    130                 135                 140

Asn Arg Arg Ser Tyr Ile Leu Leu Tyr Gly Thr Trp Ile Ala Ala Phe
145                 150                 155                 160

Leu Gln Ser Thr Pro Pro Leu Tyr Gly Trp Gly His Ala Thr Phe Asp
                165                 170                 175

Asp Arg Asn Ala Phe Cys Ser Met Ile Trp Gly Ala Ser Pro Ala Tyr
            180                 185                 190

Thr Val Val Ser Val Val Ser Phe Leu Val Ile Pro Leu Gly Val Met
        195                 200                 205

Ile Ala Cys Tyr Ser Val Phe Gly Ala Ala Arg Arg Gln Gln Ala
    210                 215                 220

Leu Leu Tyr Lys Ala Lys Ser His Arg Leu Glu Val Arg Val Glu Asp
225                 230                 235                 240

Ser Val Val His Glu Asn Glu Glu Gly Ala Lys Lys Arg Asp Glu Phe
                245                 250                 255
```

```
Gln Asp Lys Asn Glu Phe Gln Gly Gln Asp Gly Gly Gly Gln Ala Glu
            260                 265                 270

Ala Lys Gly Ser Ser Met Glu Glu Ser Pro Met Val Ala Glu Gly
        275                 280                 285

Ser Ser Gln Lys Thr Gly Lys Gly Ser Leu Asp Phe Ser Ala Gly Ile
    290                 295                 300

Met Glu Gly Lys Asp Ser Asp Glu Val Ser Asn Gly Ser Met Glu Gly
305                 310                 315                 320

Leu Glu Val Ile Thr Glu Phe Gln Ala Ser Ser Ala Lys Ala Asp Thr
                325                 330                 335

Gly Arg Ile Asp Ala Asn Gln Cys Asn Ile Asp Val Gly Glu Asp Asp
            340                 345                 350

Val Glu Phe Gly Met Asp Glu Ile His Phe Asn Asp Asp Val Glu Ala
        355                 360                 365

Met Arg Ile Pro Glu Ser Ser Pro Pro Ser Arg Arg Asn Ser Thr Ser
    370                 375                 380

Asp Pro Pro Leu Pro Pro Cys Tyr Glu Cys Lys Ala Ala Arg Val Ile
385                 390                 395                 400

Phe Val Ile Ile Ser Thr Tyr Val Leu Ser Leu Gly Pro Tyr Cys Phe
                405                 410                 415

Leu Ala Val Leu Ala Val Trp Val Asp Ile Asp Thr Arg Val Pro Gln
            420                 425                 430

Trp Val Ile Thr Ile Ile Ile Trp Leu Phe Phe Leu Gln Cys Cys Ile
        435                 440                 445

His Pro Tyr Val Tyr Gly Tyr Met His Lys Ser Ile Lys Lys Glu Ile
    450                 455                 460

Gln Glu Val Leu Lys Lys Leu Ile Cys Lys Lys Ser Pro Pro Val Glu
465                 470                 475                 480

Asp Ser His Pro Asp Leu His Glu Thr Glu Ala Gly Thr Glu Gly Gly
                485                 490                 495

Ile Glu Gly Lys Ala Val Pro Ser His Asp Ser Ala Thr Ser Pro
            500                 505                 510

<210> SEQ ID NO 5
<211> LENGTH: 1527
<212> TYPE: DNA
<213> ORGANISM: Rattus norvegicus

<400> SEQUENCE: 5
atgccatcca gctgcaccaa cagtactcaa gagaacaaca gcagccgagt gtgcctgccc      60
ctctccaaga tgcctattag catcgctcac ggcatcatcc gctccgttgt gctgctcatc     120
atccttggtg tagcctttgt gggtaacgta gtgctgggtt atgtattgca ccgtaagcca     180
cacttgctgc aggtgaccaa ccggttcata tttaacctgc ttgtcactga cctgctgcag     240
gttgctctcg tggcccctg gtggtgtcc actgccattc ctttcttctg gcctctcaac      300
atccacttct gcactgccct ggttagcctc acccactat ttgcctttgc cagtgtcaat      360
accattgtgg tggtgtcgat agatcgttac ctgtccatca tccaccctct ttcctaccca     420
tccaagatga ccaaccgacg tagttacatt ctcctctatg cacctggat tgcagccttc     480 ctgcagagca cacctccact ctatggctgg ggccacgcca cttttgacga ccgtaatgcc     540
ttctgttcca tgatctgggg tgacagtcct gcctataccg ttgtcagtgt ggtatccttc     600
ctcgttattc cactgggtgt tatgattgcc tgctattcag tggtgtttgg tgcagccaga     660
aggcagcaag ctctcctgta taaggccaag agccaccgct tccaggtcag agtcaaggac     720
```

-continued

```
tctgtggtgc atgagaatga acagggagca aagagggatg aatgccagga cgagaatgag    780
tttgaggacc aagatgaagg tggtcaggaa agcaccagca tgttggatga gggtgccatg    840
gtagctgaga acagcagcat gaagaccgga gcaggaagcc tggatttctg tgcaagtatc    900
ctggcggcta tgggcagtga agaggtcagt aatgggagca tggaggggct ggaactgagc    960
actgaaatcc aggctagcag cgcaaaggca aacacggacc gcagagatgt caatcagtgc   1020
aacatttacg tgggcgaaga tgacgtagag tttggcatgg atgaaatcca tttcaacgag   1080
gatgatgtcg aggcaatgcg tattccagag agccgtccac ccagtcgtcg aaacagcacc   1140
agcaacccac ctttgcctcc atgctatgag tgcaaagctg ctagagtgat cttcatcatc   1200 atttctcct atgtgctgtc tctggggccc tactgcttcc tggcagtgct ggctgtgtgg    1260
gtggatatcg attcccaggt accccagtgg gtgatcacca taataatctg gcttttttttc  1320 ctgcagtgct gcgtccaccc atatgtctat ggctatatgc acaagagcat taagaaggaa   1380
atcaaggagg tactgaagaa gttaacctgt aagaaaagca cctctgtaga cgatagccat   1440
cctgagcttc gcgaaactga agctggcaca gagggaggta ctgaaggcaa ggctatcccc   1500
tctcatgatt cggctacttc accttaa                                       1527
```

<210> SEQ ID NO 6
<211> LENGTH: 508
<212> TYPE: PRT
<213> ORGANISM: Rattus norvegicus

<400> SEQUENCE: 6

```
Met Pro Ser Ser Cys Thr Asn Ser Thr Gln Glu Asn Asn Ser Ser Arg
1               5                   10                  15

Val Cys Leu Pro Leu Ser Lys Met Pro Ile Ser Ile Ala His Gly Ile
            20                  25                  30

Ile Arg Ser Val Val Leu Leu Ile Ile Leu Gly Val Ala Phe Val Gly
        35                  40                  45

Asn Val Val Leu Gly Tyr Val Leu His Arg Lys Pro His Leu Leu Gln
    50                  55                  60

Val Thr Asn Arg Phe Ile Phe Asn Leu Leu Val Thr Asp Leu Leu Gln
65                  70                  75                  80

Val Ala Leu Val Ala Pro Trp Val Val Ser Thr Ala Ile Pro Phe Phe
                85                  90                  95

Trp Pro Leu Asn Ile His Phe Cys Thr Ala Leu Val Ser Leu Thr His
            100                 105                 110

Leu Phe Ala Phe Ala Ser Val Asn Thr Ile Val Val Ser Ile Asp
        115                 120                 125

Arg Tyr Leu Ser Ile Ile His Pro Leu Ser Tyr Pro Ser Lys Met Thr
    130                 135                 140

Asn Arg Arg Ser Tyr Ile Leu Leu Tyr Gly Thr Trp Ile Ala Ala Phe
145                 150                 155                 160

Leu Gln Ser Thr Pro Pro Leu Tyr Gly Trp Gly His Ala Thr Phe Asp
                165                 170                 175

Asp Arg Asn Ala Phe Cys Ser Met Ile Trp Gly Asp Ser Pro Ala Tyr
            180                 185                 190

Thr Val Val Ser Val Val Ser Phe Leu Val Ile Pro Leu Gly Val Met
        195                 200                 205

Ile Ala Cys Tyr Ser Val Val Phe Gly Ala Ala Arg Arg Gln Gln Ala
    210                 215                 220

Leu Leu Tyr Lys Ala Lys Ser His Arg Phe Gln Val Arg Val Lys Asp
```

```
                225                 230                 235                 240
Ser Val Val His Glu Asn Glu Gln Gly Ala Lys Arg Asp Glu Cys Gln
                    245                 250                 255

Asp Glu Asn Glu Phe Glu Asp Gln Glu Gly Gly Gln Glu Ser Thr
            260                 265                 270

Ser Met Leu Asp Glu Gly Ala Met Val Ala Glu Asn Ser Ser Met Lys
        275                 280                 285

Thr Gly Ala Gly Ser Leu Asp Phe Cys Ala Ser Ile Leu Ala Ala Met
    290                 295                 300

Gly Ser Glu Glu Val Ser Asn Gly Ser Met Glu Gly Leu Glu Leu Ser
305                 310                 315                 320

Thr Glu Ile Gln Ala Ser Ser Ala Lys Ala Asn Thr Asp Arg Arg Asp
                325                 330                 335

Val Asn Gln Cys Asn Ile Tyr Val Gly Glu Asp Val Glu Phe Gly
            340                 345                 350

Met Asp Glu Ile His Phe Asn Glu Asp Val Glu Ala Met Arg Ile
        355                 360                 365

Pro Glu Ser Arg Pro Ser Arg Arg Asn Ser Thr Ser Asn Pro Pro
    370                 375                 380

Leu Pro Pro Cys Tyr Glu Cys Lys Ala Ala Arg Val Ile Phe Ile Ile
385                 390                 395                 400

Ile Phe Ser Tyr Val Leu Ser Leu Gly Pro Tyr Cys Phe Leu Ala Val
                405                 410                 415

Leu Ala Val Trp Val Asp Ile Asp Ser Gln Val Pro Gln Trp Val Ile
            420                 425                 430

Thr Ile Ile Ile Trp Leu Phe Phe Leu Gln Cys Cys Val His Pro Tyr
        435                 440                 445

Val Tyr Gly Tyr Met His Lys Ser Ile Lys Lys Glu Ile Lys Glu Val
    450                 455                 460

Leu Lys Lys Leu Thr Cys Lys Lys Ser Thr Ser Val Asp Asp Ser His
465                 470                 475                 480

Pro Glu Leu Arg Glu Thr Glu Ala Gly Thr Glu Gly Gly Thr Glu Gly
                485                 490                 495

Lys Ala Ile Pro Ser His Asp Ser Ala Thr Ser Pro
            500                 505

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
gctgttgcca tgacgtccac ctgcac                                          26

<210> SEQ ID NO 8
<211> LENGTH: 26
<212> TYPE: DNA
<213> ORGANISM: Artificial
<220> FEATURE:
<223> OTHER INFORMATION: primer

<400> SEQUENCE: 8
ggacagttca aggtttgcct tagaac                                          26

<210> SEQ ID NO 9
<211> LENGTH: 6
```

<212> TYPE: PRT
<213> ORGANISM: Artificial
<220> FEATURE:
<223> OTHER INFORMATION: synthetic peptide

<400> SEQUENCE: 9

Thr Leu Glu Ser Ile Met
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Glu Tyr Asn Leu Val
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Asp Cys Gly Leu Phe
1               5

<210> SEQ ID NO 12
<211> LENGTH: 36
<212> TYPE: DNA
<213> ORGANISM: Artificial
<220> FEATURE:
<223> OTHER INFORMATION: primer

<400> SEQUENCE: 12
gatcaagctt ccatggcgtg ctgcctgagc gaggag                                36

<210> SEQ ID NO 13
<211> LENGTH: 53
<212> TYPE: DNA
<213> ORGANISM: Artificial
<220> FEATURE:
<223> OTHER INFORMATION: primer

<400> SEQUENCE: 13
gatcggatcc ttagaacagg ccgcagtcct tcaggttcag ctgcaggatg gtg             53

<210> SEQ ID NO 14
<211> LENGTH: 1062
<212> TYPE: DNA
<213> ORGANISM: Artificial
<220> FEATURE:
<223> OTHER INFORMATION: chimeric polynucleotide

<400> SEQUENCE: 14
atggcgtgct gcctgagcga ggaggccaag aagcccggag gatcaacga cgagatcgag        60 cggcagctgc gcagggacaa gcgcgacgcc cgccggagc tcaagctgct gctgctgggg       120
acaggggaga gtggcaagtc gaccttcatc aagcagatga ggatcatcca cgggtcgggc      180
tactctgacg aagacaagcg cggcttcacc aagctggtgt atcagaacat cttcacggcc      240
atgcaggcca tgatcagagc gatggacaca ctcaagatcc catacaagta tgaacacaat      300

```
aaggctcatg cacaattggt tcgagaggtt gatgtggaga aggtgtctgc ttttgacgtc    360
cccgactacg cggcaataaa gagcttgtgg aatgatcctg aatccagga gtgctacgac     420
agacgacggg aatatcagtt atctgactct accaaatact atctgaatga cttggaccgt    480
gtagccgacc cttcctatct gcctacacaa caagacgtgc ttagagttcg agtccccact    540
acagggatca tcgaataccc ctttgactta caaagtgtca ttttcagaat ggtcgatgta    600
gggggccaaa ggtcagagag aagaaaatgg atccactgct tgaaaatgt cacctccatc     660
atgtttctag tagcgcttag cgaatatgat caagttcttg tggagtcaga caatgagaac    720
cgcatggagg agagcaaagc actctttaga acaattatca cctaccctg gttccagaac     780
tcctctgtga ttctgttctt aaacaagaaa gatcttctag aggagaaaat catgtattcc    840
cacctagtcg actactccc agaatatgat ggaccccaga gagatgccca ggcagctcga     900
gaattcatcc tgaaaatgtt cgtggacctg aaccccgaca gtgacaaaat catctactcc    960
cacttcacgt gcgccacaga taccgagaac atccgcttcg tctttgcagc cgtcaaggac   1020
accatcctgc agctgaacct gaaggactgc ggcctgttct aa                       1062
```

<210> SEQ ID NO 15
<211> LENGTH: 353
<212> TYPE: PRT
<213> ORGANISM: Artificial
<220> FEATURE:
<223> OTHER INFORMATION: chimeric polypeptide

<400> SEQUENCE: 15

```
Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240
```

-continued

```
Arg Met Glu Glu Ser Lys Ala Leu Phe Arg Thr Ile Ile Thr Tyr Pro
                245                 250                 255
Trp Phe Gln Asn Ser Ser Val Ile Leu Phe Leu Asn Lys Lys Asp Leu
            260                 265                 270
Leu Glu Glu Lys Ile Met Tyr Ser His Leu Val Asp Tyr Phe Pro Glu
        275                 280                 285
Tyr Asp Gly Pro Gln Arg Asp Ala Gln Ala Ala Arg Glu Phe Ile Leu
    290                 295                 300
Lys Met Phe Val Asp Leu Asn Pro Asp Ser Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Asp Cys Gly Leu
            340                 345                 350
Phe

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
ctttcttctg gcctctcaac atcc                                            24

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
cagaaggcat tacggtcatc aaaa                                            24

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
tcaggctagc agcgcaaag                                                  19

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
aatgttgcac tgattggcat ct                                              22

<210> SEQ ID NO 20
<211> LENGTH: 14
<212> TYPE: DNA
<213> ORGANISM: Artificial
<220> FEATURE:
<223> OTHER INFORMATION: synthetic probe
```

```
<400> SEQUENCE: 20
cagacaccgg ccgc                                                      14

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
gggctggaac tgagcactga                                                20

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
cggtccgtgt ttgcctt                                                   18

<210> SEQ ID NO 23
<211> LENGTH: 15
<212> TYPE: DNA
<213> ORGANISM: Artificial
<220> FEATURE:
<223> OTHER INFORMATION: synthetic probe

<400> SEQUENCE: 23
tccaggctag cagcg                                                     15
```